US007799823B2

(12) United States Patent
Barrett et al.

(10) Patent No.: US 7,799,823 B2
(45) Date of Patent: *Sep. 21, 2010

(54) ANDROGEN MODULATORS

(75) Inventors: Stephen Douglas Barrett, Hartland, MI (US); Victor Fedij, Brighton, MI (US); Lain-Yen Hu, Ann Arbor, MI (US); Donna M Iula, Ann Arbor, MI (US); Bruce A Lefker, Gales Ferry, CT (US); Raj Kumar Raheja, Ann Arbor, MI (US); Karen Sexton, Chelsea, MI (US); Jennifer Ann Van Camp, Ann Arbor, MI (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 935 days.

This patent is subject to a terminal disclaimer.

(21) Appl. No.: 11/557,225

(22) Filed: Nov. 7, 2006

(65) Prior Publication Data

US 2007/0072936 A1 Mar. 29, 2007

Related U.S. Application Data

(63) Continuation of application No. 11/415,935, filed on May 2, 2006, now Pat. No. 7,674,819.

(60) Provisional application No. 60/678,035, filed on May 5, 2005, provisional application No. 60/682,112, filed on May 18, 2005.

(51) Int. Cl.
*A61K 31/4015* (2006.01)
*C07D 207/12* (2006.01)

(52) U.S. Cl. ...................... 514/424; 548/544
(58) Field of Classification Search ............... 514/424; 548/544
See application file for complete search history.

(56) References Cited

U.S. PATENT DOCUMENTS

| 4,029,493 | A | 6/1977 | Theissen |
| 4,234,595 | A | 11/1980 | Kreighbaum et al. |
| 4,536,321 | A | 8/1985 | Sugimori et al. |
| 4,992,433 | A | 2/1991 | Stokbroekx et al. |
| 5,108,652 | A | 4/1992 | Eidenschink et al. |
| 5,316,755 | A | 5/1994 | Illig et al. |
| 5,847,166 | A | 12/1998 | Buchwald et al. |
| 5,910,493 | A | 6/1999 | Golbs et al. |
| 6,011,606 | A | 1/2000 | Ohe et al. |
| 2003/0175445 | A1 | 9/2003 | Kirsch et al. |
| 2003/0229129 | A1 | 12/2003 | Kraemer et al. |
| 2005/0182132 | A1 | 8/2005 | Hu et al. |
| 2006/0009427 | A1 | 1/2006 | Hu et al. |
| 2006/0252796 | A1* | 11/2006 | Barrett et al. ............... 514/317 |

FOREIGN PATENT DOCUMENTS

DE 10126434 A 7/1957

| DE | 3515633 | A | 11/1986 |
| DE | 3825170 | A1 | 1/1990 |
| DE | 4017019 | A1 | 11/1991 |
| DE | 4217928 | A1 | 12/1993 |
| EP | 15505 | | 9/1980 |
| EP | 0119756 | | 9/1984 |
| EP | 0193303 | | 9/1986 |
| EP | 221844 | A | 5/1987 |
| EP | 100172 | B1 | 8/1987 |
| EP | 269383 | A | 6/1988 |
| EP | 412814 | A | 2/1991 |
| EP | 419286 | A | 3/1991 |
| EP | 488474 | A1 | 6/1992 |
| EP | 0609587 | A | 8/1994 |
| EP | 0673986 | A2 | 3/1995 |
| EP | 654468 | A1 | 5/1995 |
| EP | 0579223 | | 10/1996 |
| EP | 0790235 | A1 | 8/1997 |
| EP | 1070753 | A2 | 1/2001 |
| EP | 1123933 | A1 | 8/2001 |
| EP | 0707007 | B1 | 12/2001 |
| EP | 1325910 | A1 | 7/2003 |
| EP | 1348433 | A | 10/2003 |
| EP | 1348701 | A | 10/2003 |
| GB | 2347423 | A | 8/1920 |
| GB | 1369696 | A | 10/1974 |
| GB | 2278054 | A | 11/1994 |

(Continued)

OTHER PUBLICATIONS

Database CA [Online] Chemical Abstracts Service, Columbus, Ohio, US; Yasuda, Kosuke et al: "Preparation of aliphatic nitrogenous five-membered ring compounds as dipeptidyl peptidase IV inhibitors" XP002350473 retrived from STN Database accession No. 136:325560.

Database CA [Online] Chemical Abstracts Service, Columbus, Ohio, US; Chaki, Hisaaki et al: "Preparation and formulation of alkylsulfonylbiphenyl and aminosulfonylbipbenyl derivatives as selective COX-2 inhibitors" XP002350472 retrieved from STN Database accession No. 125:300608.

Patent Abstracts of Japan vol. 13, No. 21 (C-560), Jan. 18, 1989 & JP 63227502A (SDS Biotech KK), Sep. 21, 1988.

Reiling B A et al: "Effect of prenatal androgenization on performance, lactation, carcass, and sensory traits of heifers in a single-calf heifer system" Journal of Animal Science, vol. 73, No. 4, 1995, pp. 986-992, XP0088065209 ISSN: 0021-8812.

Heitzman R J : "The effectiveness of anabolic agents in increasing rate of growth in farm animals; report on experiments in cattle." Environmental Quality and Safety. Supplement, 1976, No. 5, 1976, pp. 89-98, XP008065222 ISSN: 0340-4714.

Botzki, Salmen: "Structure based design . . . " Cominatorial Science, vol. 24, No. 4, 2005, pp. 458-469, XP008065218.

(Continued)

*Primary Examiner*—Celia Chang
(74) *Attorney, Agent, or Firm*—Raj J. Advani; Jeffrey H. Tidwell

(57) ABSTRACT

The present invention is directed to a new class of benzonitriles and to their use as androgen receptor modulators. Other aspects of the invention are directed to the use of these compounds to decrease excess sebum secretions and to stimulate hair growth.

10 Claims, No Drawings

FOREIGN PATENT DOCUMENTS

| | | |
|---|---|---|
| JP | 61189243 | 8/1986 |
| JP | 04124183 | 4/1992 |
| JP | 04300877 | 10/1992 |
| JP | 5310616 | 11/1993 |
| JP | 07309850 | 11/1995 |
| JP | 8325154 | 12/1996 |
| JP | 10007647 A | 1/1998 |
| WO | WO9219210 A2 | 11/1992 |
| WO | WO 94/05153 A | 3/1994 |
| WO | WO9510521 A1 | 4/1995 |
| WO | WO95/28969 | 11/1995 |
| WO | WO 9626921 | 9/1996 |
| WO | WO9735845 A1 | 10/1997 |
| WO | WO99/08673 A | 2/1999 |
| WO | WO99/17777 | 4/1999 |
| WO | WO0034247 A | 6/2000 |
| WO | WO0034269 A | 6/2000 |
| WO | WO0037430 | 6/2000 |
| WO | WO0059888 A | 10/2000 |
| WO | WO01/56989 A2 | 8/2001 |
| WO | WO02/06196 A1 | 1/2002 |
| WO | WO0218333 A | 3/2002 |
| WO | WO0220484 A | 3/2002 |
| WO | WO0236734 A | 5/2002 |
| WO | WO0241889 A | 5/2002 |
| WO | WO0270484 A | 6/2002 |
| WO | WO02/090332 A2 | 11/2002 |
| WO | WO03068754 | 5/2003 |
| WO | WO03066632 A | 8/2003 |
| WO | WO03068217 A | 8/2003 |
| WO | WO 03082787 | 10/2003 |
| WO | WO03/093243 A | 11/2003 |
| WO | WO2004110994 A1 | 12/2004 |
| WO | WO2005042464 A1 | 5/2005 |
| WO | WO2005080320 A1 | 9/2005 |
| WO | WO2005/102990 A | 11/2005 |
| WO | WO2006/006065 A | 1/2006 |
| WO | WO2006/018723 A2 | 2/2006 |
| WO | WO2006/024942 A | 3/2006 |

OTHER PUBLICATIONS

Abstract:: Arnold, Donald R. et al., Radical ions in photochemistry. Part 20. The photochemical nucleophile-olefin combination, aromatic substitution reaction. Canadian Journal of Chemistry (1988) 66(12), 3012-26.

Gregorio Asensio et al., Synthesis of an enantiopure 2-arylcyclohexanols form prochiral enol acetates by an enantioselective protonation/diasteroselective reduction sequence, Tetraheron: Asymmetry 14(2003) 3851-3855.

Alexandre Alexakis et al., Enantioselective Nucleophilic Opening fo meso Epoxides by Organolithium Reagents, Synlett Oct. 1998, pp. 1165-1167.

Shankar M. Shingh et al., Androgen Receptor Antagonists (Antiandrogens): Structure-Activity Relationships, Current Medicinal Chemistry, 2000, 7, 211-247.

Derwent English Abstract of German Patent Application (DE3939116A1).

Micropatent English Abstract of Japanese Patent (JP2001-247411).

Bohl, Casey E., et al, Structural basis for antagonism and resistance of bicalutamide in prostate cancer, PNAS, Apr. 26, 2005, vol. 102, No. 17 pp. 6201-6206.

Palucki, M. et al., "Palladium-catalyzed intermolecular carbon-oxygen bond formation; A new sysnthesis of aryl ethers" . . . J. Am. Chem. Soc., 1997, vol. 119, nr. 14, pp. 3395-3396.

Related United States co-pending U.S. Appl. No. 11/053,010, filed Feb. 8, 2005 now published as 2005-0182132A1 on Aug. 18, 2005.

Related United States co-pending U.S. Appl. No. 11/175,097, filed Jul. 5, 2005 now published as 2006-0009427A1 on Jan. 12, 2006.

Co-pending commonly assigned. U.S. Appl. No. 11/572,743, filed Aug. 5, 2005, now published as 2008-006475A1 on Mar. 13, 2008.

Co-pending commonly assigned. U.S. Appl. No. 11/572,143, filed Apr. 1, 2005, now published as 2008-006474A1 on Mar. 13, 2008.

Co-pending commonly assigned. U.S. Appl. No. 10/599,719, filed Apr. 14, 2005, now published as 2007-0197642 on Aug. 23, 2007.

Co-pending commonly assigned. U.S. Appl. No. 11/997,983, filed Jul. 27, 2006.

Co-pending commonly assigned. U.S. Appl. No. 11/572,760, filed Aug. 8, 2005.

Co-pending commonly assigned. U.S. Appl. No. 11/415,935, filed May 2, 2006.

Co-pending commonly assigned. U.S. Appl. No. 11/572,748, filed Aug. 22, 2005.

Kuwabe, S., et al., "Palladium-Catalized Intramolecular C-O Bond Formation", *J. Am. Chem. Soc.*, vol. 123, pp. 12202-12206 (2001).

* cited by examiner

ANDROGEN MODULATORS

CROSS REFERENCE TO RELATED APPLICATION

This is a continuation of application Ser. No. 11/415,935, filed May 2, 2006 which claims priority to U.S. Provisional Application Ser. No. 60/678,035, filed May 5, 2005 and U.S. Provisional Application Ser. No. 60/682,112, filed May 18, 2005, the contents of each are hereby incorporated by reference.

FIELD OF THE INVENTION

The present invention is directed to a new class of 4-lactam benzonitriles and to their use as androgen receptor modulators. Other aspects of the invention are directed to the use of these compounds to decrease sebum secretion and to stimulate hair growth.

BACKGROUND OF THE INVENTION

Alopecia, or balding, is a common problem which medical science has yet to alleviate. While androgens are associated with balding, the physiological mechanism by which this hair loss occurs is not known. However, it is known that hair growth is altered in individuals afflicted with alopecia.

Hair does not grow continuously but undergoes cycles of activity involving periods of growth, rest, and shedding. The human scalp typically contains from 100,000 to 350,000 hair fibers or shafts, which undergo metamorphosis in three distinct stages:

(a) during the growth phase (anagen) the follicle (i.e. the hair root) penetrates deep into the dermis with the cells of the follicle dividing rapidly and differentiating in the process of synthesizing keratin, the predominant component of hair. In non-balding humans, this growth phase lasts from one to five years;

(b) the transitional phase (catagen) is marked by the cessation of mitosis and lasts from two to three weeks; and (c) the resting phase (telogen) in which the hair is retained within the scalp for up to 12 weeks, until it is displaced by new follicular growth from the scalp below.

In humans, this growth cycle is not synchronized. An individual will have thousands of follicles in each of these three phases. However, most of the hair follicles will be in the anagen phase. In healthy young adults, the anagen to telogen ratio can be as high as 9 to 1. In individuals with alopecia, this ratio is reduced to as low as 2:1.

Androgenetic alopecia arises from activation of an inherited sensitivity to circulating androgenic hormones. It is the most common type of alopecia. It affects both men (50%) and women (30%), primarily of Caucasian origin. Gradual changes in the width and length of the hair shaft are experienced over time and with increasing age, prematurely in some. Terminal hair is gradually converted to short, wispy, colorless vellus hair. As a consequence, men in their 20's and women in their 30's and 40's begin to notice their hair becoming finer and shorter. In males, most of the hair loss occurs at the crown of the head. Females experience a thinning over their entire scalp. As discussed above, the anagen to telogen ratio is reduced significantly, resulting in less hair growth. Minoxidil, a potassium channel opener, promotes hair growth. Minoxidil is available commercially in the United States under the trademark, Rogaine®. While the exact mechanism of action of minoxidil is unknown, its impact on the hair growth cycle is well documented. Minoxidil promotes the growth of the hair follicle and increase the period of time that the hair follicle is in the anagen phase (i.e., increases the anagen to telogen ratio).

While minoxidil promotes hair growth, the cosmetic efficacy of this growth can vary widely. For example, Roenigk reported the results of a clinical trial involving 83 males who used a topical solution of 3% minoxidil for a period of 19 months. Hair growth occurred in 55% of the subjects. However, only 20% of the subjects considered the growth to be cosmetically relevant. (*Clin. Res.*, 33, No. 4, 914A, 1985). Tosti reported cosmetically acceptable re-growth in 18.1% of his subjects. (*Dermatologica*, 173, No. 3, 136-138, 1986). Thus, the need exists in the art for compounds having the ability produce higher rates of cosmetically acceptable hair growth in patients with alopecia.

SUMMARY OF THE INVENTION

In accordance with the present invention, a new class of androgen modulators has been discovered. These compounds, their salts, and solvates, thereof, may be represented by Formula I below:

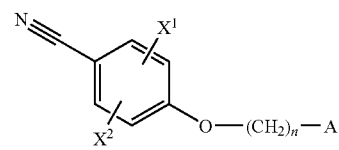

in which;

a) $X^1$ is represented by halogen, cyano, $C_1$-$C_6$ alkyl, $C_1$-$C_6$ alkoxy, $NO_2$, haloalkoxy, or haloalkyl, b) $X^2$ is represented by hydrogen, halogen, cyano, $C_1$-$C_6$ alkyl, $C_1$-$C_6$ alkoxy, $NO_2$, haloalkoxy, or haloalkyl, c) A is represented by:

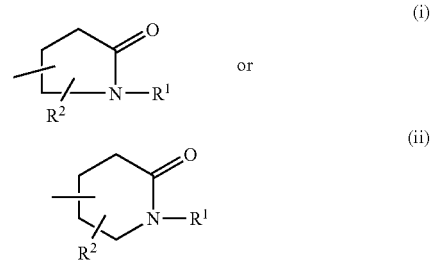

d) n is represented by the integer 0 or 1, e) $R^2$ is represented by a substituent selected from the group consisting of hydrogen, halogen, $C_1$-$C_6$ alkyl, $C_1$-$C_6$ alkoxy, haloalkyl, and haloalkoxy, f) $R^1$ is represented by a substituent selected from the group consisting of:
  i) hydrogen,
  ii) ($C_1$-$C_{12}$)alkyl, optionally substituted,
  iii) ($C_2$-$C_{12}$)alkenyl, optionally substituted,
  iv) ($C_2$-$C_{12}$)alkynyl, optionally substituted,
  v) ($C_3$-$C_{10}$)cycloalkyl, optionally substituted, vi) $(C_3-C_{10})$ cycloalkyl$(C_1-C_6)$alkyl, in which the alkyl and cycloalkyl moieties may each be optionally substituted,
vii) $(C_6-C_{10})$aryl optionally substituted,
viii) $(C_6-C_{10})$aryl $(C_1-C_6)$alkyl, in which the alkyl and aryl moieties may each be optionally substituted,
ix) heteroaryl, optionally substituted,
x) heteroaryl$(C_1-C_{12})$alkyl, in which the heteroaryl and alkyl moieties may each be optionally substituted,
xi) heterocyclic, optionally substituted,
xii) heterocyclic$(C_1-C_{12})$alkyl, in which the alkyl and heterocyclic moieties may each be substituted,
xiii) $—SO_2—(CH_2)_t—Y^1—Y^2—Y^1$,
xiv) $—C(O)—(CH_2)_t—Y^1—Y^2—Y^1$,
xv) $—(CH_2)_z—SR^3$,
xvi) $—(CH_2)_z—OR^3$,
xvii) $—(CH_2)_z—NR^4R^5$,
xviii) $—(CH_2)_z—COOR^3$,
xix) $—(CH_2)_z—CONR^3$,
xx) $—(CH_2)_z—NCOR^3$,
xxi) $—(CH_2)_zOCOR^3$ and;
xxii) $—(CH_2)_z—Y^1—Y^2—Y^1$,
g) z is represented by an integer from 1 to 6,
h) t is represented by an integer from 0 to 6,
i) each $Y^1$ is absent, or is represented by a substituent selected from the group consisting of $(C_3-C_{10})$cycloalkyl, $(C_6-C_{10})$ aryl, heteroaryl, and heterocyclic, any of which may be optionally substituted,
j) $Y^2$ is represented by a substituent selected from the group consisting of:
  a. hydrogen,
  b. $(C_1-C_{12})$alkyl, optionally substituted,
  c. $(C_2-C_{12})$alkenyl, optionally substituted,
  d. $(C_2-C_{12})$alkynyl, optionally substituted,
  e. $(C_3-C_{10})$cycloalkyl, optionally substituted,
  f. $(C_3-C_{10})$ cycloalkyl$(C_1-C_6)$alkyl, in which the alkyl and cycloalkyl moieties may each be optionally substituted,
  g. $(C_6-C_{10})$aryl, optionally substituted,
  h. $(C_6-C_{10})$aryl $(C_1-C_6)$alkyl, in which the alkyl and aryl moieties may each be optionally substituted,
  i. heteroaryl, optionally substituted,
  j. heteroaryl$(C_1-C_{12})$alkyl, in which the heteroaryl and alkyl moieties may each be optionally substituted,
  k. heterocyclic, optionally substituted,
  l. heterocyclic$(C_1-C_{12})$alkyl, in which the alkyl and heterocyclic moieties may each be substituted,
  m. $(CH_2)_z—SR^3$,
  n. $(CH_2)_z—OR^3$,
  o. $(CH_2)_z—NR^4R^5$,
  p. $(CH_2)_z—COOR^3$,
  q. $(CH_2)_z—CONR^3$,
  r. $(CH_2)_z—NCOR^3$, and
  s. $(CH_2)_zOCOR^3$;
k) $R^3$ is represented by a substituent selected from the group consisting of hydrogen, $(C_1-C_{12})$alkyl which may be optionally substituted, optionally substituted $(C_6-C_{10})$aryl, and $(C_6-C_{10})$aryl $(C_1-C_6)$alkyl, in which the alkyl and aryl moieties may each be optionally substituted,
l) $R^4$ is represented by hydrogen, $C_1-C_6$ alkyl, or $C_6-C_{10}$ aryl,
m) $R^5$ is represented by hydrogen or $C_1-C_6$ alkyl;
n) or $R^4$ and $R^5$ may be combined with the adjacent nitrogen atom to form a heteroaryl or heterocyclic moiety.

The compounds of Formula I are androgen receptor modulators. The compounds have affinity for the androgen receptor and will cause a biological effect by binding to the receptor. Typically, the compounds will act as antagonists. In selected embodiments they will act as partial agonists, full agonists, or tissue selective agonists. As androgen receptor modulators, the compounds can be used to treat, or alleviate, conditions associated with inappropriate activation of the androgen receptor. Examples of such conditions for antagonists include, but are not limited to, acne, excess sebum secretion, androgenic alopecia, hormone dependant cancers such as prostrate cancer, and hirsutism. Those compounds that are partial agonists, or full agonists, can be used to treat osteoporosis, hypogonadism, anemia, or to stimulate increases in muscle mass, especially in wasting diseases.

The invention is also directed to pharmaceutical compositions containing at least one of the compounds, in an amount effective to modulate activation of the androgen receptor. In a further embodiment, the invention is directed to an article of manufacture containing at least one of the compounds packaged for retail distribution, in association with instructions advising the consumer on how to use the compound to alleviate a condition associated with inappropriate activation of the androgen receptor. An additional embodiment is directed to the use of a compound as a diagnostic agent to detect inappropriate activation of the androgen receptor.

In a further embodiment, the compounds are used topically to induce and/or stimulate hair growth and/or to slow down hair loss. The compounds may also be used topically in the treatment of excess sebum and/or of acne.

In a further embodiment the compounds can be used in livestock such as cattle, pigs, chickens, fish, etc. The compounds will increase the growth rate, and enhance the lean meat to fat ratio in the animals, and improve feed efficiency.

DETAILED DESCRIPTION OF THE INVENTION

The headings within this document are only being utilized expedite its review by the reader. They should not be construed as limiting the invention or claims in any manner.

Definitions and Exemplification

As used throughout this application, including the claims, the following terms have the meanings defined below, unless specifically indicated otherwise. The plural and singular should be treated as interchangeable, other than the indication of number:

a. "halogen" refers to a chlorine, fluorine or bromine atom.

b. "$C_1-C_6$ alky" refers to a branched or straight chained alkyl group containing from 1 to 6 carbon atoms, such as methyl, ethyl, n-propyl, isopropyl, n-butyl, isobutyl, pentyl, etc.

c. "$C_1-C_6$ alkyl, optionally substituted" refers to a branched or straight chained alkyl group containing from 1 to 6 carbon atoms, such as methyl, ethyl, n-propyl, isopropyl, n-butyl, isobutyl, pentyl, etc. Such an alkyl group may be optionally substituted, in which up to 6 hydrogen atoms are replaced by a substituent selected from the group consisting of halogen, haloalkyl, hydroxy, thiol, cyano, and $NR^6R^7$ in which $R^6$ and $R^7$ are each independently represented by hydrogen or $C_1-C_6$ alkyl.

d. "$C_1-C_{12}$ alkyl, optionally substituted" refers to a branched or straight chained alkyl group containing from 1 to 12 carbon atoms, such as methyl, ethyl, n-propyl, isopropyl, n-butyl, isobutyl, hexyl, octyl, decyl, etc. Such an alkyl group may be optionally substituted, in which up to 8 hydrogen atoms are replaced by a substituent selected from the group consisting of halogen, haloalkyl, hydroxy, thiol, cyano, and NR$^6$R$^7$, in which R$^6$ and R$^7$ are as defined above.

e. "C$_2$-C$_{12}$ alkenyl optionally substituted" refers to a straight-chain or branched-chain hydrocarbon radical containing from 2 to 12 carbon atoms and 1, or more, carbon-carbon double bonds. Examples of alkenyl radicals include ethenyl, propenyl, 1,4-butadienyl, 1-hexenyl, 1,3-octadienyl and the like. Such an alkenyl group may be optionally substituted, in which up to 8 hydrogen atoms are replaced by a substituent selected from the group consisting of halogen, haloalkyl, hydroxy, thiol, cyano, and NR$^6$R$^7$, in which R$^6$ and R$^7$ are as defined above.

f. "C$_2$-C$_{12}$ alkynyl optionally substituted" refers to a straight-chain or branched-chain hydrocarbon radical containing from 2 to 12 carbon atoms and having 1, or more, carbon-carbon triple bonds. Examples of alkynyl radicals include ethynyl, propynyl, butynyl, octynyl, and the like. Such an alkynyl group may be optionally substituted, in which up to 8 hydrogen atoms are replaced by a substituent selected from the group consisting of halogen, hydroxy, haloalkyl, thiol, cyano, and —NR$^6$R$^7$, in which R$^6$ and R$^7$ are as defined above.

g. "haloalkyl" refers to a branched or straight chained alkyl group containing from 1 to 6 carbon atoms, in which at least one hydrogen atom is replaced with a halogen (i.e. C$_1$-C$_6$ haloalkyl). Examples of suitable haloalkyl's include chloromethyl, difluoromethyl, trifluoromethyl, 1-fluro-2-chloro-ethyl, 5-fluoro-hexyl, 3-difluro-isopropyl, 3-chloro-isobutyl, etc.

h. "(C$_1$-C$_2$)alkyl substituted with one or more halogen atoms" refers to a straight chained alkyl group containing 1 or 2 carbon atoms, i.e., methyl or ethyl in which at least one hydrogen atom is replaced with a halogen (i.e. for example trifluromethyl, dichloromethyl, etc.).

i. "(C$_1$-C$_2$)alkoxy substituted with one or more halogen atoms" refers to a straight chained alkoxy group containing 1 or 2 carbon atoms, i.e., methoxy or ethoxy in which at least one hydrogen atom is replaced with a halogen (i.e. for example trifluoromethoxy, difluromethoxy, etc.)

j. "C$_1$-C$_6$ alkoxy" refers to a straight or branched chain alkoxy group containing from 1 to 6 carbon atoms, such as methoxy, ethoxy, n-propoxy, isopropoxy, n-butoxy, isobutoxy, pentoxy, etc.

k. "haloalkoxy" refers to a branched or straight chained alkoxy group containing from 1 to 6 carbon atoms, in which at least one hydrogen atom is replaced with a halogen (i.e. C$_1$-C$_6$ haloalkoxy). Examples of suitable haloalkoxy's include chloromethoxy, difluoromethoxy, trifluoromethoxy, 1-fluro-2-chloro-ethoxy, 5-fluoro-hexoxy, 3-difluro-isopropoxy, 3-chloro-isobutoxy, etc.

l. "(C$_6$-C$_{10}$)aryl" optionally substituted means a cyclic, aromatic hydrocarbon containing from 6 to 10 carbon atoms. Examples of aryl groups include phenyl, naphthyl and biphenyl. Such an aryl moiety may be optionally substituted with up to 4 non-hydrogen substituents, each substituent is independently selected from the group consisting of halogen, nitro, cyano, hydroxy, (C$_1$-C$_6$)alkyl, (C$_1$-C$_6$)alkoxy, (C$_1$-C$_2$)alkyl substituted with one or more halogens, (C$_1$-C$_2$)alkoxy substituted with one or more halogens, —C(O)—R$^6$, —C(O)—O—R$^6$, SR$^6$, SO$_2$R$^6$ and NR$^6$R$^7$. R$^6$ and R$^7$ are each independently represented by C$_1$-C$_6$ alkyl or hydrogen. These substituents may be the same or different and may be located at any position of the ring, that is chemically permissible.

m. "(C$_3$-C$_{10}$) cycloalkyl" optionally substituted refers to a saturated or partially saturated monocyclic, bicyclic or tricyclic alkyl radical wherein each cyclic moiety has 3 to 10 carbon atoms. Examples of cycloalkyl radicals include cyclopropyl, cyclobutyl, cyclopentyl, cyclohexyl, cyclooctyl, and the like. Such a cycloalkyl group may be optionally substituted, in which up to 4 hydrogen atoms are replaced by a substituent selected from the group consisting of halogen, cyano, nitro, hydroxy, (C$_1$-C$_6$)alkyl, (C$_1$-C$_6$)alkoxy, (C$_1$-C$_2$)alkyl substituted with one or more halogens, (C$_1$-C$_2$)alkoxy substituted with one or more halogens, —(O)—R$^6$, —(O)—O—R$^6$, SR$^6$, SO$_2$R$^6$ and NR$^6$R$^7$, in which R$^6$ and R$^7$ are as defined above.

n. "heteroaryl" refers to an aromatic ring having one, or more, heteroatoms selected from oxygen, nitrogen and sulfur. More specifically, it refers to a 5- or 6-, membered ring containing 1, 2, 3, or 4 nitrogen atoms; 1 oxygen atom; 1 sulfur atom; 1 nitrogen and 1 sulfur atom; 1 nitrogen and 1 oxygen atom; 2 nitrogen atoms and 1 oxygen atom; or 2 nitrogen atoms and 1 sulfur atom. The 5-membered ring has 2 double bonds and the 6-membered ring has 3 double bonds. The term heteroaryl also includes bicyclic groups in which the heteroaryl ring is fused to a benzene ring, heterocyclic ring, a cycloalkyl ring, or another heteroaryl ring. Examples of such heteroaryl ring systems include, but are not limited to, pyrrolyl, furanyl, thienyl, imidazolyl, oxazolyl, indolyl, thiazolyl, pyrazolyl, pyridinyl, pyrimidinyl, purinyl, quinolinyl, benzofuran, tetrazole, isoquinolinyl, oxadiazolyl, thiadiazolyl, isothiazolyl, isoxazolyl, triazolyl, benzo[b]thienyl, 2-, 4-, 5-, 6-, or 7-benzoxazolyl, 7-benzimidazolyl, or benzothiazolyl.

o. "heteroaryl, optionally substituted," refers to a heteroaryl moiety as defined immediately above, in which up to 4 carbon atoms of the heteroaryl moiety may be substituted with a substituent, each substituent is independently selected from the group consisting of halogen, cyano, nitro, hydroxy, (C$_1$-C$_6$)alkyl, (C$_1$-C$_6$) alkoxy, (C$_1$-C$_2$)alkyl substituted with one or more halogens, (C$_1$-C$_2$)alkoxy substituted with one or more halogens, SO$_2$R$^6$—(O)—R$^6$, —(O)—O—R$^6$ SR$^6$, and NR$^6$R$^7$, in which R$^6$ and R$^7$ are as defined above.

p. "heterocycle" or "heterocyclic ring" refers to any 3- or 4-membered ring containing a heteroatom selected from oxygen, nitrogen and sulfur; or a 5-, 6-, 7-, 8-, 9-, or 10-membered ring containing 1, 2, or 3 nitrogen atoms; 1 oxygen atom; 1 sulfur atom; 1 nitrogen and 1 sulfur atom; 1 nitrogen and 1 oxygen atom; 2 oxygen atoms in non-adjacent positions; 1 oxygen and 1 sulfur atom in non-adjacent positions; or 2 sulfur atoms in non-adjacent positions. The 5-membered ring has 0 to 1 double bonds, the 6- and 7-membered rings have 0 to 2 double bonds, and the 8, 9, or 10 membered rings may have 0, 1, 2, or 3 double bonds. The term "heterocyclic" also includes bicyclic groups in which any of the above heterocyclic rings is fused to a benzene ring, a cyclohexane or cyclopentane ring or another heterocyclic ring (for example, indolyl, quinolyl, isoquinolyl, tetrahydroquinolyl, benzofuryl, dihydrobenzofuryl or benzothienyl and the like). Heterocyclics include: pyrrolidinyl, tetrahydrofuranyl, tetrahydrothiophenyl, piperidinyl, piperazinyl, azepane, azocane, morpholinyl, isochromyl, quinolinyl, tetrahydrotriazine, tetrahydropyrazole, dihydro-oxathiol-4-yl, dihydro-1H-isoindole, tetrahydro-oxazolyl, tetrahydro-oxazinyl, q. "heterocyclic, optionally substituted" refers to a heterocyclic moiety as defined immediately above, in which up to 4 carbon atoms of the heterocycle moiety may be substituted with a substituent, each substituent is independently selected from the group consisting of halogen, cyano, nitro, hydroxy, $(C_1-C_6)$alkyl, $(C_1-C_6)$ alkoxy, $(C_1-C_2)$alkyl substituted with one or more halogens, $(C_1-C_2)$alkoxy substituted with one or more halogens, —(O)—$R^6$, —(O)—O—$R^6$, $SR^6$, $SO_2R^6$ and $NR^6R^7$, in which $R^6$ and $R^7$ are as defined above. Any nitrogen atom within such a heterocyclic ring may optionally be substituted with $(C_1-C_6)$ alkyl, if such substitution is chemically permissible.

thiomorpholinyl, tetrahydropyrimidinyl, dioxolinyl, octahydrobenzofuranyl, octahydrobenzimidazolyl, and octahydrobenzothiazolyl.

r. "androgen" refers to testosterone and its precursors and metabolites, and 5-alpha reduced androgens, including but not limited to dihydrotestosterone. Androgen refers to androgens from the testis, adrenal gland, and ovaries, as well as all forms of natural, synthetic and substituted or modified androgens.

s. "pharmaceutically acceptable" means suitable for use in mammals.

t. "salts" is intended to refer pharmaceutically acceptable salts and to salts suitable for use in industrial processes, such as the preparation of the compound.

u. "pharmaceutically acceptable salts" is intended to refer to either pharmaceutically acceptable acid addition salts" or "pharmaceutically acceptable basic addition salts" depending upon actual structure of the compound.

v. "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids, which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

w. "pharmaceutically acceptable basic addition salts" is intended to apply to any non-toxic organic or inorganic basic addition salts of the compounds represented by Formula I, or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

x. "prodrug" refers to compounds that are rapidly transformed in vivo to yield the parent compound of the above formulas, for example, by hydrolysis in blood. A thorough discussion is provided in T. Higuchi and V. Stella, "Pro-drugs as Novel Delivery Systems," Vol. 14 of the A.C.S. Symposium Series, and in Biorevesible Carriers in Drug Design, ed. Edward B. Roche, American Pharmaceutical Association and Pergamon Press, 1987, both of which are incorporated herein by reference.

y. "compound of Formula I", "compounds of the invention", and "compounds" are used interchangeably throughout the application and should be treated as synonyms.

z. "patient" refers to warm blooded animals such as, for example, guinea pigs, mice, rats, gerbils, cats, rabbits, dogs, monkeys, chimpanzees, stump tail macques, and humans.

aa. "treat" refers to the ability of the compounds to either relieve, alleviate, or slow the progression of the patient's disease (or condition) or any tissue damage associated with the disease.

bb. "livestock" refers to animals suitable for human meat consumption. Examples include pigs, cattle, chickens, fish, turkeys, rabbits, etc.

cc. "isomer" means "stereoisomer" and "geometric isomer" as defined below.

dd. "stereoisomer" means compounds that possess one or more chiral centers and each center may exist in the R or S configuration. Stereoisomers includes all diastereomeric, enantiomeric and epimeric forms as well as racemates and mixtures thereof.

ee. "geometric isomer" means compounds that may exist in cis, trans, anti, entgegen (E), and zusammen (Z) forms as well as mixtures thereof.

Certain of the compounds of the formula (I) may exist as geometric isomers. The compounds of the formula (I) may possess one or more asymmetric centers, thus existing as two, or more, stereoisomeric forms. The present invention includes all the individual stereoisomers and geometric isomers of the compounds of formula (I) and mixtures thereof. Individual enantierners can be obtained by chiral separation or using the relevant enantiomer in the synthesis.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention. The compounds may also exist in one or more crystalline states, i.e. polymorphs, or they may exist as amorphous solids. All such forms are encompassed by the claims.

All of the compounds of Formula I contain a benzonitrile moiety. To further exemplify the invention, the numbering system for this ring and its substitution pattern is shown below:

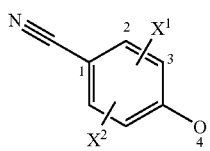

Position 1 of this benzonitrile is substituted with a cyano moiety as depicted above. Position 4 is substituted with an oxygen atom forming an ether moiety. The benzonitrile will be further substituted, as depicted by $X^1$, at any of position 2, 3, 5 or 6 with a halogen atom, a cyano group, a $(C_1-C_6)$ alkyl group, a $(C_1-C_6)$ alkoxy group, a nitro, a haloalkoxy moiety or a haloalkyl moiety. Typically, it will be a halogen or haloalkyl moiety located at the 2- or 6-position. More typically it will be trifluoromethyl located at the 2 or 6-position of the benzonitrile. The benzonitrile may optionally be further substituted, as indicated by $X^2$, with a third substituent, selected from the group consisting of halogen, cyano, $(C_1-C_6)$ alkyl, $(C_1-C_6)$ alkoxy, a nitro, haloalkoxy and haloalkyl which may be located at any remaining position of the benzonitrile.

All of the compounds of Formula I contain a lactam moiety. To further exemplify the invention, the numbering system for these rings is shown below. In one embodiment, the lactam is a 2-oxopyrrolidine, (i.e. hereinafter "ring (i)")

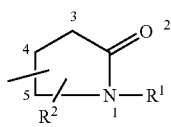

A nitrogen atom is located at position 1 of the lactam. It may optionally be substituted with one of the entities listed above for $R^1$. Position 2 will always be substituted with the oxo function depicted above. The lactam may be bonded to the ether linkage (if no is 0), or to the methylene moiety (if n is 1) at any of positions 3, 4, or 5. Typically, the lactam will be connected to the ether linkage via position 3. The lactam may be further substituted at the remaining positions as indicated by the $R^2$ moiety. Any of positions 3, 4, or 5 may be mono-substituted, or di-substituted (if chemically permissible). Typically, position 4 will be di-substituted with a lower alkyl moiety (i.e. $C_1-C_6$ alkyl). More typically position 4 will be di-substituted with two methyl functions.

In a second embodiment, the lactam moiety is a 2-oxo-piperidine as shown below (i.e. ring ii):

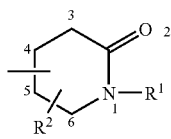

A nitrogen atom is located at position 1 of the lactam ring. It may optionally be substituted with one of the entities listed above for $R^1$. Position 2 will always be substituted with the oxo function depicted above. The lactam may be bonded to the ether linkage (if no is 0), or to the methylene moiety (if n is 1) at any of positions 3, 4, 5 or 6. Typically, the lactam will be connected to the ether linkage via position 3. The lactam may be further substituted at the remaining positions as indicated by the $R^2$ moiety. Any of positions 3, 4, 5, or 6 may be mono-substituted, or di-substituted (if chemically permissible).

More specific embodiments of the invention include compounds of Formula I in which:

i) $X^1$ is chloro or trifluoromethyl and is located at the 2-position of the phenyl ring, and $X^2$ is hydrogen;

ii) $X^1$ is chloro or trifluoromethyl and is located at the 2-position of the phenyl ring, $X^2$ is hydrogen, and n is 0;

iii) $X^1$ is trifluoromethyl and is located at the 2-position of the phenyl ring, $X^2$ is hydrogen, and n is 0;

iv) $X^1$ is trifluoromethyl and is located at the 2-position of the phenyl ring, $X^2$ is hydrogen, n is 0, and A is represented by ring (i);

v) $X^1$ is trifluoromethyl and is located at the 2-position of the phenyl ring, $X^2$ is hydrogen, n is 0, and A is represented by ring (i) in which R2 represents a di-substitution at position 4 of the pyrrolidine ring;

vi) $X^1$ is trifluoromethyl and is located at the 2-position of the phenyl ring, $X^2$ is hydrogen, n is 0 in which the oxygen atom is bonded to position 3 of the lactam, and A is represented by ring (i) in which $R^2$ represents a di-substitution at position 4 of the pyrrolidine ring;

vii) $X^1$ is trifluoromethyl and is located at the 2-position of the phenyl ring, $X^2$ is hydrogen, n is 0 in which the oxygen atom is bonded to position 3 of the lactam, and A is represented by ring (i) in which $R^2$ represents $C_1-C_6$ alkyl, typically dimethyl, located at position 4 of the pyrollidine ring;

viii) $X^1$ is trifluoromethyl and is located at the 2-position of the phenyl ring, $X^2$ is hydrogen, n is 0 in which the oxygen atom is bonded to position 3 of the lactam, and A is represented by ring (i) in which $R^2$ represents dimethyl located at position 4 of the pyrollidine ring and $R^1$ is represented by $C_1-C_6$ alkyl;

ix) $X^1$ is trifluoromethyl and is located at the 2-position of the phenyl ring, $X^2$ is hydrogen, n is 0 in which the oxygen atom is bonded to position 3 of the lactam, and A is represented by ring (i) in which $R^2$ represents dimethyl located at position 4 of the pyrollidine ring and $R^1$ is represented by optionally substituted benzyl;

x) $X^1$ is trifluoromethyl and is located at the 2-position of the phenyl ring, $X^2$ is hydrogen, n is 0 in which the oxygen atom is bonded to position 3 of the lactam, and A is represented by ring (i) in which $R^2$ represents dimethyl located at position 4 of the pyrrolidine ring and $R^1$ is represented by $SO_2—C_1-C_6$ alkyl, and;

xi) $X^1$ is trifluoromethyl and is located at the 2-position of the phenyl ring, $X^2$ is hydrogen, n is 0 in which the oxygen atom is bonded to position 3 of the lactam, and A is represented by ring (i) in which $R^2$ represents dimethyl located at position 4 of the pyrrolidine ring and $R^1$ is represented by $SO_2$-phenyl, in which the phenyl may be optionally substitute.

Synthesis

The compounds of Formula I can be prepared using methods known in the art for the preparation of ethers. The reader's attention is directed to European Patent Application Number 58932, published Sep. 1, 1982, for a generalized description of the preparation aryl ethers.

Scheme I below provides an overview of one such technique for preparing compounds in which A is represented by ring (i), i.e. a 2-oxopyrrolidinone.

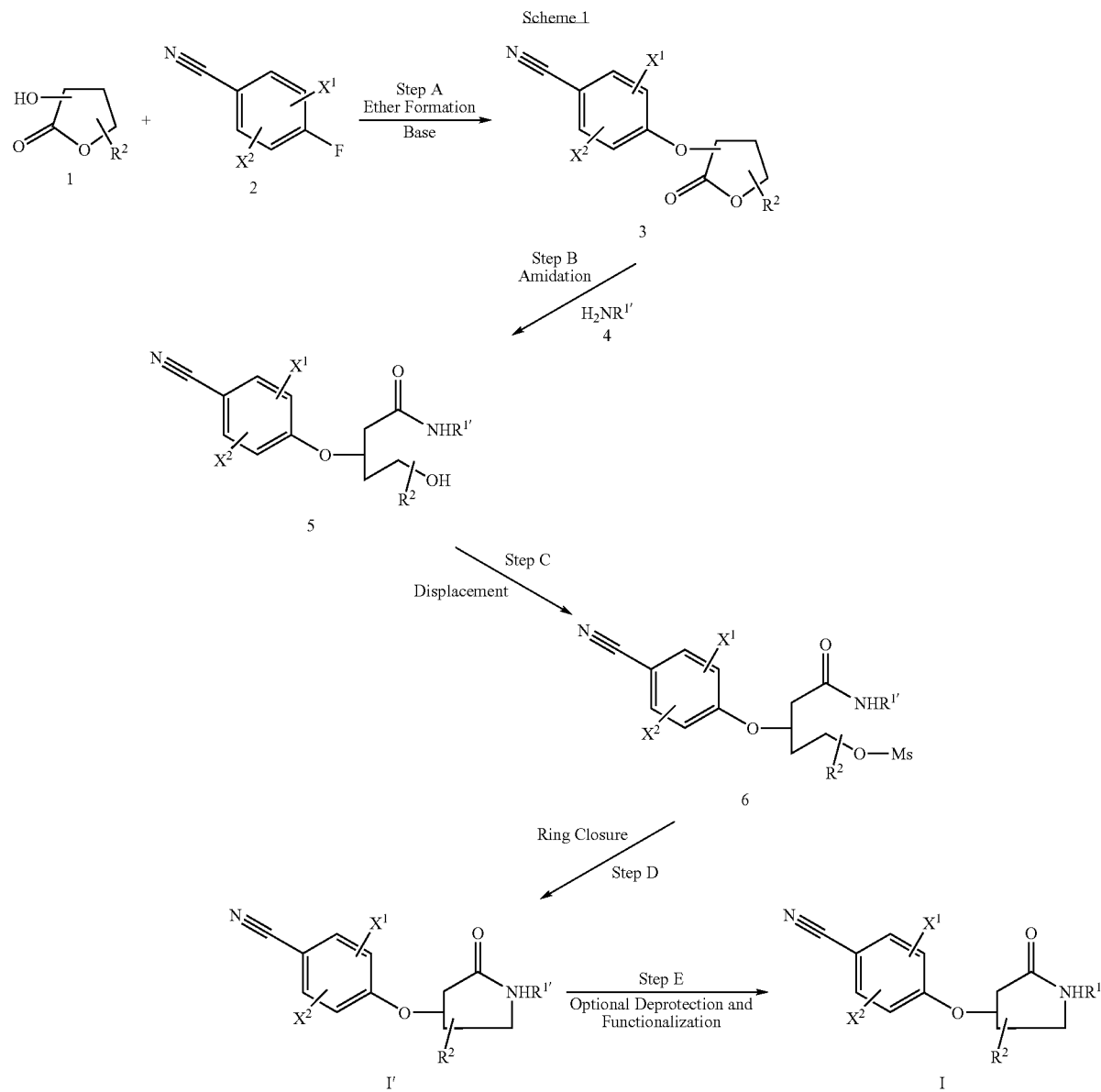

Scheme 1

As depicted above, one of the starting materials for Step A is an alcohol as depicted by structure 1. $R^2$ should be represented by the same substituent(s) as is 5 desired in the final product. Such lactones are known in the art. Many may be purchased from known commercial sources. Alternatively, they can be prepared as described in U.S. Patent Application Ser. No. 60/605,896 filed Aug. 31, 2004.

The other starting material for Step A is a 4-fluoro-benzonitrile as depicted by structure 2. $X^1$ and $X^2$ should each be represented by the same substituent as desired in the final product. These benzonitriles are known in the art and may be synthesized as described by Japanese Patent Application Number 01097937.

In Step A, the lactone of structure 3 is produced via a nucleophilic substitution as is known in the art. The alcohol of structure 1 is contacted with a slight excess of a base, such as sodium hydride, potassium t-butoxide, etc., to produce an alkoxide ion. The reaction is carried out in an aprotic solvent, such as tetrahydrofuran, under an inert atmosphere (typically nitrogen) at a temperature of about 0° C. The alcohol is stirred with the base for a period of time ranging from 5 to 60 minutes.

One equivalent of the 4-fluoro-benzonitrile of structure 2 is then added to the reaction medium and the reactants are stirred for a sufficient period of time to allow the alkoxide ion to displace the fluorine from the benzonitrile. This typically takes from 30 minutes to 24 hours. The reaction is typically allowed to warm to room temperature.

The resulting lactone depicted by structure 3 can be recovered by extraction, evaporation, or other techniques known in the art. It may optionally be purified by chromatography, recrystallization, distillation, or other techniques known in the art prior to carrying out the amidation depicted in Step B.

Alternatively, the etherification can be carried out using a weak base such as sodium hydroxide, potassium hydroxide, lithium hydroxide, magnesium hydroxide, sodium carbonate, potassium carbonate, cesium carbonate, potassium phosphate, sodium phosphate, potassium phosphonate, sodium phosphonate, sodium bicarbonate, etc. Reactions with weak bases are typically carried out under hydrous conditions (i.e. an admixture of water and an organic solvent such as dimethylformamide, tetrahydrofuran, etc.). The 4-fluoro-benzonitrile of structure 2 and the alcohol of structure of 1 are contacted in the presence of the base at a temperature ranging from room temperature to reflux.

In Step B, the lactone of structure 3 is contacted with an amine as depicted by structure 4, cleaving the lactone ring, resulting in the generation of an amide as depicted by structure 5. In the amine, $R^1$ may be represented by the same substituent as is desired in the final product. Alternatively, it may be represented by a protecting group such as 2,4-dimethoxy-benzyl, etc. One skilled in the art can readily determine whether it is ultimately more efficient to incorporate the desired $R^1$ moiety into the molecule in Step B or optional Step E.

The amidation of Step B is carried out using techniques known in the art. An excess of the amine of structure 4 is contacted with the lactone of structure 3 at ambient temperatures in a solvent such as tetrahydrofuran, methanol, etc. The reactants are stirred under a nitrogen atmosphere until the reaction is completed (i.e. from 1 hour to one week).

The resulting amide of structure 5 can be recovered by extraction, evaporation, or other techniques known in the art. It may optionally be purified by chromatography, recrystallization, distillation, or other techniques known in the art, prior to carrying out the displacement reaction depicted in Step C In Step C, the hydrogen atom of the hydroxyl function is displaced with a leaving group, such as a mesylate anion. Such displacement reactions are well known. For example, an excess of methanesulfonlyl chloride is contacted with the amide produced in Step C, at reduced temperatures (0° C.) in the presence of a base, such as pyridine. The reactants are typically stirred at reduced temperatures to allow the reaction to proceed to completion, generating the mesylate of structure 6. The resulting mesylate may be recovered by extraction, evaporation, or other techniques known in the art. It may optionally be purified by chromatography, recrystallization, distillation, or other techniques known in the art prior.

In Step D, the O-mesylated amide of structure 6 is subjected to a ring closure reaction thereby producing the lactam of structure I'. The ring closure may be carried out as is known in the art. The O-mesylated amide of structure 6 is contacted with an excess of a strong base, such as sodium hydride, in an aprotic solvent, such as tetrahydrofuran. The reactants are typically stirred at room temperature to allow the reaction to proceed to completion. The resulting lactam may be recovered by extraction, evaporation, or other techniques known in the art. It may optionally be purified by chromatography, recrystallization, distillation, or other techniques known in the art prior.

Alternatively, the ring closure can be carried out using a weak base such as sodium hydroxide, potassium hydroxide, lithium hydroxide, magnesium hydroxide, sodium carbonate, potassium carbonate, cesium carbonate, potassium phosphate, sodium phosphate, potassium phosphonate, sodium phosphonate, sodium bicarbonate, etc. Reactions with weak bases are typically carried out under hydrous conditions (i.e. an admixture of water and an organic solvent such as dimethylformamide, tetrahydrofuran, etc.). The O-mesylated amide of structure 6 is contacted with the base at a temperature ranging from room temperature to reflux.

Depending upon the substituent that $R^1$ is to represent in the final product, it may be necessary to carry out the deprotection/functionalization reaction depicted in Step E. This reaction will place the desired functional group onto the nitrogen atom of the lactam (i.e. $R^1$.) One skilled in the art can readily determine whether it is more expedious to introduce the desired $R^1$ substituent into the molecule during Step B or Step E.

The deprotection reaction will vary depending upon the identity of the protecting group. For example, if a benzyl protecting group is utilized, it may be removed by contacting it with trifluoracetic acid and triethylsilane under heat. Other protecting groups may be used. The reader's attention is directed to T. W. Greene, *Protective Groups in Organic Synthesis*, John Wiley & Sons, New York, 1991 for a further discussion of potential protecting groups and their removal.

The desired $R^1$ may be placed on the nitrogen atom of the lactam using synthetic techniques well known in the art. For example, if $R^1$ is a sulfonamide, it will typically be added in Step E. This sulfonamidation may be carried out as is known in the art. For example, the deprotected lactam of structure I' is contacted with an excess of a strong base such as sodium hydride at room temperature. An excess of the appropriate sulfonyl chloride is then added to the reaction mixture and stirred until complete. The desired compound of formula I may then be recovered by evaporation, extraction, etc. as is known in the art. It may optionally be purified by chromatography, recrystallization, distillation, or other techniques known in the art prior. Alternatively, bases such as lithium bis(trimethylsilyl) amide, which is also referred to as lithium hexamethyl disilyl amide ("LiHMDS" may be used.

Likewise an acyl linkage may be added in step E. This amidation may be carried out as is known in the art. For example, the deprotected lactam of structure I' is contacted with an excess of a strong base such as sodium hydride at room temperature. An excess of the appropriate acid chloride is then added to the reaction mixture and stirred until complete. The desired compound of formula I may then be recovered by evaporation, extraction, etc. as is known in the art. It may optionally be purified by chromatography, recrystallization, distillation, or other techniques known in the art prior.

An alkyl linkage may also be added in Step E. This alkyl linkage may be an alkyl group, an arylalkyl group, a heterocyclicalkyl group, a heteroarylalkyl group, a cycloalkylalkyl group, etc. The deprotected lactam of structure I' is contacted with an excess of a strong base, such as sodium hydride, at room temperature. An excess of the appropriate haloalkyl moiety is then added to the reaction mixture and stirred until complete. The desired compound of formula I may then be recovered by evaporation, extraction, etc. as is known in the art. It may optionally be purified by chromatography, recrystallization, distillation, or other techniques known in the art prior. Alternative $R^1$ moieties may be placed on the nitrogen of the lactam, using synthetic procedures analogous to those described above and well known in the art.

The reaction scheme described above applies equally to those compounds in which A is represented by ring (ii), i.e. a 2-oxo-piperidine. The only modification required pertains to one of the starting materials utilized in Step A. A 2-oxo-pyran as depicted below by structure 1' is substituted in place of the 2-oxo-furan depicted above as structure 1. After this substitution, Steps B-E may be carried out in the same manner as described above.

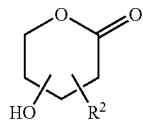

As would be appreciated by those skilled in the art, some of the methods useful for the preparation of such compounds, as discussed above, may require protection of a particular functionality, e.g., to prevent interference by such functionality in reactions at other sites within the molecule or to preserve the integrity of such functionality. The need for, and type of, such protection is readily determined by one skilled in the art, and will vary depending on, for example, the nature of the functionality and the conditions of the selected preparation method. See, e.g., T. W. Greene, supra.

Some of the compounds of this invention are acidic and they form salts with pharmaceutically acceptable cations. Some of the compounds of this invention are basic and form salts with pharmaceutically acceptable anions. All such salts are within the scope of this invention and they can be prepared by conventional methods such as combining the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. The compounds are obtained in crystalline form according to procedures known in the art, such as by dissolution in an appropriate solvent(s) such as ethanol, hexanes or water/ethanol mixtures.

Medical and Cosmetic Uses

The compounds of Formula I are androgen receptor modulators. They can be used to alleviate conditions associated with inappropriate activation of the androgen receptor. Compounds acting as androgen antagonists may be used to treat, or alleviate, hormone dependent cancers such as prostate carcinomas, benign hyperplasia of the prostate, acne, hirsutism, excess sebum, alopecia, hypertrichosis, precocious puberty, prostamegaly, virilization, and polycystic ovary syndrome. Compounds acting as partial agonists, or full agonists, may be used to treat, or alleviate, male hypogonadism, male sexual dysfunction (impotence, male dysspemtatogenic sterility), abnormal sex differentiation (male hermaphroditism), male delayed puberty, male infertility, aplastic anemia, hemolytic anemia, sickle cell anemia, idiopathic thrombocytopenic purpura, myelofibrosis, renal anemia, wasting diseases (post operative, malignant tumor, trauma, chronic renal disease, burn or AIDS induced), abatement of pain in terminal carcinoma of female genitalia, inoperable breast cancer, mastopathy, endometriosis, female sexual dysfunction, osteoporosis, wound healing and muscle tissue repair.

In order to exhibit the therapeutic properties described above, the compounds need to be administered in a quantity sufficient to modulate activation of the androgen receptor. This amount can vary depending upon the particular disease/condition being treated, the severity of the patient's disease/condition, the patient, the particular compound being administered, the route of administration, and the presence of other underlying disease states within the patient, etc. When administered systemically, the compounds typically exhibit their effect at a dosage range of from about 0.1 mg/kg/day to about 100 mg/kg/day for any of the diseases or conditions listed above. Repetitive daily administration may be desirable and will vary according to the conditions outlined above.

The compounds of the present invention may be administered by a variety of routes. They may be administered orally. The compounds may also be administered parenterally (i.e., subcutaneously, intravenously, intramuscularly, intraperitoneally, or intrathecally), rectally, or topically.

In a typical embodiment, the compounds are administered topically. Topical administration is especially appropriate for hirsutism, alopecia, acne and excess sebum. The dose will vary, but as a general guideline, the compound will be present in a dermatologically acceptable carrier in an amount of from about 0.01 to 50 w/w %, and more typically from about 0.1 to 10 w/w %. The dermatological preparation will be applied to the affected area from 1 to 4 times daily. "Dermatologically acceptable" refers to a carrier which may be applied to the skin or hair, and which will allow the drug to diffuse to the site of action. More specifically, it refers the site where inhibition of activation of an androgen receptor is desired.

In a further embodiment, the compounds are used topically to relieve alopecia, especially androgenic alopecia. Androgens have a profound effect on both hair growth and hair loss. In most body sites, such as the beard and pubic skin, androgens stimulate hair growth by prolonging the growth phase of the hair cycle (anagen) and increasing follicle size. Hair growth on the scalp does not require androgens but, paradoxically, androgens are necessary for balding on the scalp in genetically predisposed individuals (androgenic alopecia) where there is a progressive decline in the duration of anagen and in hair follicle size. Androgenic alopecia is also common in women where it usually presents as a diffuse hair loss rather than showing the patterning seen in men.

While the compounds will most typically be used to alleviate androgenic alopecia, the invention is not limited to this specific condition. The compounds may be used to alleviate any type of alopecia. Examples of non-androgenic alopecia include alopecia areata, alopecia due to radiotherapy or chemotherapy, scarring alopecia, stress related alopecia, etc. As used in this application, "alopecia" refers to partial or complete hair loss on the scalp.

Thus, the compounds can be applied topically to the scalp and hair to prevent, or alleviate balding. Further, the compound can be applied topically in order to induce or promote the growth of hair on the scalp.

In a further embodiment of the invention, a compound of Formula I is applied topically in order to prevent the growth of hair in areas where such hair growth is not desired. One such use will be to alleviate hirsutism. Hirsutism is excessive hair growth in areas that typically do not have hair (i.e. a female face). Such inappropriate hair growth occurs most commonly in women and is frequently seen at menopause. The topical administration of the compounds will alleviate this condition leading to a reduction, or elimination of this inappropriate, or undesired, hair growth.

The compounds may also be used topically to decrease sebum production. Sebum is composed of triglycerides, wax esters, fatty acids, sterol esters and squalene. Sebum is produced in the acinar cells of the sebaceous glands and accumulates as these cells age. At maturation, the acinar cells lyse, releasing sebum into the lumenal duct so that it may be deposited on the surface of the skin.

In some individuals, an excessive quantity of sebum is secreted onto the skin. This can have a number of adverse consequences. It can exacerbate acne, since sebum is the primary food source for *Propionbacterium acnes*, the causative agent of acne. It can cause the skin to have a greasy appearance, typically considered cosmetically unappealing.

Formation of sebum is regulated by growth factors and a variety of hormones including androgen. The cellular and molecular mechanism by which androgens exert their influence on the sebaceous gland has not been fully elucidated. However, clinical experience documents the impact androgens have on sebum production. Sebum production is significantly increased during puberty, when androgen levels are at their highest. Anti-androgens, such as finasteride, have been shown to decrease androgen secretion. For additional information on sebum production and androgens role in skin metabolism, see Moshell et al, Progress in Dermatology, vol. 37, No. 4, December 2003.

Thus, the compounds of formula I inhibit the secretion of sebum and thus reduce the amount of sebum on the surface of the skin. The compounds can be used to treat a variety of dermal diseases such as acne or seborrheic dermatitis.

In addition to treating diseases associated with excess sebum production, the compounds can also be used to achieve a cosmetic effect. Some consumers believe that they are afflicted with overactive sebaceous glands. They feel that their skin is oily and thus unattractive. These individuals can utilize the compounds of Formula I to decrease the amount of sebum on their skin. Decreasing the secretion of sebum will alleviate oily skin in individuals afflicted with such conditions.

The compounds may also be used to treat sebaceous hyperplasia. Sebaceous hyperplasia is the term used for enlarged sebaceous glands seen on the skin of the middle-aged and elderly. Most typically they occur on the forehead or cheeks. While these enlarged glands are not harmful, many individuals feel that they are cosmetically unattractive. Isotretinoin, which reduces sebum secretion, has been shown to reduce the size of these enlarged glands. Thus, by reducing sebum secretion, these compounds will also alleviate sebaceous hyperplasia.

In a further embodiment, those compounds acting as partial agonists, or full agonists, may be used to treat, or alleviate, osteoporosis. Osteoporosis is characterized by bone loss, resulting from an imbalance between bone resorption (destruction) and bone formation, which starts in the fourth decade and continues throughout life at the rate of about 1-4% per year (Eastell, Treatment of postmenopausal osteoporosis, *New Eng. J. Med.* 338: 736,1998). In the United States, there are currently about 20 million people with detectable fractures of the vertebrae due to osteoporosis. In addition, there are about 250,000 hip fractures per year due to osteoporosis, associated with a 12%-20% mortality rate within the first two years, while 30% of patients require nursing home care after the fracture and many never become fully ambulatory again. In postmenopausal women, estrogen deficiency leads to increased bone resorption resulting in bone loss in the vertebrae of around 5% per year, immediately following menopause. Thus, first line treatment/prevention of this condition is inhibition of bone resorption by bisphosphonates, estrogens, selective estrogen receptor modulators (SERMs) and calcitonin. However, inhibitors of bone resorption are not sufficient to restore bone mass for patients who have already lost a significant amount of bone. The increase in spinal BMD attained by bisphosphonate treatment can reach 11% after 7 years of treatment with alendronate. In addition, as the rate of bone turnover differs from site to site; higher in the trabecular bone of the vertebrae than in the cortex of the long bones, the bone resorption inhibitors are less effective in increasing hip BMD and preventing hip fracture. Therefore, osteoanabolic agents, which increase cortical/periosteal bone formation and bone mass of long bones, would address an unmet need in the treatment of osteoporosis especially for patients with high risk of hip fractures.

A number of studies demonstrate that androgens are osteoanabolic in women and men. Anabolic steroids, such as nandrolone decanoate or stanozolol, have been shown to increase bone mass in postmenopausal women. Beneficial effects of androgens on bone in post-menopausal osteoporosis are well documented in recent studies using combined testosterone and estrogen administration (Hofbauer, et al., Androgen effects on bone metabolism: recent progress and controversies, *Eur. J. Endocrinol.* 140, 271-286, 1999). Thus those compounds of Formula I exhibiting agonist or partial agonist activity may be used to treat, or alleviate, osteoporosis, including primary osteoporosis such as senile, postmenopausal and juvenile osteoporosis, as well as secondary osteoporosis, such as osteoporosis due to hyperthyroidism or Cushing syndrome (due to corticosteroid treatment), acromegaly, hypogonadism, dysosteogenesis and hypophosphatasemia. Other bone related indications amendable to treat from androgen agonists include osteoporotic fracture, childhood idiopathic bone loss, alveolar bone loss, mandibular bone loss, bone fracture, osteotomy, periodontitis, or prosthetic ingrowth.

Those compounds acting as agonists, or partial agonists, can also be used to stimulate muscle mass in patients afflicted with wasting diseases, such as AIDS, cancer cachexia, burns, renal disease, etc. Patients suffering from trauma, bedsores, age, etc. can also benefits from the anabolic effects of androgens.

Co-Administration

In a further embodiment of the invention, the compounds of Formula I can be co-administered with other compounds to further enhance their activity, or to minimize potential side effects. For example, potassium channel openers, such as minoxidil, are known to stimulate hair growth and to induce anagen. Examples of other potassium channel openers include (3S,4R)-3,4-dihydro-4-(2,3-dihydro-2-methyl-3-oxopyridazin-6-yl)oxy-3-hydroxy-6-(3-hydroxyphenyl)sulphonyl-2,2,3-trimethyl-2H-benzo[b]pyran, diaxozide, and P1075 which is under development by Leo Pharmaceuticals. Such compounds can be co-administered with the compounds of Formula I to alleviate alopecia.

Thyroid hormone is also known to stimulate hair growth. Synthetic thyroid hormone replacements (i.e., thyromimetics) have also been shown to stimulate hair growth. Such thyromimetics have been described in the literature previously. The reader's attention is directed to European Patent Application No. 1262177, the contents of which are hereby incorporated by reference, for a discussion of such compounds and their use to alleviate alopecia. One particular compound of interest is 2-{4-[3-(4-Fluoro-benzyl)-4-hydroxy-phenoxy]-3,5-dimethyl-phenyl}-2H-[1,2,4]triazine-3,5-dione. Such compounds can be co-administered with the compounds of Formula I to alleviate alopecia.

Anti-androgens can work by a number of different mechanisms. For example, some compounds block the conversion of testosterone to 5-α-dihydrotestosterone, which is responsible for the biological effect in many tissues. 5-Alpha-reductase inhibitors, such as finasteride, have been shown to stimulate hair growth and to decrease sebum production. Finasteride is commercially available from Merck under the trade name Propecia®. Examples of other 5-α-reductase inhibitors include dutasteride (Glaxo Smithkline). Such compounds can be co-administered with the compounds of Formula I to alleviate alopecia and/or to decrease sebum production.

Protein kinase C inhibitors have also been shown to stimulate hair growth and induce anagen. Calphostin C, which is a selective inhibitor of protein kinase C, has been shown to induce anagen. Other selective protein kinase C inhibitors, such as hexadecylphosphocholine, palmitoyl-DL-carnitine chloride, and polymyxin B sulfate have also been shown to induce anagen. [Skin Pharmacol Appl Skin Physiol 2000 May-August; 13(3-4):133-42]. Any such protein kinase C inhibitor can be co-administered with a compound of Formula I to alleviate alopecia.

Immunophilins are a family of cytoplasmic proteins. Their ligands include cyclosporin and FK506. They are derived from fungi and were developed primarily for their potent immunosuppressive properties. Cyclosporin binds to the proteins, cyclophilins, while FK506 binds to FK binding proteins (FKBPs). All of these compounds have been shown to stimulate hair growth and induce anagen. Any such immunophilin ligands can be co-administered with a compound of Formula I to alleviate alopecia.

Acyl CoA cholesterol acyl transferase (ACAT) inhibitors were initially evaluated for the treatment of elevated serum cholesterol. It was subsequently discovered that these compounds decrease sebum production (U.S. Pat. No. 6,133,326). Any such ACAT inhibitor can be co-administered with a compound of formula I to decrease sebum production, alleviate oily skin, etc.

Antibiotics, such as tetracycline and clindamycin, have been used to alleviate acne. The antibiotic eradicates the microorganism, *Propionbacterium acnes*, leading to a reduction in the patient's acne. The compounds of Formula I can be co-administered with any antibiotic suitable for the treatment of acne.

Retinoids, such as isotretinoin, have been shown to decrease sebum production and are used to treat acne. These retinoids can be co-administered with a compound of Formula I in order to decrease sebum production and/or to treat acne.

Estrogen and progesterone have each been shown to decrease sebum production. These compounds, or any synthetic agonist of such compounds, may be co-administered with a compound of formula I in order to decrease sebum production.

As used in this application, co-administered refers to administering a compound of Formula I with a second medicinal, typically having a differing mechanism of action, using a dosing regimen that promotes the desired result. This can refer to simultaneous dosing, dosing at different times during a single day, or even dosing on different days. The compounds can be administered separately or can be combined into a single formulation. Techniques for preparing such formulations are described below.

Formulations

If desired, the compounds can be administered directly without any carrier. However, to ease administration, they will typically be formulated into pharmaceutical carriers. Likewise, they will most typically be formulated into dermatological, or cosmetic carriers. In this application the terms "dermatological carrier" and "cosmetic" carrier are being used interchangeably. They refer to formulations designed for administration directly to the skin or hair.

Pharmaceutical and cosmetic compositions can be manufactured utilizing techniques known in the art. Typically an effective amount of the compound will be admixed with a pharmaceutically/cosmetically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent, which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

The compounds of this invention will typically be administered topically. As used herein, topical refers to application of the compounds (and optional carrier) directly to the skin and/or hair. The topical composition according to the present invention can be in the form of solutions, lotions, salves, creams, ointments, liposomes, sprays, gels, foams, roller sticks, or any other formulation routinely used in dermatology.

Thus, a further embodiment relates to cosmetic or pharmaceutical compositions, in particular dermatological compositions, which comprise at least one of the compounds corresponding to Formula I above. Such dermatological compositions will contain from 0.001% to 10% w/w % of the compounds in admixture with a dermatologically acceptable carrier, and more typically, from 0.1 to 5 w/w % of the compounds. Such compositions will typically be applied from 1 to 4 times daily. The reader's attention is directed to *Remington's Pharmaceutical Science*, Edition 17, Mack Publishing Co., Easton, Pa. for a discussion of how to prepare such formulations.

The compositions according to the invention can also consist of solid preparations constituting cleansing soaps or bars. These compositions are prepared according to the usual methods.

The compounds can also be used for the hair in the form of aqueous, alcoholic or aqueous-alcoholic solutions, or in the form of creams, gels, emulsions or mousses, or alternatively in the form of aerosol compositions also comprising a propellant under pressure. The composition according to the invention can also be a hair care composition, and in particular a shampoo, a hair-setting lotion, a treating lotion, a styling cream or gel, a dye composition, a lotion or gel for preventing hair loss, etc. The amounts of the various constituents in the dermatological compositions according to the invention are those conventionally used in the fields considered.

The medicinal and cosmetics containing the compounds of the invention will typically be packaged for retail distribution (i.e. an article of manufacture). Such articles will be labeled and packaged in a manner to instruct the patient how to use the product. Such instructions will include the condition to be treated, duration of treatment, dosing schedule, etc.

The compounds of Formula I may also be admixed with any inert carrier and utilized in laboratory assays in order to determine the concentration of the compounds within the serum, urine, etc., of the patient as is known in the art. The compounds may also be used as a research tool.

Use in Livestock

In addition to the therapeutic and cosmetic uses described above, the compounds may also be used to promote the growth of animals, especially livestock. The compounds will increase the rate at which the animals gain weight, increase the leanness of the resulting meat and improve the efficiency of feed utilization. This may be accomplished by administering an effective amount of a compound of Formula I to an animal receiving adequate nutrition to support growth (i.e. sufficient calories, amino acids, vitamins, minerals, essential fats, etc).

To simplify administration, the compound is typically mixed with animal feeds or prepared in the form of an animal-feed premix, concentrate, or supplement which can be blended with animal feeds. Regardless of the procedure selected, the compound will typically be present at levels of from about 0.05 to 500 ppm in the feed.

Animal-feed premixes, supplements or concentrates can be prepared by mixing on a weight basis about 0.5 to 50% of a compound with about 50 to 99.5% of an edible diluent. Diluents suitable for use in the manufacture of animal-feed supplements, concentrates, and premixes include the following: corn meal, soybean meal, bone meal, alfalfa meal, cottonseed oil meal, urea, molasses, and other similar materials. Use of the diluents in feed supplements, concentrates, and premixes improves uniformity of distribution of the active ingredient in the finished feed.

Feeds for swine, cattle, sheep, fish, and goats typically contains about 0.05 to 400 grams of active ingredient per ton of feed. Poultry and domestic-pet feeds range from about 0.05 to 400 grams per ton of feed.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention. The following examples and biological data are being presented in order to further illustrate the invention. This disclosure should not be construed as limiting the invention in any manner.

EXAMPLES

General analytical methods used in Examples 1, 3-27, and 68-135 include:

1) Mass spectroscopy:
    MS Conditions: Combi RP3 50×4.6 mm column, 45° C., gradient in 3.5 min, hold 0.5 min 2) High performance liquid chromatography
    HPLC conditions: Supelco Discovery C18, 250×4.6 mm, Flow rate=1.5 mL/min, 80/20 to 10/90 $H_2O$+0.1% TFA/ACN+0.1% TFA over 20 min, hold 5 min 3) Optical rotation:
    Conditions: Wavelength: 589 nm, Temp: 24.6° C., Solvent: $CHCl_3$ 4) Melting point—determined on a capillary melting point apparatus (either Thomas Hoover or Mel-Temp).

5) Liquid chromatographic mass spectroscopy "LCMS"—
    Mobile phase: 50-2% $H_2O$ in 3.5 min, hold 0.5 min, run time 4 min; stationary phase: Phenomenex Develosil Combi RP3 50×4.6 mm Column; 45° C. (unless indicated otherwise).

Example 1

Example 1 illustrates one of the synthetic routes described above in Reaction Scheme I. It specifically describes attaching the desired $R^1$ moiety in the amidation reaction (i.e. Step B). This example also illustrates the preparation of (3R,S)-(+)-4-(1-sec-Butyl-4,4-dimethyl-2-oxo-pyrrolidin-3-yloxy)-2-trifluoromethyl-benzonitrile.

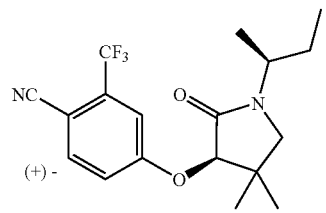

Step A: Ether Formation

Preparation of (±)-4-(4,4-dimethyl-2-oxo-tetrahydrofuran-3-yloxy)-2-trifluoromethyl-benzonitrile

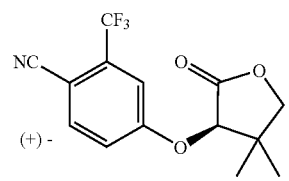

To a stirring solution comprised of (R)-(−)-pantolactone (46.1 g; 354 mmol) in tetrahydrofuran (500 mL) at -15° C. under a nitrogen atmosphere is added a suspension comprised of a 60% sodium hydride mineral oil dispersion (14 g; 340 mmol) in tetrahydrofuran (70 mL) over a one hour period. Another portion of tetrahydrofuran (100 mL) is added to the reaction mixture to aid in more vigorous stirring of the thick mixture. Upon the completion of hydrogen gas liberation, a solution comprised of 4-fluoro-2-trifluoromethylbenzonitrile (68.9 g; 364 mmol) is added. The reaction mixture is allowed to warm slowly to ambient temperature overnight. The reaction mixture is neutralized with saturated aqueous ammonium chloride. The mixture is extracted with ethyl acetate (350 mL) and the layers are separated. The organic layer is washed with a brine solution and is dried over anhydrous magnesium sulfate. The solution is concentrated in vacuo to afford 102.57 g of an off-white solid. The solid is recrystallized from absolute ethanol to afford 73.3 g of a fine white crystalline solid; 70.6% yield; $^1$H-NMR (400 MHz; $CDCl_3$) δ7.78 (dd, 1H, J=8.6, 0.4 Hz), 7.43 (d, 1H, J=2.5 Hz), 7.31 (dd, 1H, J=8.6, 2.7 Hz), 4.67 (s, 3H), 4.17 (d, 1H, J=9.0 Hz), 4.10 (d, 1H, J=9.0 Hz), 1.29 (s, 6H); $^{19}$F-NMR (376 MHz; $CDCl_3$) δ −62.70 (s, 3F).

Step B: Amidation

Preparation of N-sec-butyl-2-(4-cyano-3-trifluoromethyl-phenoxy)-4-hydroxy-3,3-dimethyl-butyramide

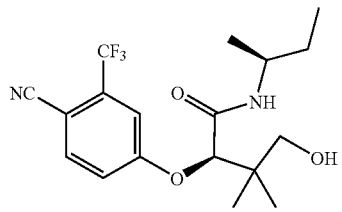

To a stirring solution comprised of (+)-4-(4,4-dimethyl-2-oxo-tetrahydro-furan-3-yloxy)-2-trifluoromethyl-benzonitrile (1.345 g; 4.495 mmol) in tetrahydrofuran (5 mL) at ambient temperature under a nitrogen atmosphere is added (S)-(+)-sec-butylamine (0.4931 g; 6.742 mmol.) The reaction mixture is stirred for eight days. The reaction mixture is diluted with ethyl acetate and washed with 1N aqueous hydrochloric acid and with a brine solution. The organic phase is dried over anhydrous magnesium sulfate and is concentrated in vacuo to afford 1.633 of a white solid as a mixture of diastereomers; HPLC UV purity: 94% (two diastereomers.)

Step C: Displacement

Preparation of methanesulfonic acid 3-sec-butylcarbamoyl-3-(4-cyano-3-trifluoromethyl-phenoxy)-2,2-dimethyl-propyl ester

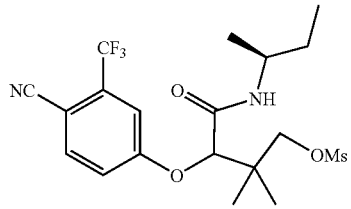

To a stirring solution comprised of two(2) N-sec-butyl-2-(4-cyano-3-trifluoromethyl-phenoxy)-4-hydroxy-3,3-dimethyl-butyramide diastereomers (1.63 g; 4.38 mmol) in pyridine (10 mL) at 0° C. under a nitrogen atmosphere is added methanesulfonyl chloride (0.75 g; 6.5 mmol). The reaction mixture is stirred cold for 3.5 hours. The reaction mixture is diluted with dichloromethane and is washed with 1N aqueous hydrochloric acid and with brine. The organic phase is dried over anhydrous magnesium sulfate and is concentrated in vacuo (the water bath temperature is not raised above 23° C.) to afford 1.892 g of a foam; HPLC UV purity: 99.3% (two diastereomers.)

Step D: Ring Closure

Preparation of (3R,S)-(+)-4-(1-sec-Butyl-4,4-dimethyl-2-oxo-pyrrolidin-3-yloxy)-2-trifluoromethyl-benzonitrile

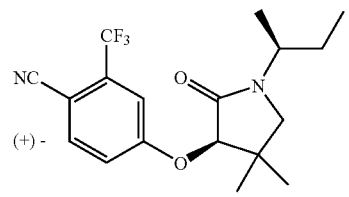

To a stirring solution comprised of a mixture of methanesulfonic acid 3-sec-butylcarbamoyl-3-(4-cyano-3-trifluoromethyl-phenoxy)-2,2-dimethyl-propyl ester diastereomers (1.89 g; 4.2 mmol) in tetrahydrofuran (10 mL) at ambient temperature under a nitrogen atmosphere is added a 60% sodium hydride mineral oil dispersion (0.34 g; 8.4 mmol) in portions. The reaction mixture is stirred overnight. The reaction mixture is carefully neutralized with saturated aqueous ammonium chloride and is extracted with ethyl acetate. The organic phase is washed with a brine solution and is dried over anhydrous magnesium sulfate. The organic solution is concentrated in vacuo to afford 1.47 g of a viscous residue comprised of two diastereomers; HPLC UV purity: 92% (two diastereomers.) The diastereomers are separated by flash silica column chromatography (Biotage Horizon chromatography system; 100 g of silica gel, Biotage 40+M silica cartridge.) Elution with a gradient (100% hexanes to 30% ethyl acetate over 3204 mL) will afford complete separation of the diastereomers: (3R,S)-(+)-4-(1-sec-Butyl-4,4-dimethyl-2-oxo-pyrrolidin-3-yloxy)-2-trifluoromethyl-benzonitrile. 0.365 g;; $[\alpha]_{589} 24°$ C.=+238° (in dichloromethane);microanalysis for $C_{18}H_{21}F_3N_2O_2$: % C(calc/found) 61.01/60.81, % H 5.97/6.06, % N 7.91/7.66, % F 16.08/16.25.

Example 2

This example also illustrates the preparation of (3R,S)-(+)-4-(1-sec-Butyl-4,4-dimethyl-2-oxo-pyrrolidin-3-yloxy)-2-trifluoromethylbenzonitrile, the product of Example 1.

Step A: Ether Formation

Preparation of (±)-4-(4,4-dimethyl-2-oxo-tetrahydro-furan-3-yloxy)-2-trifluoromethyl-benzonitrile Solid NaH (60 wt % dispersion in mineral oil, 13.80 g, 345 mmol) was added portionwise over 35 min to a cold (0-5° C.) sol'n of (+/−)-pantolactone, (42.90 g, 330 mmol) in 600 mL dry tetrahydrofuran ("THF") under an $N_2$ atmosphere. After stirring at 0-5° C. for 2 hours ("h") 4-fluoro-2-trifluoromethylbenzonitrile (56.73 g, 300 mmol) was added in one portion. The reaction mixture was allowed to slowly warm to 20-25° C. and then stirred at this temp for 16 h. The reaction mixture was then cooled to 5-10° C. and quenched with 500 mL sat'd aq. $NH_4Cl$. The phases were separated and the aqueous was extracted with methyl tertbutyl ether "MTBE" (2×400 mL). The organic was conc'd under vac (40-45° C.) to a "wet" beige solid. Ethanol (300 mL) was added and the slurry was conc'd under vac again to a "drier" beige solid. The solid was combined with 500 mL EtOH and heated to 70-75° C. The slightly turbid hot sol'n was filtered and the filtrate was allowed to cool to 20-25° C. (ppt'n occurred quickly) and was stirred 16 h. The slurry was cooled in an ice/water bath 2 h. The cold slurry was filtered and the solid was washed with 200 mL cold EtOH, followed by 200 mL Hept. Suction dried the white granular solid 2 h.

Step B: Amidation

Preparation of N-sec-butyl-2-(4-cyano-3-trifluoromethylphenoxy)-4-hydroxy-3,3-dimethyl-butyramide (±)-4-(4,4-Dimethyl-2-oxo-tetrahydrofuran-3-yloxy)-2-trifluoromethylbenzonitrile (66.00 g, 221 mmol) was combined with 330 mL dry THF and the (S)-(+)-2-butylamine (total of 64.5 g, 882 mmol), and the reaction mixture was heated at 40-60° C. in a sealed vessel for 124 h. The amber sol'n was concentrated under vac (35-40° C.) to an amber gum. The gum was redissolved in 500 m ethyl acetate "EtOAc" and conc'd again. The gum was redissolved in 500 mL "EtOAc" and passed through a pad of silica. The silica was washed with 500 mL EtOAc and the combined filtrate was concentrated under vac to a pale amber gum.

Step C: Displacement Reaction

Preparation of methanesulfonic acid 3-sec-butylcarbamoyl-3-(4-cyano-3-trifluoromethylphenoxy)-2,2-dimethylpropyl ester Methanesulfonyl chloride (36.45 g, 318 mmol) was added in one portion to a cold (0-5° C.) sol'n of the N-sec-butyl-2-(4-cyano-3-trifluoromethyl phenoxy)-4-hydroxy-3,3-dimethylbutyramide (5, 79.0 g, 212 mmol) in 200 mL pyridine. The reaction mixture was stirred at 0-5° C. for 5 h. The reaction was quenched with 800 mL sat'd aq. NH₄Cl and extracted with 1000 mL CH₂Cl₂. The organic phase was washed with 2N aq. HCl (3×300 mL) and then half sat'd aq. NaCl (3×300 mL). The organic was conc'd under vac (35-40° C.) to an amber gum.

Step D: Ring Closure

Preparation of (3R,S)-(+)-4-(1-sec-Butyl-4,4-dimethyl-2-oxo-pyrrolidin-3-yloxy)-2-trifluoromethyl-benzonitrile Solid NaH (60 wt % dispersion in mineral oil, 16.6 g, 416 mmol) was added portion wise over 25 min to a cold (0-5° C.) sol'n of methanesulfonic acid 3-sec-butylcarbamoyl-3-(4-cyano-3-trifluoromethylphenoxy)-2,2-dimethylpropyl ester (104 g, 208 mmol) in 400 mL dry THF under an N₂ atmosphere. The reaction mixture was allowed to warm to 20-25° C. and then stirred at this temp. for 90 h. The reaction mixture was quenched by adding it to 500 mL cold (5-10° C.) sat'd aq. NH₄Cl. The phases were separated and the aqueous was extracted with ethyl acetate ("EtOAc") (2×500 mL). The pale yellow organic was conc'd under vac (40-45° C.) to an orange-yellow oil/gum (83 g). The crude product was purified by extensive silica gel (230-400 mesh) column chromatography (EtOAc/Heptane) followed by crystallization (EtOAc/Heptane). The pure desired diastereomer was isolated as a white granular solid MS⁺: 355. m.p. 101-102° C. Optical rotation $[\alpha]_{589}^{25}$=+180.10(in methanol) Elemental analysis results: Obsv'd (Theor.): C, 61.03 (61.01); H, 6.02 (5.97); N, 7.88 (7.91); F, 15.98 (16.08). HPLC analysis: Chiral purity: 100%.

Example 3

Example 3 illustrates another of the synthetic routes described above in Reaction Scheme I. It specifically illustrates the deprotection reaction of Step E, generating a compound in which $R^1$ is hydrogen. Subsequent examples also demonstrate how the optional functionalization reaction of Step E may be carried out in order to place different functional groups on the nitrogen atom of the lactam (i.e. $R^1$) This example also demonstrate the preparation of (+)-4-(4,4-Dimethyl-2-oxo-pyrrolidin-3-yloxy)-2-trifluoromethyl-benzonitrile, whose structure is depicted below.

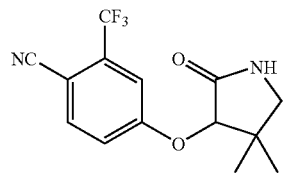

Step A. Ether formation

The preparation of (±)-4-(4,4-Dimethyl-2-oxo-tetrahydro-furan-3-yloxy)-2-trifluoromethyl-benzonitrile

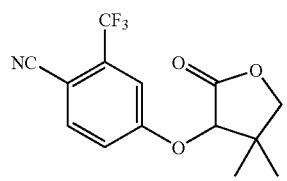

To a stirring solution comprised of (R)-(−)-pantolactone (44.7 g; 336 mmol) in tetrahydrofuran (625 mL) at 0° C. under a nitrogen atmosphere was added a 60% sodium hydride mineral oil dispersion (14.1 g; 352 mmol) directly in portions. Upon the completion of hydrogen gas liberation, 4-fluoro-2-trifluoromethylbenzonitrile solid (59.0 g; 312 mmol) was added directly. The reaction mixture was allowed to warm slowly to ambient temperature overnight. The reaction mixture was neutralized with saturated aqueous ammonium chloride (500 mL.) The mixture was extracted with ethyl acetate (800 mL) and the layers were separated. The organic layer was dried over anhydrous magnesium sulfate and was concentrated in vacuo to afford 99.83 g of a beige solid. The solid was recrystallized from absolute ethanol (300 mL) to afford 81.56 g of an off-white crystalline solid; ¹H-NMR (400 MHz; CDCl₃) δ7.78 (dd, 1H, J=8.6, 0.4 Hz), 7.43 (d, 1H, J=2.5 Hz), 7.31 (dd, 1H, J=8.6, 2.7 Hz), 4.67 (s, 3H), 4.17 (d, 1H, J=9.0 Hz), 4.10 (d, 1H, J=9.0 Hz), 1.29 (s, 6H); ¹⁹F-NMR (376 MHz; CDCl₃) δ −62.70 (s, 3F).

Step B: Amidation

The preparation of 2-(4-Cyano-3-trifluoromethyl-phenoxy)-N-(2,4-dimethoxy-benzyl)-4-hydroxy-3,3-dimethyl-butyramide

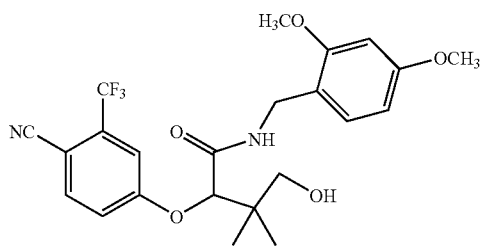

A suspension comprised of (±)-4-(4,4-dimethyl-2-oxo-tetrahydro-furan-3-yloxy)-2-trifluoromethyl-benzonitrile (81.55 g; 272.5 mmol), 2,4-dimethoxybenzylamine (50.40 g; 295.4 mmol), and methanol (300 mL) was stirred at ambient temperature under a nitrogen atmosphere overnight. The suspension became a clear solution. The reaction mixture was concentrated in vacuo to afford a cloudy orange oil (145 g.) The oil was triturated with diethyl ether (500 mL) over a steam bath to gentle boiling. The flask was removed from the steam bath as a solid began to slowly form. The oil was scratched with a spatula which accelerated solid formation and the solids were collected by vacuum filtration to afford 107.25 g of an off-white amorphous solid. The mother liquor was concentrated in vacuo to give 28.35 g of a crude red-brown oil. This oil was purified by flash silica column chromatography (Isco Fraction Collector with Biotage 65i 330 g silica cartridge.) Elution with a gradient (98:2 v/v hexanes-ethyl acetate to 100% ethyl acetate over 1 hour, 12 minutes, 18×150 mm tubes, each filled to 27 mL mark in 30 seconds) afforded 20 g of a light-yellow solid. The material was recrystallized from diethyl ether to afford 9.659 g of a white crystalline solid; $^1$H-NMR (400 MHz; CDCl$_3$) δ 7.61 (d, 1H, J=8.8 Hz), 7.24 (d, 1H, J=2.5 Hz), 7.07 (d, 1H, J=8.2 Hz), 6.94 (dd, 1H, J=8.8, 2.5 Hz), 6.58 (t, 1 H, J=5.6 Hz), 6.37 (dd, 1H, J=8.4, 2.5 Hz), 6.28 (d, 1H, J=2.4 Hz), 4.52 (s, 1H), 4.37-4.25 (m, 2H), 3.78 (s, 3H), 3.58 (s, 3H), 3.50 (d, 1H, J=11.7 Hz), 3.42 (d, 1H, J=11.7 Hz), 1.09 (s, 3H), 0.97 (s, 3H); $^{19}$F-NMR (376 MHz; CDCl$_3$) δ −62.70 (s, 3F); MS (APCI+) 467.3 (M+1,100); (APCI−) 465.2 (M−1, 14), 186.0 (100).

Step C: Displacement Reaction

Preparation of Methanesulfonic acid 3-(4-cyano-3-trifluoromethyl-phenoxy)-3-(2,4-dimethoxy-benzyl-carbamoyl)-2,2-dimethyl-propyl ester

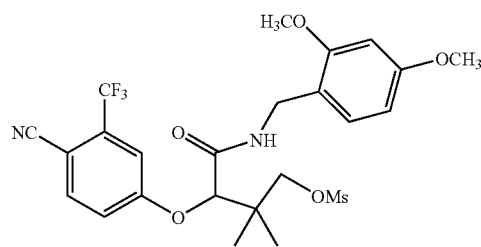

To a clear, colorless solution comprised of 2-(4-cyano-3-trifluoromethyl-phenoxy)-N-(2,4-dimethoxy-benzyl)-4-hydroxy-3,3-dimethyl-butyramide (116.42 g; 250 mmol) in pyridine (160 mL) cooled to 0° C. under a nitrogen atmosphere was added methanesulfonyl chloride (30.2 g; 262 mmol). The mixture turned cloudy yellow with precipitate within 5 minutes of methanesulfonyl chloride addition. The reaction mixture was stirred cold for 1 hour, 20 minutes. The reaction flask was then loaded onto the rotary evaporator over a water bath warmed to 40° C. and the high vacuum was applied. After two hours of rotation, a negligible volume of pyridine had been distilled off and the water bath temperature was raised to 54° C. The pyridine was distilled off as the solution turned to a darker orange color and yielded a dark orange oil. To avoid decomposition, the flask was removed and the contents were partitioned between dichloromethane (1500 mL) and 2N aqueous hydrochloric acid (500 mL.) The unseparated aqueous (top) layer was tested with pH paper to show a pH of 4. The aqueous phase was acidified to pH 0 by the addition of concentrated aqueous hydrochloric acid (10 mL) to the biphasic mixture. The layers were separated and the organic phase was dried over anhydrous magnesium sulfate and vacuum filtered. The vacuum flask containing the clear orange filtrate solution was covered and left at ambient temperature for three days. The solution turned to dark red. Thin layer chromatography analysis of this solution (solvent system: 1:1 v/v hexanes-ethyl acetate) showed the major presence of desired material along with a baseline (Rf=0) species and two higher R$_f$ species. The solution was concentrated in vacuo, keeping the water bath temperature at 35° C., to obtain 159 g of a red foam; 1H-NMR (400 MHz; CDCl$_3$) δ 7.59 (d, 1H, J=2.1 Hz), 7.23 (d, 1H, J=2.5 Hz), 7.05 (d, 1H, J=2.1 Hz), 6.93 (dd, 1H, J=2.2, 0.7 Hz), 6.50 (t, 1H, J=1.5 Hz), 6.36 (dd, 1H, J=2.1, 0.6 Hz), 6.26 (d, 1H, J=0.6 Hz), 5.28 (s, 1H), 4.45 (s, 1H), 4.36-4.24 (m, 2H), 4.11 (dd, 2H, J=6.7, 2.4 Hz), 3.77 (s, 3H), 3.57 (s, 3H), 2.99 (s, 3H), 1.13 (s, 3H), 1.12 (s, 3H); 19F-NMR (376 MHz; CDCl$_3$) δ −62.69 (s, 3F).

Step D: Ring Closure

Preparation of 4-[1-(2,4-Dimethoxy-benzyl)-4,4-dimethyl-2-oxo-pyrrolidin-3-yloxy]-2-trifluoromethyl-benzonitrile

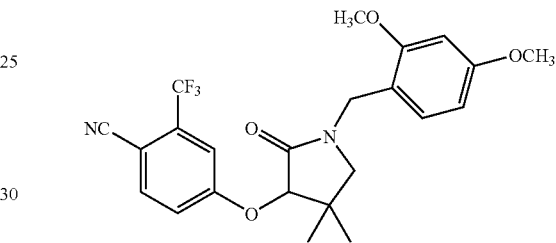

To a stirring solution comprised of methanesulfonic acid 3-(4-cyano-3-trifluoromethyl-phenoxy)-3-(2,4-dimethoxy-benzylcarbamoyl)-2,2-dimethyl-propyl ester (35 g; 64 mmol) in tetrahydrofuran (700 mL) at 0° C. under nitrogen was added the sodium hydride mineral oil dispersion (14.7 g; 366 mmol.) After liberation of hydrogen gas was mostly complete (reaction time ~5 minutes), the reaction mixture was analyzed by mass spectrometry to show presence of a product with the desired mass and presence of a species with the mass of the starting material. Another portion (8 g) of sodium hydride was added and the ice bath was removed and the reaction mixture was stirred for 15 minutes. The mixture was cooled with an ice bath and was slowly quenched with saturated aqueous ammonium chloride. To the mixture was added ethyl acetate and the biphasic mixture was stirred gently overnight. The layers were separated and the organic phase was dried with anhydrous magnesium sulfate and concentrated in vacuo to afford 35 g of a reddish viscous oil. The product was purified by flash chromatography (Biotage 65i 330-g silica cartridge on the Isco Foxy fraction collector). Elution with a gradient (100% hexanes to 50% ethyl acetate over 1 h, 48 min) afforded 30.1 g of a clear glass. The product was dissolved in boiling diethyl ether over a steam bath, and the clear solution was cooled in the refrigerator for four days. A brilliant white crystalline solid had formed from solution and was collected by vacuum filtration (15 g). The volume of the filtrate was reduced over the steam bath and the solution was cooled overnight after seeding with some crystals from the first crop. A second crop of white crystalline solid was obtained and collected by vacuum filtration. The crystals were combined with the first batch of crystals to afford 23.2 g of a white crystalline solid; 1H-NMR (400 MHz; CDCl$_3$) δ 7.73 (d, 1H, J=8.8 Hz), 7.49 (d, 1H, J=2.5 Hz), 7.42 (dd, 1H, J=8.6, 2.5 Hz), 7.14 (dd, 1H, J=6.2, 2.5 Hz), 6.45 (s, 1H), 6.44

(dd, 1H, J=6.6, 2.5 Hz), 4.52 (s, 1H), 4.44 (d, 1H, J=14.3 Hz), 4.40 (d, 1H, J=14.3 Hz), 3.80 (s, 3H), 3.79 (s, 3H), 3.06 (d, 1H, J=10.0 Hz), 3.01 (d, 1H, J=10.0 Hz), 1.16 (s, 3H), 1.11 (s, 3H); 19F-NMR (376 MHz; CDCl$_3$) δ −62.64 (s, 3F); MS (APCl+) 449.1 (M+1, 100); (APCl−) 186.0 (100) LCMS: 50-2% H$_2$O, 214 nm, 3.260 min, 100%

Step E: Deprotection Reaction

Preparation of 4-(4,4-Dimethyl-2-oxo-pyrrolidin-3-yloxy)-2-trifluoromethyl-benzonitrile

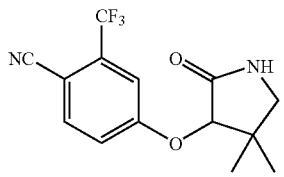

A solution of 4-[1-(2,4-dimethoxy-benzyl)-4,4-dimethyl-2-oxo-pyrrolidin-3-yloxy]-2-trifluoromethyl-benzonitrile (25 g; 56 mmol) in trifluoroacetic acid (250 mL) and triethylsilane (20 g; 169 mmol; 3 eq) was brought to gentle reflux overnight. The reaction was cooled to ambient temperature. The reaction mixture was concentrated in vacuo to give an oily residue. The crude product was dissolved in dichloromethane and was washed with saturated aqueous sodium bicarbonate and with brine solution. The organic phase was dried over anhydrous magnesium sulfate and concentrated in vacuo to give a dark purple oily residue. The product was purified by flash silica column chromatography. Elution with a gradient (100% hexanes to 3:2 v/v ethyl acetate-hexanes over 1 hour, 12 minutes; pump speed: 1 mL/min) afforded an off-white powder. Trituration with diethyl ether over a steam bath afforded 14.6 g of a white powder; 1H-NMR (400 MHz; CDCl$_3$) δ 7.75 (dd, 1H, J=8.6, 0.4 Hz), 7.46 (d, 1H, J=2.5 Hz), 7.37 (dd, 1H, J=8.6, 2.5 Hz), 6.46 (s, 1H), 4.53 (s, 1H), 3.21 (s, 1H), 3.20 (s, 1H), 1.27 (s, 3H), 1.25 (s, 3H); 19F-NMR (376 MHz; CDCl$_3$) δ −62.66 (s, 3F); MS (APCl+) 299.1 (M+1, 100); (APCl−) 186.0 (100)

Step F: Chiral Separation

Preparation of (+)-4-(4,4-Dimethyl-2-oxo-pyrrolidin-3-yloxy)-2-trifluoromethyl-benzonitrile The enantiomers of (±) 4-(4,4-Dimethyl-2-oxo-pyrrolidin-3-yloxy)-2-trifluoromethyl-benzonitrile, produced in Step E above, were separated by chiral HPLC (Chiralcel AD, 250× 4.6 mm; mobile phase: 8:2 hexanes-isopropanol; flow rate: 15 mL/min.)

MS (APCl, M+1) 299.1 HPLC: Chiracel AD, 250×21 mm, 80/20 Hexane/IPA, 254 nm, flow rate=0.8 mL/min, injection volume=10 μL, 16.720 min, 100% [α]: +272° C. (CHCl$_3$ Example 4

This example illustrates one of the optional functionalization reactions of Step E, in Reaction Scheme I. It illustrates the placement of an alkyl linkage on the nitrogen atom of the lactam. It also illustrate the preparation of 4-(4,4-dimethyl-2-oxo-1-propyl-pyrrolidin-3-yloxy)-2-trifluoromethyl-benzonitrile

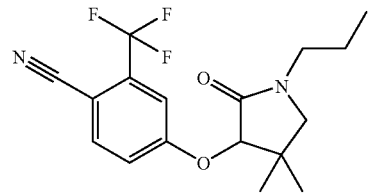

To a stirring solution comprised 4-(4,4-dimethyl-2-oxo-pyrrolidin-3-yloxy)-2-trifluoromethyl-benzonitrile, as produced above in Example 3 (0.232 g; 0.78 mmol) in tetrahydrofuran (2 mL) at ambient temperature under a nitrogen atmosphere was added a 60% sodium hydride mineral oil dispersion (0.037 g; 0.93 mmol) directly. Upon the completion of hydrogen gas liberation, 1-bromopropane (85 μL; 0.93 mmol) was added directly. The reaction mixture was stirred at ambient temperature over three days. The reaction mixture was neutralized with saturated aqueous ammonium chloride. The mixture was extracted with ethyl acetate and the layers were separated. The organic layer was dried over anhydrous magnesium sulfate and was concentrated in vacuo to afford an oil. The material was purified by column chromatography (10-75% EtOAc/hexane) to afford 0.138 g of a clear, colorless oil;

MS (APCl, M+1) 341.2
LCMS: 50-2% H$_2$O, 214 nm, 3.187 min, 100%

Examples 4A and 4B 4-(4,4-Dimethyl-2-oxo-1-propyl-pyrrolidin-3-yloxy)-2-trifluoromethyl-benzonitrile (i.e. same compound as product of Example 4 produced in a subsequent experiment) was separated into individual enantiomers using chiral HPLC (Chiracel AD, 80:20 Hexanes/ethanol, 254 nm, flow rate=15 mL/min, retention time E1=8.755 min, E2=22.12 min, diluent=ethanol)

Example 4A (+)-4-(1-Propyl-4,4-dimethyl-2-oxo-pyrrolidin-3-yloxy)-2-trifluoromethyl-benzonitrile (E2)

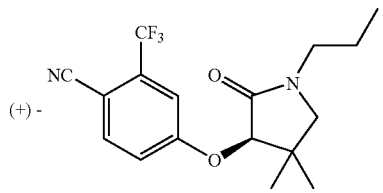

Physical, spectral and purity data for product $^1$H-NMR (400 MHz; CDCl$_3$) δ 7.73 (d, 1H, J=8.5 Hz), 7.49 (d, 1H, J=2.5 Hz), 7.41 (dd, 1H, J=8.6, 2.5 Hz), 4.53 (s, 1H), 3.30-3.20 (m, 2H), 3.20-3.14 (m, 2H), 1.60-1.51 (m, 2H), 1.25 (s, 3H), 1.22 (s, 3H), 0.91 (t, 3H, J=7.4 Hz)—trace ethanol $^{19}$F-NMR (376 MHz; CDCl$_3$) δ −62.66 (s, 3F)

MS (APCl+) 382.1 (M+1+MeCN, 61), 341.1 (M+1, 100); (APCl−) 186.0 (100)

$[α]_{589}^{23.7°}$ $^C$=+206.8° (methanol); chiral HPLC purity=100% single enantiomer LC/MS: wavelength (% purity) 214 nm (100%), 254 nm (100%), 280 nm (100%); retention time: 2.918 min; mobile phase: 50-2% H$_2$O in 3.5 min, hold 0.5 min, run time 4 min; stationary phase: Phenomenex Develosil Combi RP3 50×4.6 mm Column; 45° C.

Example 4B (−)-4-(1-Propyl-4,4-dimethyl-2-oxo-pyrrolidin-3-yloxy)-2-trifluoromethyl-benzonitrile (E1)

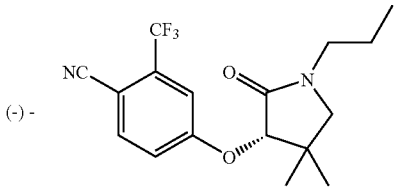

Physical, spectral and purity data for product
1H-NMR (400 MHz; CDCl$_3$) δ 7.73 (d, 1H, J=8.6 Hz), 7.49 (d, 1H, J=2.5 Hz), 7.41 (dd, 1H, J=8.8, 2.5 Hz), 4.53 (s, 1H), 3.30-3.20 (m, 2H), 3.20-3.14 (m, 2H), 1.60-1.51 (m, 2H), 1.25 (s, 3H), 1.22 (s, 3H), 0.91 (t, 3H, J=7.4 Hz)—trace ethanol
$^{19}$F-NMR (376 MHz; CDCl$_3$) δ −62.66 (s, 3F)
MS (APCl+) 382.1 (M+1+MeCN, 59), 341.1 (M+1, 100); (APCl−) 186.0 (100)
$[\alpha]_{589}^{24.2°}$ $^{C}$=−189.0° (methanol); chiral HPLC purity=100% single enantiomer
LC/MS: wavelength (% purity) 214 nm (99.8%), 254 nm (100%), 280 nm (100%); retention time: 2.887 min; mobile phase: 50-2% H$_2$O in 3.5 min, hold 0.5 min, run time 4 min; stationary phase: Phenomenex Develosil Combi RP3 50×4.6 mm Column; 45° C.

Example 5

4-(1-Benzyl-4,4-dimethyl-2-oxo-pyrrolidin-3-yloxy)-2-trifluoromethyl-benzonitrile The product of example 5 was made analogously to example 1, except using benzylamine as the starting material in Step B; no chiral separation was conducted.
MS (APCl, M+1) 389.1
LCMS: 50-2% H$_2$O, 214 nm, 3.266 min, 100%

Example 6

(+)-4-(1-Benzyl-4,4-dimethyl-2-oxo-pyrrolidin-3-yloxy)-2-trifluoromethyl-benzonitrile The product of example 6 was produced by subjecting the product of Example 5 to a chiral separation.
MS (APCl, M+1) 389.2
HPLC: Chiracel OD, 250×21 mm, 80/20 Hexane:EtOH, 254 nm, flow rate=0.8 mL/min, injection volume=10 μL, 8.434 min, 100%
[α]: +219° C. (CHCl$_3$)

Example 7

4-[1-(4-Methoxy-benzyl)-4,4-dimethyl-2-oxo-pyrrolidin-3-yloxy]-2-trifluoromethyl-benzonitrile The product of example 7 was made analogously to Example 1, except 4-methoxybenzylamine was used as the starting material in Step B; no chiral separation was conducted. MS (APCl, M+1) 419.2 LCMS: 50-2% H$_2$O, 214 nm, 3.187 min, 100%

Example 8

4-[1-(4-Hydroxy-benzyl)-4,4-dimethyl-2-oxo-pyrrolidin-3-yloxy]-2-trifluoromethyl-benzonitrile Boron tribromide (3 eq.) was added dropwise to a −78° C. solution of 4-[1-(4-methoxy-benzyl)-4,4-dimethyl-2-oxo-pyrrolidin-3-yloxy]-2-trifluoromethyl-benzonitrile (220 mg, 1_eq. in dichloromethane, i.e. the product of example 7). The reaction was allowed to gradually warm to ambient temperature overnight. Water was carefully added to the reaction and the product was extracted into dichloromethane. The organic layer was washed with water and brine and dried over anhydrous magnesium sulfate, filtered and concentrated. The crude material was purified by flash column chromatography. (Procedure of example 8 will be referred to as a "demthylation reaction hereinafter") MS (APCl, M+1) 405.0 LCMS: 50-2% H$_2$O, 214 nm, 2.390 min, 100%

Example 9

4-[1-(4-Hydroxy-benzyl)-4,4-dimethyl-2-oxo-pyrrolidin-3-yloxy]-2-trifluoromethyl-benzonitrile The product of example 9 was made from the product of example 8 by a chiral separation. MS (APCl, M+1) 405.1
HPLC: Chiracel OD, 250×21 mm, 80/20 Hexane:EtOH, 254 nm, flow rate=0.8 mL/min, injection volume=10 μL, 13.359 min, 99.8%
[α]: +216° C. (CHCl$_3$)

Example 10

4-[1-(2-Methoxy-benzyl)-4,4-dimethyl-2-oxo-pyrrolidin-3-yloxy]-2-trifluoromethyl-benzonitrile The product of example 10 was made analogously to example 1, except 2-methoxybenzylamine was used as the starting material in Step B; no chiral separation was conducted. MS (APCl, M+1) 419.2
LCMS: 50-2% H$_2$O, 214 nm, 3.345 min, 100%

Example 11

4-[1-(2-Hydroxy-benzyl)-4,4-dimethyl-2-oxo-pyrrolidin-3-yloxy]-2-trifluoromethyl-benzonitrile The product of example 11 was produced by subjecting the product of example 10 to a demethylation reaction analogous to that described in example 8. MS (APCl, M+1) 405.2
LCMS: 50-2% H$_2$0, 214 nm, 2.839 min, 100%

Example 12

4-[1-(3-Methoxy-benzyl)-4,4-dimethyl-2-oxo-pyrrolidin-3-yloxy]-2-trifluoromethyl-benzonitrile The product of Example 12 was prepared analogously to Example 4, except that 1-(3-methoxybenzyl)bromide was used in the functionalization reaction of Step E. MS (APCl, M+1) 419.1

Example 13

4-[1-(3-Hydroxy-benzyl)-4,4-dimethyl-2-oxo-pyrrolidin-3-yloxy]-2-trifluoromethyl-benzonitrile The product of example 13 was produced by subjecting the product of example 12 to a demethylation reaction analogous to that described in example 8. MS (APCl, M+1) 405.2 LCMS: 50-2% $H_2O$, 214 nm, 2.460 min, 100%

Example 14

(+)-4-[1-(3-Hydroxy-benzyl)-4,4-dimethyl-2-oxo-pyrrolidin-3-yloxy]-2-trifluoromethyl-benzonitrile The product of example 14 was prepared by subjecting the product of example 13 to chiral HPLC separation.
$[\alpha]_{589}$ (24.1° C., $CH_3OH$): +138.9° MS (APCl, M+1) 405.2
LCMS: wavelength (% purity) 214 nm (100%), 254 nm (100%), 280 nm (100%); retention time: 2.485 min; mobile phase: 50-2% H2O in 3.5 min, hold 0.5 min, run time 4 min; stationary phase: Phenomenex Develosil Combi RP3 50×4.6 mm Column; 45° C.

Example 15

4-[1-(2-Fluoro-benzyl)-4,4-dimethyl-2-oxo-pyrrolidin-3-yloxy]-2-trifluoromethyl-benzonitrile The product of Example 15 was made analogously to example 1, except using 3-fluorobenzylamine was used as the starting material in Step D, no chiral separation was conducted.
MS (APCl, M+1) 407.2 LCMS: 50-2% $H_2O$, 214 nm, 3.293 min, 100%

Example 16

4-[1-(2-Fluoro-benzyl)-4,4-dimethyl-2-oxo-pyrrolidin-3-yloxy]-2-trifluoromethyl-benzonitrile The product of Example 15 was prepared analogously to Example 1, except using 2-fluorobenzylamine was used as the starting material in Step B; no chiral separation was conducted. MS (APCl, M+1) 407.2
LCMS: 50-2% $H_2O$, 214 nm, 3.315 min, 100%

Example 17

4-[1-(4-Fluoro-benzyl)-4,4-dimethyl-2-oxo-pyrrolidin-3-yloxy]-2-trifluoromethyl-benzonitrile The product of example 17 was prepared analogously to example 1, except using 4-fluorobenzylamine was used as the starting material in Step B; no chiral separation was conducted. MS (APCl, M+1) 407.2
LCMS: 50-2% $H_2O$, 214 nm, 3.301 min, 100%

Example 18

4-[1-(3,5Dihydroxy-benzyl)-4,4-dimethyl-2-oxo-pyrrolidin-3-yloxy]-2-trifluoromethyl-benzonitrile The product of Example 18 was made analogously to Example 1, except using 3,5-dimethylbenzylamine as the starting material in Step B, no chiral separation was conducted. MS (APCl, M+1) 421.2 LCMS: 50-2% H20, 214 nm, 1.839 min, 100%

Example 19

4-(1-Butyl-4,4-dimethyl-2-oxo-pyrrolidin-3-yloxy)-2-trifluoromethyl-benzonitrile The product of Example 19 was made analogously to Example 4, except 1-bromobutane was used as a starting material in the functionalization reaction of Step E.
MS (APCl, M+1) 355.1
LCMS: 50-2% H2O, 214 nm, 2.877 min, 100%

Example 20

(+)-4-(1-Butyl-4,4-dimethyl-2-oxo-pyrrolidin-3-yloxy)-2-trifluoromethyl-benzonitrile The product of example 20 was prepared analogously to Example 1, except that n-butylamine was used as one of the starting materials in Step D. The enantiomers were separated using chiral HPLC.
$[\alpha]_{589}$ (23.5° C., $CH_3OH$): +187.4°
MS (APCl, M+1) 355.1
LCMS: wavelength (% purity) 214 nm (100%), 254 nm (100%), 280 nm (100%); retention time: 3.245 min; mobile phase: 50-2% H2O in 3.5 min, hold 0.5 min, run time 4 min; stationary phase: Phenomenex Develosil Combi RP3 50×4.6 mm Column; 45° C.
LCMS: 50-2% $H_2O$, 214 nm, 3.242 min, 100%

Example 21

4-(1-Ethyl-4,4-dimethyl-2-oxo-pyrrolidin-3-yloxy)-2-trifluoromethyl-benzonitrile The product of example 21 was made analogously to Example 4, except 1-bromoethane was used as a starting material in the functionalization reaction of Step E.
MS (APCl, M+1) 327.2
HPLC: 254 nm, 13.827 min, 99%

Example 22

(±)-4-[4,4-Dimethyl-1-(4-methylsulfanyl-benzyl)-2-oxo-pyrrolidin-3-yloxy]-2-trifluoromethyl-benzonitrile The product of example 22 was prepared analogously to Example 1, except that 4-methylsulfanyl-benzylamine was used as a starting material in Step B, no separation of stereoisomers was conducted.
MS (APCl, M+1) 435
LCMS: 254 nm, 97%
Melting point: 44.1-44.8° C.

Example 23

(+)-4-{1-[1-(3-Methoxy-phenyl)-ethyl]-4,4-dimethyl-2-oxo-pyrrolidin-3-yloxy}-2-trifluoromethyl-benzonitrile The product of Example 23 was prepared analogously to Example 1, except that 1-(3-methoxy-phenyl)-ethylamine was used in Step B as a starting material; chased with chloroform to afford a clear colorless oil.
$[\alpha]_{589}$ (ambient temperature, $CH_2Cl_2$): +49.5°
MS (APCl, M+1) 433 LCMS: 254 nm, 97%

Example 24

(+)-4-{1-[1-(3-Hydroxy-phenyl)-ethyl]-4,4-dimethyl-2-oxo-pyrrolidin-3-yloxy}-2-trifluoromethyl-benzonitrile The product of Example 24 was prepared by dissolving (+)-4-{1-[1-(3-methoxy-phenyl)-ethyl]-4,4-dimethyl-2-oxo-pyrrolidin-3-yloxy}-2-trifluoromethyl-benzonitrile (0.456 g, product of Example 23) in dichloromethane. The reaction mixture was cooled to −10° C. under a nitrogen atmosphere and 3 mL of a 1.0 M boron tribromide in dichloromethane solution was added. After fifteen minutes the reaction was quenched with methanol and reduced to dryness in vacuo. The resulting residue was dissolved in ethyl acetate and washed with saturated aqueous sodium bicarbonate, water, and brine. The organic phase was dried over anhydrous magnesium sulfate and was concentrated in vacuo to afford 0.633 g of a white solid. The product was recrystallized from ethanol to afford 0.1122 g of a white microcrystalline solid.

$[\alpha]_{589}$ (ambient temperature, $CH_2Cl_2$): +34°
MS (APCl, M+1)$_{419}$ LCMS: 254 nm, 98
Melting point: 185.1-185.8° C.

Example 25

(±)-3-[3-(4-Cyano-3-trifluoromethyl-phenoxy)-4,4-dimethyl-2-oxo-pyrrolidin-1-ylmethyl]-benzoic acid methyl ester The product of Example 25 was prepared analogously to Example 1, except that 3-aminomethyl-benzoic acid methyl ester was used in Step B as a starting material, no separation of stereoisomers was conducted.

MS (APCl, M+1) 447
LCMS: 214, 254, and 280 nm, 100%

Example 26

3-[3-(4-Cyano-3-trifluoromethyl-phenoxy)-4,4-dimethyl-2-oxo-pyrrolidin-1-ylmethyl]-benzoic acid The compound obtained in Example 25, (±)-3-[3-(4-cyano-3-trifluoromethyl-phenoxy)-4,4-dimethyl-2-oxo-pyrrolidin-1-ylmethyl]-benzoic acid methyl ester, (0.128 g, 0.29 mmol) was dissolved in 4 mL THF and 1.0 mL 1 M NaOH was added. The reaction was stirred at ambient temperature overnight. The reaction mixture was acidified with 1 N HCl to pH ~3 and extracted into ethyl acetate. The organic layer was washed with brine and dried over anhydrous magnesium sulfate and concentrated in vacuo. The material was triturated with diethyl ether and filtered to obtain the carboxylic acid as a white solid (0.105 g, 85%).

MS (APCl, M+1) 432.9
LCMS: 50-2% H2O, 214 nm, 2.406 min, 100%

Example 27

5-[3-(4-cyano-3-trifluoromethyl-phenoxy)-4,4-dimethyl-2-oxo-pyrrolidin-1-ylmethyl]-furan-2-carboxylic acid isopropyl ester The compound obtained in Example 29, 5-[3-(4-cyano-3-trifluoromethyl-phenoxy)-4,4-dimethyl-2-oxo-pyrrolidin-1-ylmethyl]-furan-2-carboxylic acid ethyl ester, (0.461 g, 1.024 mmol) was dissolved in 5 mL THF and 1.5 mL 1 M NaOH was added. The reaction was stirred at ambient temperature overnight. The reaction mixture was acidified with 1 N HCl to pH ~3 and extracted into ethyl acetate. The organic layer was washed with brine and dried over anhydrous magnesium sulfate and concentrated in vacuo to obtain the carboxylic acid, 5-[3-(4-cyano-3-trifluoromethyl-phenoxy)-4,4-dimethyl-2-oxo-pyrrolidin-1-ylmethyl]-furan-2-carboxylic acid, as a white solid (0.417 g).

The acid from above (0.179 g, 0.42 mmol) was suspended in 7 mL isopropanol and a drop of concentrated sulfuric acid was added. The reaction was heated to 80° C. for 48 hours. The reaction was cooled to ambient temperature at which time a precipitate formed. The reaction was concentrate in vacuo to afford a white solid. The material was dissolved in ethyl acetate and washed with 1 N NaOH (to remove starting acid), water and saturated aqueous sodium chloride. The organic layer was dried over anhydrous magnesium sulfate and concentrated in vacuo. The solid was recrystallized from ethanol and dried in a 50° C. vacuum oven overnight to yield 150 mg, of 5-[3-(4-cyano-3-trifluoromethyl-phenoxy)-4,4-dimethyl-2-oxo-pyrrolidin-1-ylmethyl]-furan-2-carboxylic acid isopropyl ester.

MS (APCl, M−1): 465.1
LCMS: 50-2% H2O, 214 nm, 3.357 min, 100%

Examples 28-67

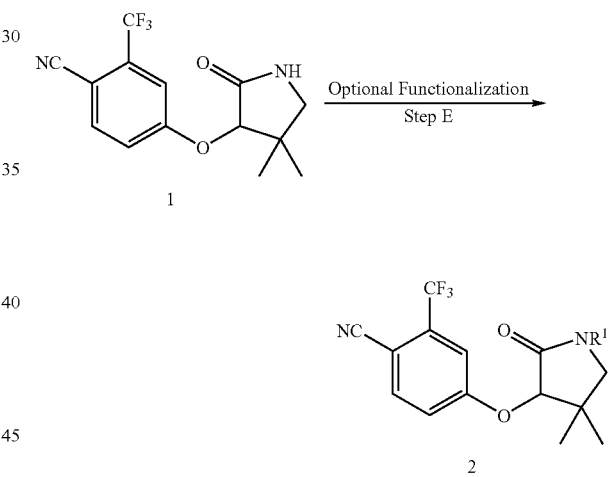

Examples 28-67 were produced via combinatorial chemistry. As depicted above, a common starting material, 4-(4,4-dimethyl-2-oxo-pyrrolidin-3-yloxy)-2-trifluoromethyl-benzonitrile (product of Example 3) was subjected to a series of functionalization reactions in order to place a variety of functional groups on the nitrogen atom of the lactam (i.e. $R^1$). These reactions were carried out in the following manner.

To a stirring 0.2M solution of 4-(4,4-dimethyl-2-oxo-pyrrolidin-3-yloxy)-2-trifluoromethyl-benzonitrile (product of Example 3, 60 mg, 0.2 mmol) in DMF (1 mL) and NaI (10 mg, 0.07 mmol) at ambient temperature was added a 60% sodium hydride mineral oil suspension (8 mg; 0.20 mmol) in 0.5 mL DMF. Upon the completion of hydrogen gas liberation, 0.4M solutions of alkyl bromides or chlorides (corresponding to the desired $R^1$ substituent) in DMF (0.2 mmol; 0.5 mL/reaction) were added. The reactions were capped and stirred on a shaker at ambient temperature overnight. The reaction mixture was quenched with 0.5 mL MeOH and 60 mg of macroporous (MP) tosic acid. The reactions were capped and stirred on a shaker for at least 30 minutes. The reactions were filtered, concentrated and purified by HPLC.

LCMS (x): analysis reported below were carried out by one of the methods described below:

(1) Xterra-Phenyl, 100 mm×3 mm, 5μ, 95/5 to 2/98 H$_2$O+0.5% Formic acid/ACN+0.5% Formic acid over 2.0 min, hold 2.0 min, injection volume: 5 μL (2) YMC C8, 100 mm×3 mm, 3μ, 70/30 to 2/98 H$_2$O+10 mMNH$_4$OH/ACN+0.5% Formic acid over 3.0 min, hold 2.0 min, injection volume: 5 μL (3) Atlantis dC18, 5 cm×4.6 mm, 3μ, 90/10 to 2/98 H$_2$O+0.5% Formic acid/ACN+0.5% Formic acid over 3.5 min, hold 1.5 min, injection volume: 20 μL sample prep: 900 μL 1:1 ACN/H$_2$O (4) Atlantis dC18, 5 cm×4.6 mm, 3μ, 80/20 to 2/98 H$_2$O+0.5% Formic acid/ACN+0.5% Formic acid over 2.5 min, hold 2.5 min, injection volume: 10 μL sample prep: 900 μL 1:1 ACN/H$_2$O (5) Sunfire C18 19×100 mm 5 μm, flow rate 30 mL/min; 25% Acetonitrile with 0.1% formic acid/Water with 0.1% formic acid, hold for 1 min; gradient to 100% Acetonitrile with 0.1% formic acid over 6.5 minutes, hold for 4 minutes.

(6) ) Xterra-Phenyl, 100 mm×3 mm, 5μ, 95/5 to 15/85 H$_2$O+0.5% Formic acid/ACN +0.5% Formic acid over 6.50 min, hold 1.5 min, injection volume: 5 μL (7) Atlantis dC18, 5 cm×4.6 mm, 3μ, 90/10 to 2/98 H$_2$O+0.5% Formic acid/ACN+0.5% Formic acid over 3.5 min, hold 1.5 min, injection volume: 10 μL sample prep: 900 μL 1:1 ACN/H$_2$O

TABLE I

| Example | Structure | Name | LCms |
|---|---|---|---|
| 28 | 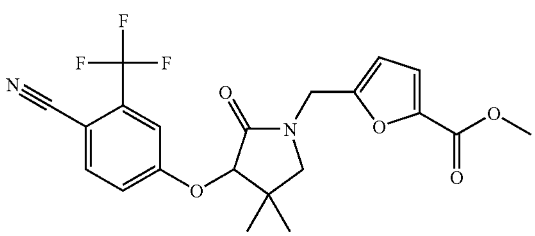 | 5-[3-(4-Cyano-3-trifluoromethyl-phenoxy)-4,4-dimethyl-2-oxo-pyrrolidin-1-ylmethyl]-furan-2-carboxylic acid methyl ester | LCMS (1): 2.65 in, 97.8%, 436.1 |
| 29 | 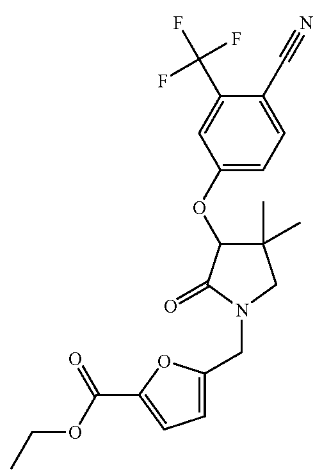 | 5-[3-(4-Cyano-3-trifluoromethyl-phenoxy)-4,4-dimethyl-2-oxo-pyrrolidin-1-ylmethyl]-furan-2-carboxylic acid ethyl ester | LCMS (1): 2.72 in, 98.7%, 450.1 |
| 30 | 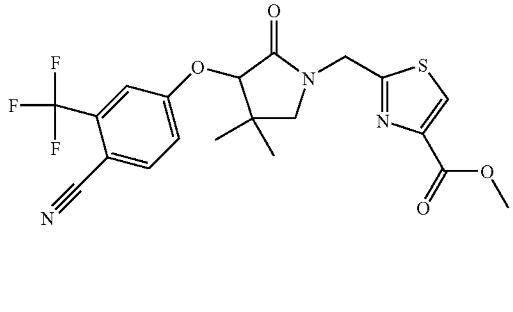 | 2-[3-(4-Cyano-3-trifluoromethyl-phenoxy)-4,4-dimethyl-2-oxo-pyrrolidin-1-ylmethyl]-thiazole-4-carboxylic acid methyl ester | LCMS (1): 2.57 min, 98.9%, 453 |

TABLE I-continued

| Example | Structure | Name | LCms |
|---|---|---|---|
| 31 | 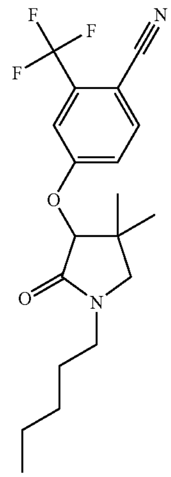 | 4-(4,4-Dimethyl-2-oxo-1-pentyl-pyrrolidin-3-yloxy)-2-trifluoromethyl-benzonitrile | LCMS (1): 2.78 min, 100%, 368.1 |
| 32 | 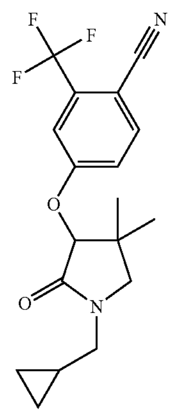 | 4-(1-Cyclopropylmethyl-4,4-dimethyl-2-oxo-pyrrolidin-3-yloxy)-2-trifluoromethyl-benzonitrile | LCMS (1): 2.76 min, 100%, 352.1 |
| 33 | 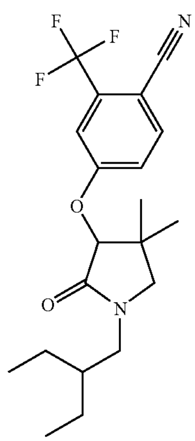 | 4-[1-(2-Ethyl-butyl)-4,4-dimethyl-2-oxo-pyrrolidin-3-yloxy]-2-trifluoromethyl-benzonitrile | LCMS (1): 2.85 min, 100%, 382.1 |
| 34 | 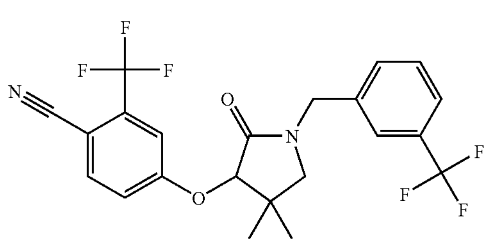 | 4-[4,4-Dimethyl-2-oxo-1-(3-trifluoromethyl-benzyl)-pyrrolidin-3-yloxy]-2-trifluoromethyl-benzonitrile | LCMS (1): 2.83 in, 100%, 456.1 |

TABLE I-continued

| Example | Structure | Name | LCms |
|---|---|---|---|
| 35 | 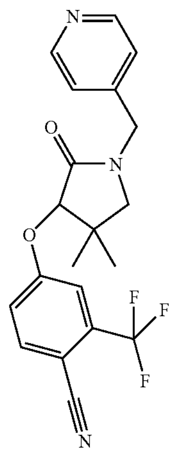 | 4-(4,4-Dimethyl-2-oxo-1-pyridin-4-ylmethyl-pyrrolidin-3-yloxy)-2-trifluoromethyl-benzonitrile | LCMS (2): 2.67 min, 97.2%, 389.1 |
| 36 | 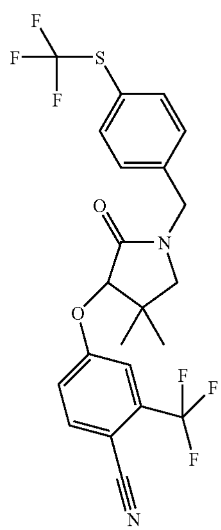 | 4-[4,4-Dimethyl-2-oxo-1-(4-trifluoromethylsulfanyl-benzyl)-pyrrolidin-3-yloxy]-2-trifluoromethyl-benzonitrile | LCMS (2): 3.7 min, 100%, 488.1 |
| 37 | 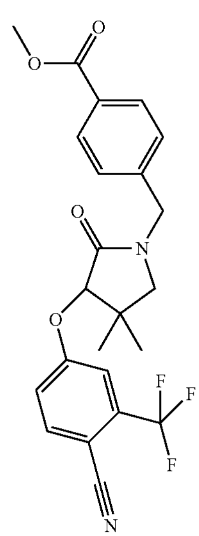 | 4-[3-(4-Cyano-3-trifluoromethyl-phenoxy)-4,4-dimethyl-2-oxo-pyrrolidin-1-ylmethyl]-benzoic acid methyl ester | MS (APCI, M + 1) 447.1 LCMS: 50 - 2% H$_2$O, 214 nm, 3.169 min, 100% |

TABLE I-continued

| Example | Structure | Name | LCms |
|---|---|---|---|
| 38 | 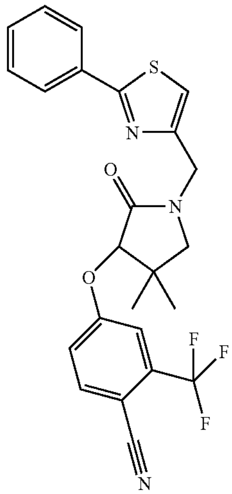 | 4-(1-Benzothiazol-2-ylmethyl-4,4-dimethyl-2-oxo-pyrrolidin-3-yloxy)-2-trifluoromethyl-benzonitrile | LCMS (2): 3.48 min, 100%, 471.1 |
| 39 | 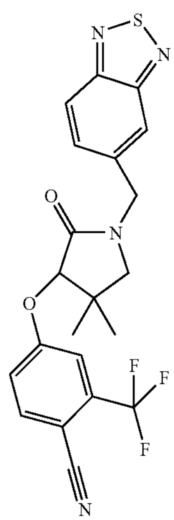 | 4-(1-Benzo[1,2,5]thiadiazol-5-ylmethyl-4,4-dimethyl-2-oxo-pyrrolidin-3-yloxy)-2-trifluoromethyl-benzonitrile | LCMS (2): 3.27 min, 100%, 446.1 |
| 40 | 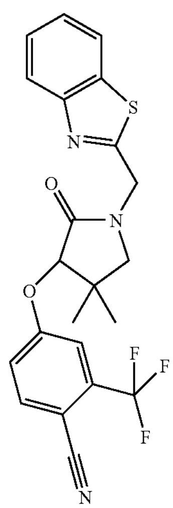 | 4-(1-Benzothiazol-2-ylmethyl-4,4-dimethyl-2-oxo-pyrrolidin-3-yloxy)-2-trifluoromethyl-benzonitrile | LCMS (2): 3.25 min, 99.1%, 445.1 |

TABLE I-continued

| Example | Structure | Name | LCms |
|---|---|---|---|
| 41 | 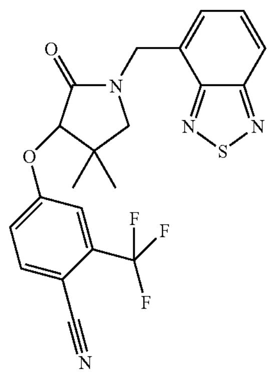 | 4-(1-Benzo[1,2,5]thiadiazol-4-ylmethyl-4,4-dimethyl-2-oxo-pyrrolidin-3-yloxy)-2-trifluoromethyl-benzonitrile | LCMS (2): 3.28 min, 100%, 446.1 |
| 42 | 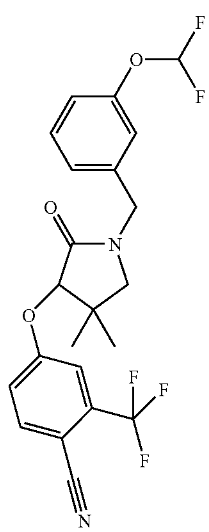 | 4-[1-(3-Difluoromethoxy-benzyl)-4,4-dimethyl-2-oxo-pyrrolidin-3-yloxy]-2-trifluoromethyl-benzonitrile | LCMS (2): 3.37 min, 98.1%, 454.1 |
| 43 | 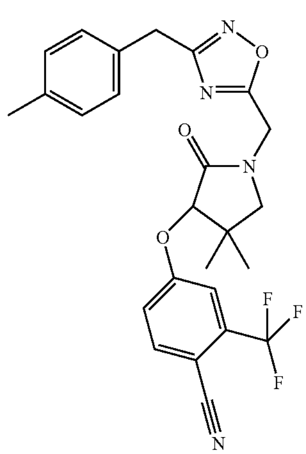 | 4-{4,4-Dimethyl-1-[3-(4-methyl-benzyl)-[1,2,4]oxadiazol-5-ylmethyl]-2-oxo-pyrrolidin-3-yloxy}-2-trifluoromethyl-benzonitrile | LCMS (2): 3.43 min, 99.4%, 484.1 |

TABLE I-continued

| Example | Structure | Name | LCms |
|---|---|---|---|
| 44 | 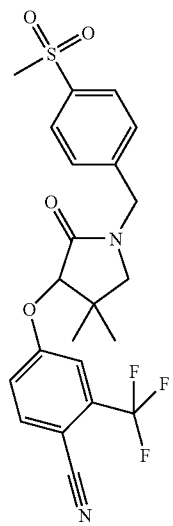 | 4-[1-(4-Methanesulfonyl-benzyl)-4,4-dimethyl-2-oxo-pyrrolidin-3-yloxy]-2-trifluoromethyl-benzonitrile | LCMS (2): 2.87 min, 98.4%, 466.1 |
| 45 | 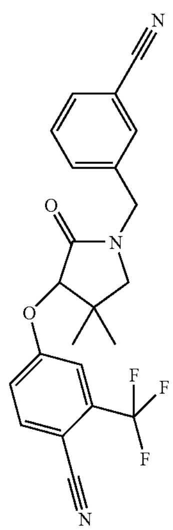 | 1-[1-(3-Cyano-benzyl)-4,4-dimethyl-2-oxo-pyrrolidin-3-yloxy]-2-trifluoromethyl-benzonitrile | LCMS (2): 3.13 min, 99.1%, 413.1 |
| 46 | 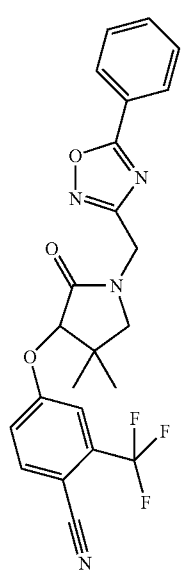 | 4-[4,4-Dimethyl-2-oxo-1-(5-phenyl-[1,2,4]oxadiazol-3-ylmethyl)-pyrrolidin-3-yloxy]-2-trifluoromethyl-benzonitrile | LCMS (2): 3.38 min, 100%, 456.1 |

TABLE I-continued

| Example | Structure | Name | LCms |
|---|---|---|---|
| 47 | 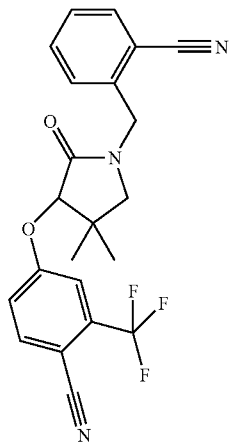 | 4-[1-(2-Cyano-benzyl)-4,4-dimethyl-2-oxo-pyrrolidin-3-yloxy]-2-trifluoromethyl-benzonitrile | LCMS (2): 3.2 min, 100%, 413.1 |
| 48 | 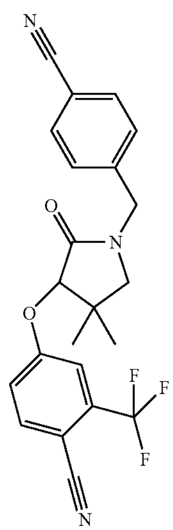 | 4-[1-(4-Cyano-benzyl)-4,4-dimethyl-2-oxo-pyrrolidin-3-yloxy]-2-trifluoromethyl-benzonitrile | LCMS (2): 3.17 min, 98.3%, 413.1 |
| 49 | 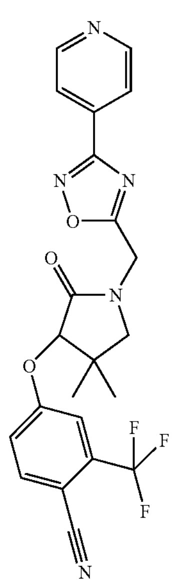 | 4-[4,4-Dimethyl-2-oxo-1-(3-pyridin-4-yl-[1,2,4]oxadiazol-5-ylmethyl)-pyrrolidin-3-yloxy]-2-trifluoromethyl-benzonitrile | LCMS (2): 2.92 min, 97.7%, 457.1 |

TABLE I-continued

| Example | Structure | Name | LCms |
|---|---|---|---|
| 50 | 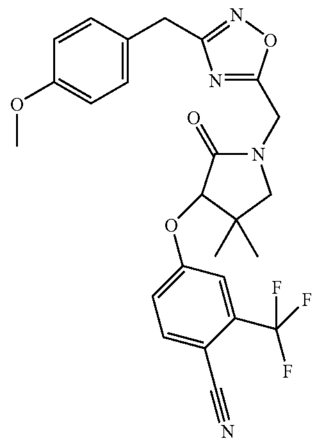 | 4-{1-[3-(4-Methoxy-benzyl)-[1,2,4]oxadiazol-5-ylmethyl]-4,4-dimethyl-2-oxo-pyrrolidin-3-yloxy}-2-trifluoromethyl-benzonitrile | LCMS (2): 3.3 min, 100%, 500.1 |
| 51 | 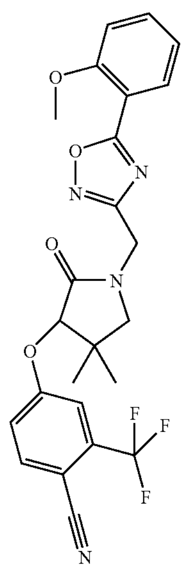 | 4-{1-[5-(2-Methoxy-phenyl)-[1,2,4]oxadiazol-3-ylmethyl]-4,4-dimethyl-2-oxo-pyrrolidin-3-yloxy}-2-trifluoromethyl-benzonitrile | LCMS (2): 3.25 min, 98.3%, 486.1 |
| 52 | 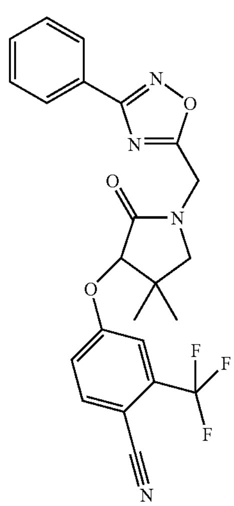 | 4-[4,4-Dimethyl-2-oxo-1-(3-phenyl-[1,2,4]oxadiazol-5-ylmethyl)-pyrrolidin-3-yloxy]-2-trifluoromethyl-benzonitrile | LCMS (2): 3.4 min, 100%, 456.1 |

TABLE I-continued

| Example | Structure | Name | LCms |
|---|---|---|---|
| 53 | 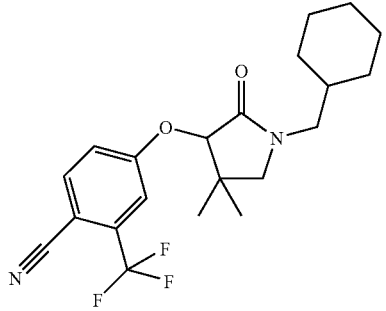 | 4-(1-Cyclohexylmethyl-4,4-dimethyl-2-oxo-pyrrolidin-3-yloxy)-2-trifluoromethyl-benzonitrile | LCMS (3): 4.54 min, 100%, 394.1 |
| 54 | 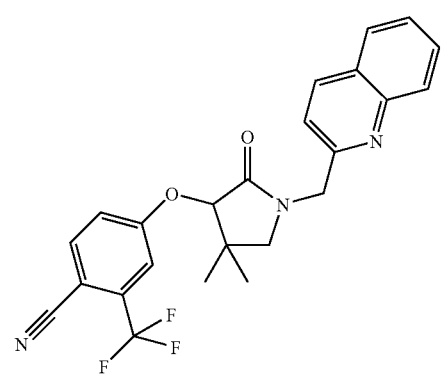 | 4-(4,4-Dimethyl-2-oxo-1-quinolin-2-ylmethyl-pyrrolidin-3-yloxy)-2-trifluoromethyl-benzonitrile | LCMS (3): 4.17 min, 97.8%, 439.1 |
| 55 | 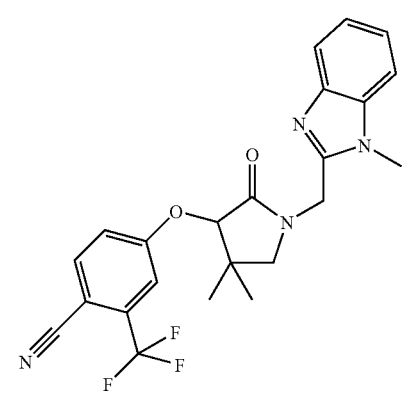 | 4-[4,4-Dimethyl-1-(1-methyl-1H-benzoimidazol-2-ylmethyl)-2-oxo-pyrrolidin-3-yloxy]-2-trifluoromethyl-benzonitrile | LCMS (3): 3.71 min, 94.6%, 442.1 |
| 56 | 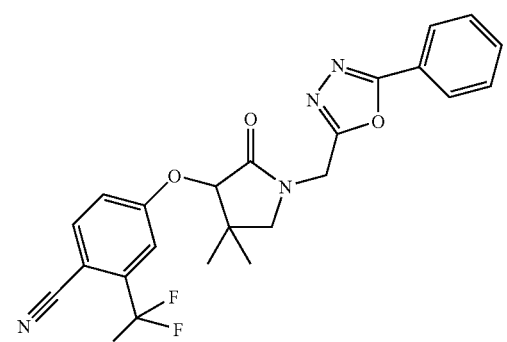 | 4-[4,4-Dimethyl-2-oxo-1-(5-phenyl-[1,3,4]oxadiazol-2-ylmethyl)-pyrrolidin-3-yloxy]-2-trifluoromethyl-benzonitrile | LCMS (3): 3.99 min, 100%, 456.1 |

TABLE I-continued

| Example | Structure | Name | LCms |
|---|---|---|---|
| 57 | 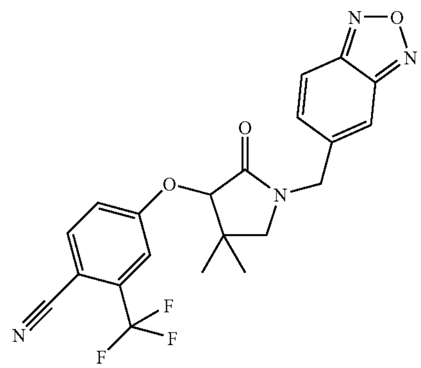 | 4-(1-Benzo[1,2,5]oxadiazol-5-ylmethyl-4,4-dimethyl-2-oxo-pyrrolidin-3-yloxy)-2-trifluoromethyl-benzonitrile | LCMS (3): 4.13 min, 100%, 430.1 |
| 58 | 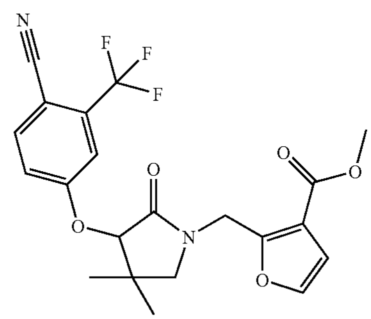 | 2-[3-(4-Cyano-3-trifluoromethyl-phenoxy)-4,4-dimethyl-2-oxo-pyrrolidin-1-ylmethyl]-furan-3-carboxylic acid methyl ester | LCMS (3): 4.07 min, 97.1%, 436.1 |
| 59 | 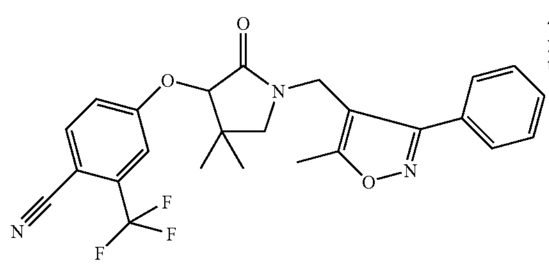 | 4-[4,4-Dimethyl-1-(5-methyl-3-phenyl-isoxazol-4-ylmethyl)-2-oxo-pyrrolidin-3-yloxy]-2-trifluoromethyl-benzonitrile | LCMS (3): 4.25 min, 100%, 469.1 |
| 60 | 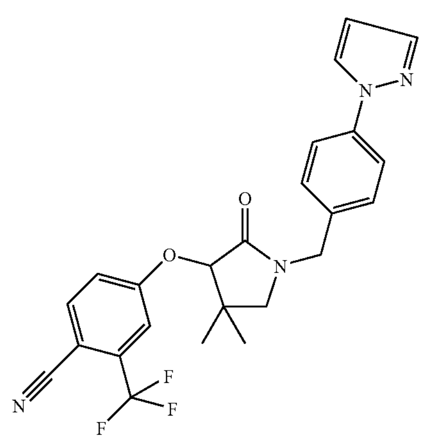 | 4-[4,4-Dimethyl-2-oxo-1-(4-pyrazol-1-yl-benzyl)-pyrrolidin-3-yloxy]-2-trifluoromethyl-benzonitrile | LCMS (3): 4.12 min, 93.9%, 454.1 |

TABLE I-continued

| Example | Structure | Name | LCms |
|---|---|---|---|
| 61 | 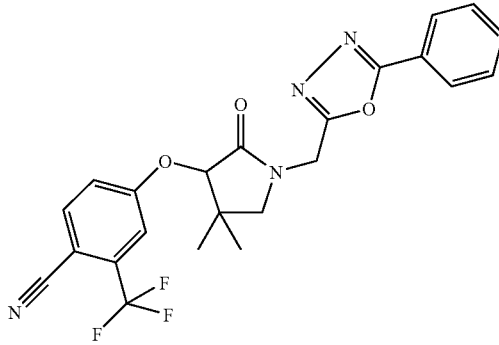 | 4-[4,4-Dimethyl-2-oxo-1-(5-p-tolyl-[1,3,4]oxadiazol-2-ylmethyl)-pyrrolidin-3-yloxy]-2-trifluoromethyl-benzonitrile | LCMS (3): 4.11 min, 100%, 470.1 |
| 62 | 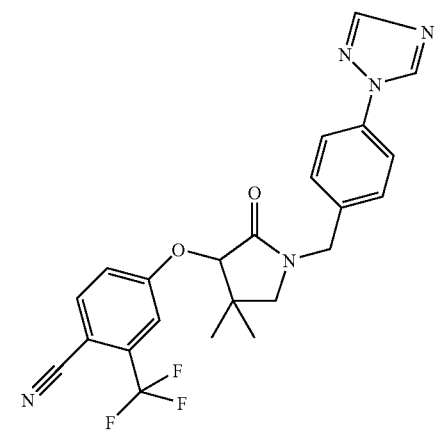 | 4-[4,4-Dimethyl-2-oxo-1-(4-[1,2,4]triazol-1-yl-benzyl)-pyrrolidin-3-yloxy]-2-trifluoromethyl-benzonitrile | LCMS (4): 3.04 min, 100%, 455.1 |
| 63 | 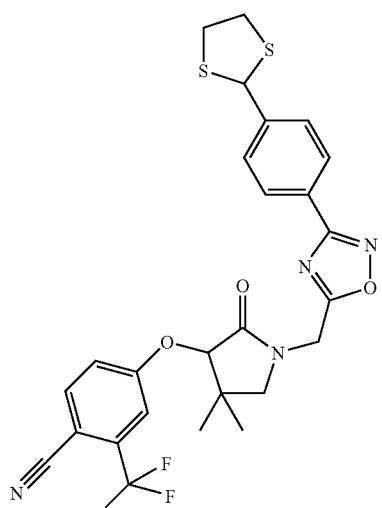 | 4-{1-[3-(4-[1,3]Dithiolan-2-yl-phenyl)-[1,2,4]oxadiazol-5-ylmethyl]-4,4-dimethyl-2-oxo-pyrrolidin-3-yloxy}-2-trifluoromethyl-benzonitrile | LCMS (4): 3.62 min, 93.9%, 560.1 |
| 64 | 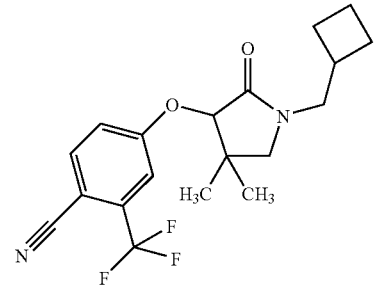 | 4-(1-Cyclobutylmethyl-4,4-dimethyl-2-oxo-pyrrolidin-3-yloxy)-2-trifluoromethyl-benzonitrile | LCMS (3): 4.33 min, 100%, 503.1 |

TABLE I-continued

| Example | Structure | Name | LCms |
|---|---|---|---|
| 65 | 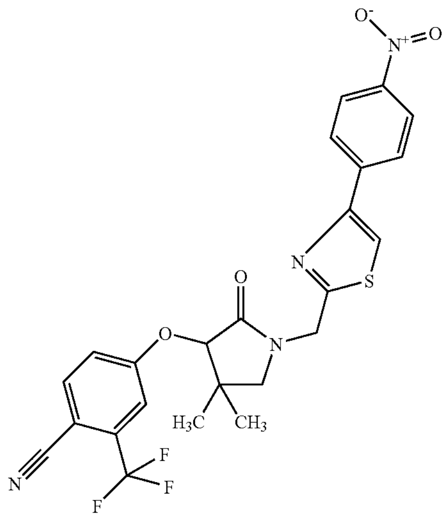 | 4-{4,4-Dimethyl-1-[4-(4-nitro-phenyl)-thiazol-2-ylmethyl]-2-oxo-pyrrolidin-3-yloxy}-2-trifluoromethyl-benzonitrile | LCMS (4): 3.52 minutes, 91.33%, 516.1 |
| 66 | 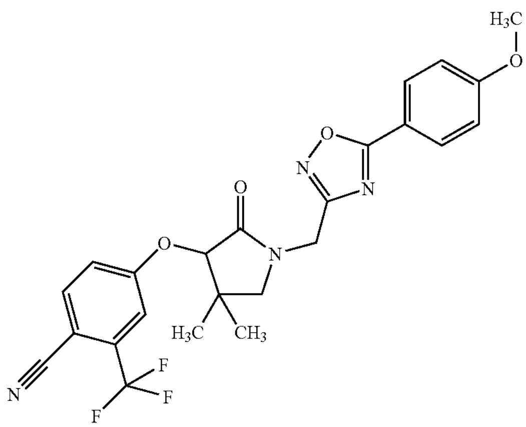 | 4-{1-[5-(4-Methoxy-phenyl)-[1,2,4]oxadiazol-3-ylmethyl]-4,4-dimethyl-2-oxo-pyrrolidin-3-yloxy}-2-trifluoromethyl-benzonitrile | LCMS (4): 3.45 minutes, 100%, 486.1 |
| 67 | 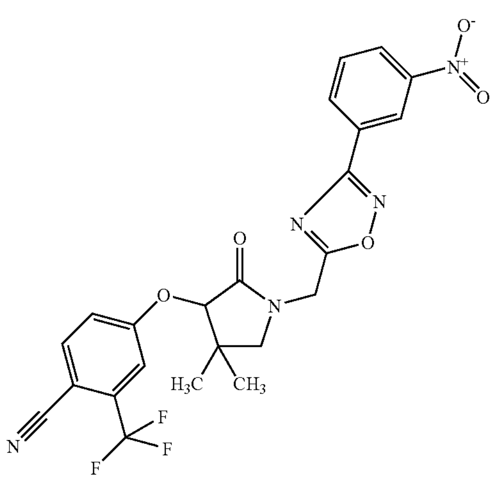 | 4-{4,4-Dimethyl-1-[3-(3-nitro-phenyl)-[1,2,4]oxadiazol-5-ylmethyl]-2-oxo-pyrrolidin-3-yloxy}-2-trifluoromethyl-benzonitrile | |

Example 68

4-(4,4-Dimethyl-1-methylsulfanylmethyl-2-oxo-pyrrolidin-3-yloxy)-2:trifluoromethyl-benzonitrile

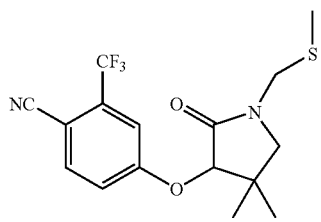

The product of Example 68 was prepared analogously to Example 4, except that in Step E 1-methylsulfanyl chloride was used as a reactant in the alkylation reaction.

MS (APCl, M+1) 359
LCMS: 50-2% H$_2$O; 214 nm Average, 3.02 min. 100%, M+1 359.0

Example 69

(+)-4-[4,4-Dimethyl-2-oxo-1-(1-phenyl-ethyl)-pyrrolidin-3-yloxy]-2-trifluoromethyl-benzonitrile The product of Example 69 was prepared analogously to Example 1, except that (S)-1-phenyl-ethylamine was used in Step B as a starting material, no separation of stereoisomers was conducted.

[α]$_{589}$ (ambient temperature, CH$_2$Cl$_2$): +50°
MS (APCl, M+1) 403 LCMS: 254 nm, 97.7%

Example 70

(±)-4-{1-[1-(4-Fluoro-phenyl)-ethyl]-4,4-dimethyl-2-oxo-pyrrolidin-3-yloxy}-2-trifluoromethyl-benzonitrile The product of Example 70 was prepared analogously to Example 1, except that (±)-1-(4-fluoro-phenyl)-ethylamine was used in Step B instead of (S)-(+)-sec-butylamine. The diastereomeric mixture was separated by flash silica column chromatography (solvent system by volume: 65% hexanes, 35% ethyl acetate) to give a racemic mixture of the (R,R)- and (S,S)-enantiomers and a racemic mixture of the (R,S)- and (S,R)-enantiomers.

MS (APCl M+1 421 LCMS: 254 nm, 98.4% Melting point: 82-83° C.

Example 71

(±)-4-{1-[1-(4-Fluoro-phenyl)-ethyl]-4,4-dimethyl-2-oxo-pyrrolidin-3-yloxy}-2-trifluoromethyl-benzonitrile

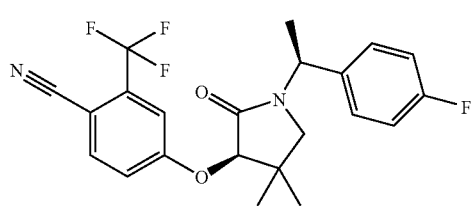

(Racemic mixture of R,S- and S,R-enantiomers)

The product of Example 71 was prepared analogously to Example 1, except that in the Amidation Reaction of Step B, 1-(4-fluoro-phenyl)-ethylamine was used as one of the reactants.

MS (APCl, M+1)$_{421}$ LCMS: 254 nm, 98.8%, Melting point: 114-115° C.

Example 72

(+)-4-[4,4-Dimethyl-1-(1-methyl-butyl)-2-oxo-pyrrolidin-3-yloxy]-2-trifluoromethyl-benzonitrile The product of Example 71 was prepared analogously to Example 1, except that (±)-1-methyl-butylamine was used in Step B instead of (S)-(+)-sec-butylamine. The product was purified by flash silica column chromatography (solvent system by volume: 75% hexanes, 25% ethyl acetate) to give an equal mixture of four diastereomers.

MS (APCl, M+1) 369 LCMS: 254 nm, 98.4%

Examples 73-94 and 99-100F

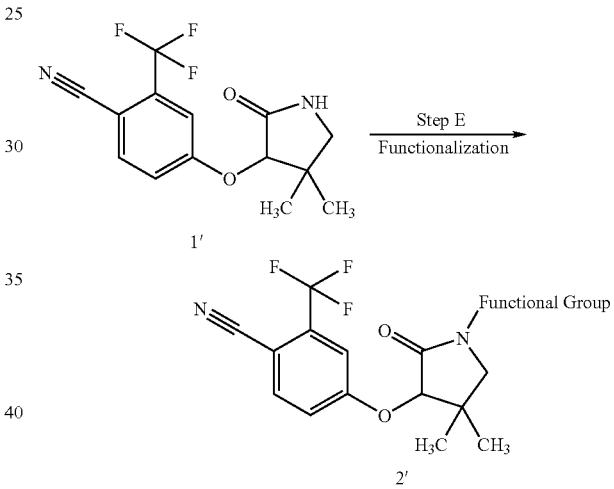

Examples 73-94, and 99-100 further illustrate the preparation of a series of sulfonamide, acyl, alkyl, and thioether derivatives. As depicted above, a common starting material, 4-(4,4-dimethyl-2-oxo-pyrrolidin-3-yloxy)-2-trifluoromethyl-benzonitrile (product of Example 3) was subjected to a functionalization reaction in order to place a variety of differing functional groups on the nitrogen atom of the lactam (i.e. R$^1$). One of two reaction sequences was carried out, A or B, as described below.

Method A

To a stirring solution of 4-(4,4-dimethyl-2-oxo-pyrrolidin-3-yloxy)-2-trifluoromethyl-benzonitrile (product of Example 3, 0.20 g, 0.67 mmol) in 3 mL THF under a nitrogen atmosphere was added sodium hydride (60% dispersion in mineral oil, 0.030 g, 0.74 mmol). After gas evolution ceased (~10 minutes), a sulfonyl chloride (corresponding to the desired R$^1$ moiety) (0.094 mL, 0.74 mmol) was added and the reaction was stirred at ambient temperature for 4 hours. The reaction mixture was neutralized with saturated aqueous ammonium chloride. The mixture was extracted with ethyl acetate and the layers were separated. The organic layer washed with saturated sodium chloride and then dried over anhydrous magnesium sulfate and concentrated in vacuo. This material was purified by flash silica column chromatography (Biotage Horizon system, 25% EtOAc/hex, 12+M column). This afforded the product which was dried in a 50° C. vacuum oven overnight to give the desired product.

Method B

To a −30° C. stirring solution of 4-(4,4-dimethyl-2-oxo-pyrrolidin-3-yloxy)-2-trifluoromethyl-benzonitrile (product of example 3, 0.11 g, 0.37 mmol) in 10 mL THF under a nitrogen atmosphere was added LiHMDS(lithium hexamethyl disilyl amide) or NaHMDS(sodium hexamethyl disilyl amide) (1.0 M/THF, 0.48 mL, 0.48 mmol). The reaction was stirred at −30° C. for 30 minutes. A substituted sulfonyl chloride (corresponding to the desired $R^1$ moiety) (1.3 equiv) was added and the reaction was allowed to gradually warm to ambient temperature overnight. The reaction mixture was extracted into ethyl acetate and washed successively with saturated sodium bicarbonate then saturated aqueous sodium chloride. The material was then dried over anhydrous magnesium sulfate and concentrated in vacuo. This material was purified by flash silica column chromatography (Biotage Horizon system, EtOAc/hex gradient, 12+M column). This afforded the product which was dried in a 50° C. vacuum oven overnight to give the desired product.

TABLE II

| Example | Structure | Name | Method | LCMS Data |
|---|---|---|---|---|
| 73 | 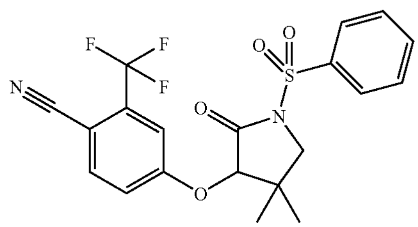 | 4-(1-Benzenesulfonyl-4,4-dimethyl-2-oxo-pyrrolidin-3-yloxy)-2-trifluoromethyl-benzonitrile | | |
| 74 | 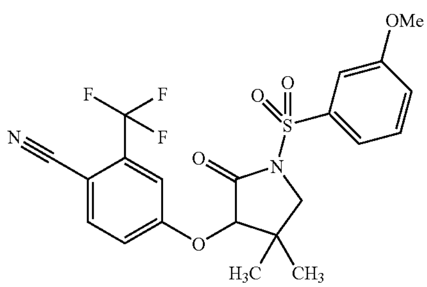 | 4-[1-(3-Methoxy-benzenesulfonyl)-4,4-dimethyl-2-oxo-pyrrolidin-3-yloxy]-2-trifluoromethyl-benzonitrile | A | MS (APCI, M − 1) 367.1<br>LCMS: 50-2% $H_2O$, 214 nm, 3.218 min, 100% |
| 75 | 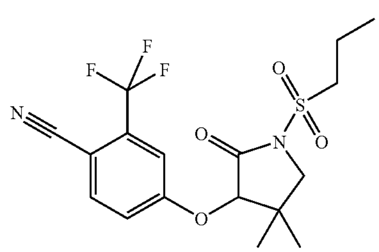 | 4-[4,4-Dimethyl-2-oxo-1-(propane-1-sulfonyl)-pyrrolidin-3-yloxy]-2-trifluoromethyl-benzonitrile | B | MS (APCI, M + 1): 405<br>Microanalysis C17H19F3N2O4S1<br>Theory C (50.49%), H (4.74%), N (6.93%)<br>Found C (50.44%), H (4.62%), N (6.73%) |
| 76 | 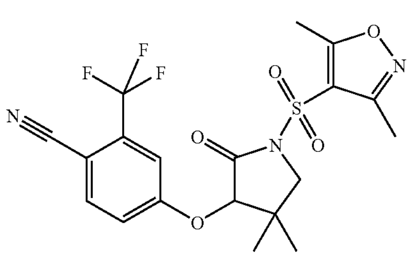 | 4-[1-(3,5-Dimethyl-isoxazole-4-sulfonyl)-4,4-dimethyl-2-oxo-pyrrolidin-3-yloxy]-2-trifluoromethyl-benzonitrile | B | LCMS (7): 4.20 min, 98.63%, 457.0 |

TABLE II-continued

| Example | Name | Method | LCMS Data |
|---|---|---|---|
| 77 | 4-[1-(3,5-Dimethyl-1H-pyrazole-4-sulfonyl)-4,4-dimethyl-2-oxo-pyrrolidin-3-yloxy]-2-trifluoromethyl-benzonitrile | B | LCMS (7): 3.74 min, 94.51%, 456.1 |
| 78 | 4-(1-Ethanesulfonyl-4,4-dimethyl-2-oxo-pyrrolidin-3-yloxy)-2-trifluoromethyl-benzonitrile | B | LCMS: 389 M − 1<br>Microanalysis C16H17F3N2O4S1<br>Theory C (48.75%), H (4.45%), N (7.11%)<br>Found C (48.37%), H (4.18%), N (6.93%) |
| 79 | 4-[4,4-Dimethyl-2-oxo-1-(propane-2-sulfonyl)-pyrrolidin-3-yloxy]-2-trifluoromethyl-benzonitrile | B | MS (APCI, M + 1): 405<br>Microanalysis C17H19F3N2O4S1<br>Theory C (50.42%), H (4.74%), N (6.92%)<br>Found C (50.19%), H (4.55%), N (6.68%) |
| 80 | 4-[1-(3-Fluoro-benzenesulfonyl)-4,4-dimethyl-2-oxo-pyrrolidin-3-yloxy]-2-trifluoromethyl-benzonitrile | B | MS (APCI, M + 1): 457<br>Microanalysis C17H19F3N2O4S1<br>Theory C (51.77%), H (3.66%), N (6.04%)<br>Found C (51.39%), H (3.45%), N (6.32%) |
| 81 | 4-(1-methanesulfonyl-4,4-dimethyl-2-oxo-pyrrolidin-3-yloxy)-2-trifluoromethyl-benzonitrile | B | LCMS 10 - 2% H$_2$O;<br>214 nm, 0.859 min. 100%, M + 1 377.0 |
| 82 | (+)-4-[4,4-Dimethyl-2-oxo-1-(propane-1-sulfonyl)-pyrrolidin-3-yloxy]-2-trifluoromethyl-benzonitrile | B | MS (APCI, M − 1): 403<br>LCMS 50 - 2% H$_2$O; 214 nm, 3.02 min. 100%, M − 1 403.0<br>Optical Rotation = +180.4 degrees in MeOH. |

TABLE II-continued

| Example | Structure | Name | Method | LCMS Data |
|---|---|---|---|---|
| 83 | 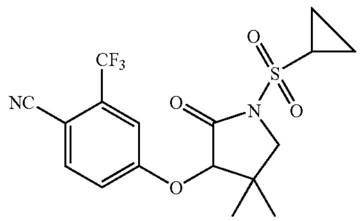 | 4-(1-Cyclopropanesulfonyl-4,4-dimethyl-2-oxo-pyrrolidin-3-yloxy)-2-trifluoromethyl-benzonitrile | B | MS (APCI, M + 1): 403<br>Microanalysis C17H17F3N2O4S1<br>Theory C (50.74%), H (4.26%), N (6.96%)<br>Found C (50.47%), H (4.25%), N (6.78%) |
| 84 | 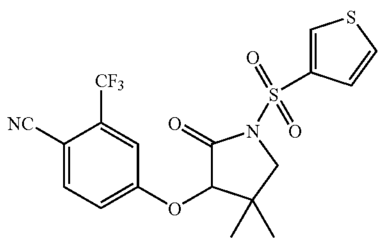 | 4-[4,4-Dimethyl-2-oxo-1-(thiophene-3-sulfonyl)-pyrrolidin-3-yloxy]-2-trifluoromethyl-benzonitrile | B | MS (APCI, M + 1): 445<br>LCMS 50 - 2% H$_2$O; 214 nm, 3.10 min. 100%, M − 1 443.0 |
| 85 | 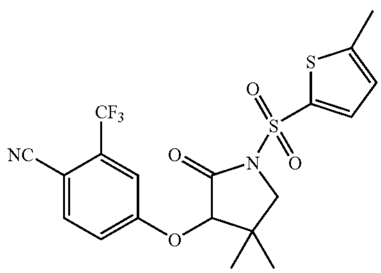 | 4-[4,4-Dimethyl-1-(5-methyl-thiophene-2-sulfonyl)-2-oxo-pyrrolidin-3-yloxy]-2-trifluoromethyl-benzonitrile | B | MS (APCI, M + 1): 459<br>Microanalysis C19H17F3N2O4S2<br>Theory C (49.68%), H (3.75%), N (6.10%)<br>Found C (49.43%), H (3.62%), N (5.98%) |
| 86 | 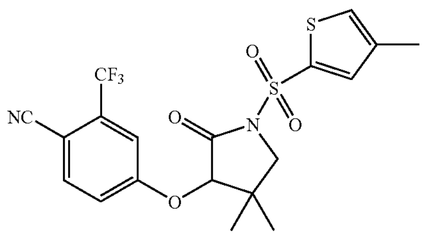 | 4-[4,4-Dimethyl-1-(4-methyl-thiophene-2-sulfonyl)-2-oxo-pyrrolidin-3-yloxy]-2-trifluoromethyl-benzonitrile | B | MS (APCI, M + 1): 459<br>Microanalysis C19H17F3N2O4S2<br>Theory C (49.78%), H (3.74%), N (6.11%)<br>Found C (49.48%), H (3.53%), N (5.97%) |
| 87 | 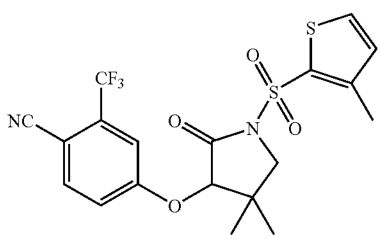 | 4-[4,4-Dimethyl-1-(3-methyl-thiophene-2-sulfonyl)-2-oxo-pyrrolidin-3-yloxy]-2-trifluoromethyl-benzonitrile | B | MS (APCI, M + 1): 459<br>Microanalysis C19H17F3N2O4S2<br>Theory C (49.78%), H (3.74%), N (6.11%)<br>Found C (49.52%), H (3.35%), N (5.99%) |
| 88 | 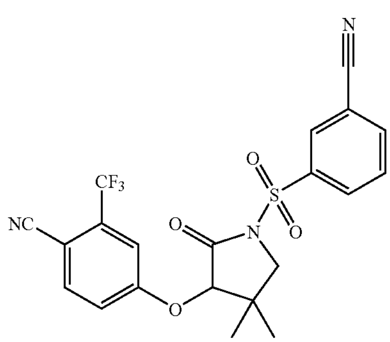 | 4-[1-(3-Cyano-benzenesulfonyl)-4,4-dimethyl-2-oxo-pyrrolidin-3-yloxy]-2-trifluoromethyl-benzonitrile | B | MS: 464 M + 1<br>Microanalysis C21H16F3N3O4S1<br>Theory C (54.43%), H (3.48%), N (9.07%)<br>Found C (54.35%), H (3.22%), N (8.84%) |

TABLE II-continued

| Example | Structure | Name | Method | LCMS Data |
|---|---|---|---|---|
| 89 | 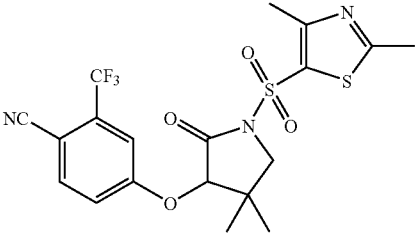 | 4-[1-(2,4-Dimethyl-thiazole-5-sulfonyl)-4,4-dimethyl-2-oxo-pyrrolidin-3-yloxy]-2-trifluoromethyl-benzonitrile | B | MS: 474 M + 1<br>Microanalysis C19H18F3N3O4S2<br>Theory C (48.20%), H (3.83%), N (8.87%)<br>Found C (48.23%), H (3.53%), N (8.66%) |
| 90 | 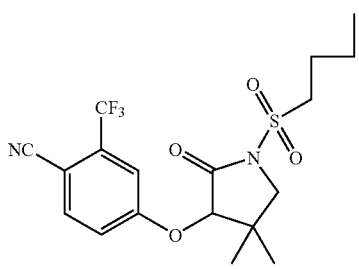 | 4-[1-(Butane-1-sulfonyl)-4,4-dimethyl-2-oxo-pyrrolidin-3-yloxy]-2-trifluoromethyl-benzonitrile | B | MS: 419 M + 1 LCMS 50 - 2% $H_2O$;<br>214 nm, 3.36 min. 100%, M − 1 417.0 |
| 91 | 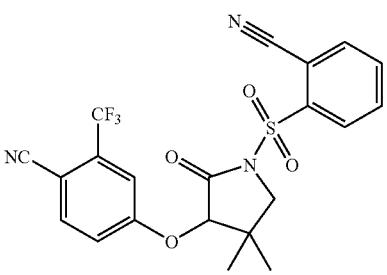 | 4-[1-(2-Cyano-benzenesulfonyl)-4,4-dimethyl-2-oxo-pyrrolidin-3-yloxy]-2-trifluoromethyl-benzonitrile | B | MS: 462 M − 1 LCMS 50 - 2% $H_2O$;<br>214 nm, 3.17 min. 100%, M − 1 462.0 |
| 92 | 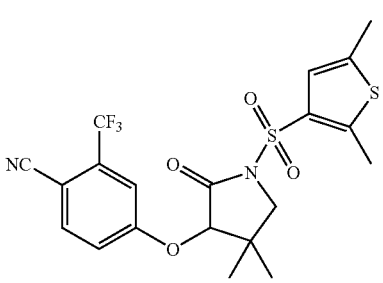 | 4-[1-(2,5-Dimethyl-thiophene-3-sulfonyl)-4,4-dimethyl-2-oxo-pyrrolidin-3-yloxy]-2-trifluoromethyl-benzonitrile | B | MS: 473 M + 1 Prep. LCMS 85 - 0% $H_2O$;<br>210-260 nm Average, 8.85 min.<br>100%, M = 472.0 |
| 93 | 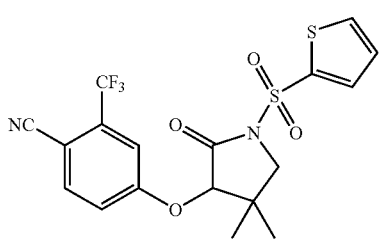 | 4-[4,4-Dimethyl-2-oxo-1-(thiophene-2-sulfonyl)-pyrrolidin-3-yloxy]-2-trifluoromethyl-benzonitrile | B | MS: 445 M + 1<br>Microanalysis C18H15F3N2O4S2<br>Theory C (48.64%), H (3.40%), N (6.30%)<br>Found C (48.62%), H (3.21%), N (6.04%) |
| 94 | 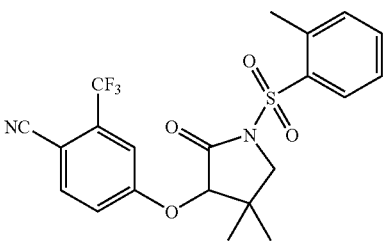 | 4-[4,4-Dimethyl-2-oxo-1-(toluene-2-sulfonyl)-pyrrolidin-3-yloxy]-2-trifluoromethyl-benzonitrile | B | MS: 453 M + 1 LCMS: 50 - 2% $H_2O$;<br>254 nm, 3.51 min. 97.8%, M − 2 451 |

TABLE II-continued

| Example | Name | Method | LCMS Data |
|---|---|---|---|
| 99 | 4-(4,4-Dimethyl-1-methylsulfanylmethyl-2-oxo-pyrrolidin-3-yloxy)-2-trifluoromethyl-benzonitrile | B | MS: 359 M + 1 LCMS: 50 - 2% H2O; 254 nm, 3.02 min. 96.8% |
| 100 | 4-(1-Methanesulfonyl-4,4-dimethyl-2-oxo-pyrrolidin-3-yloxy)-2-trifluoromethyl-benzonitrile | B | MS: 377 M + 1 LCMS: 50 - 2% $H_2O$; 254 nm, 2.33 min. 96.2%, M − 1 375 Optical Rotation = +179.2 degrees in MeOH. |
| 100A | 5-[3-(4-Cyano-3-trifluoromethyl-phenoxy)-4,4-dimethyl-2-oxo-pyrrolidine-1-sulfonyl]-furan-2-carboxylic acid methyl ester | B | MS: 486 M Microanalysis C20H17F3N2O7S1 Theory C (49.39%), H (3.52%), N (5.76%) Found C (49.76%), H (3.67%), N (5.51%) |
| 100B | 4-(4,4-Dimethyl-1-methylsulfanylmethyl-2-oxo-pyrrolidin-3-yloxy)-2-trifluoromethyl-benzonitrile | B | MS: 359 M + 1 LCMS: 50 - 2% $H_2O$; 254 nm, 2.81 min. 99.7% Optical Rotation = +196.1 degrees in MeOH. |
| 100C | 4-(1-Cyclopropanesulfonyl-4,4-dimethyl-2-oxo-pyrrolidin-3-yloxy)-2-trifluoromethyl-benzonitrile | B | MS: 401 M − 1 LCMS: 50 - 2% $H_2O$; 254 nm, 2.67 min. 98.8% Optical Rotation = +183.5 degrees in MeOH. |
| 100D | 4-(1-Methanesulfonyl-4,4-dimethyl-2-oxo-pyrrolidin-3-yloxy)-2-methoxy-benzonitrile | B | MS: 339 M + 1 LCMS: 50 - 2% $H_2O$; 254 nm, 1.77 min. 98.3% |
| 100E | 4-[1-(2-Ethyl-butyryl)-4,4-dimethyl-2-oxo-pyrrolidin-3-yloxy]-2-trifluoromethyl-benzonitrile | B | MS: 397.1 M + 1, M − 1 395.1. LCMS 50 - 2% $H_2O$; 254 nm, 14.67 min. 100%. |

TABLE II-continued

| Example | Structure | Name | Method | LCMS Data |
|---|---|---|---|---|
| 100F | 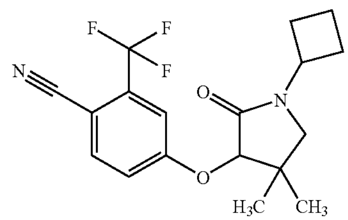 | 4-(1-Cyclobutyl-4,4-dimethyl-2-oxo-pyrrolidin-3-yloxy)-2-trifluoromethyl-benzonitrile | B | M + 1 = 353 (rt = 2.58 min, LC/MS 50% method, purity = 93%) |

Example 95

4-[1-(3-Hydroxy-benzenesulfonyl)-4,4-dimethyl-2-oxo-pyrrolidin-3-yloxy]-2-trifluoromethyl-benzonitrile The compound obtained in Example 74, 4-[1-(3-methoxy-benzenesulfonyl)-4,4-dimethyl-2-oxo-pyrrolidin-3-yloxy]-2-trifluoromethyl-benzonitrile, (0.093 g, 0.20 mmol) was demethylated as described in the general demethylation procedure of Example 8.

MS (APCl, M−1): 453.0
LCMS: 50-2% $H_2O$, 214 nm, 2.642 min, 100%
LCMS: 50-2% $H_2O$, 254 nm, 2.642 min, 96.7%

Example 96

(+)-4-(1-Methanesulfonyl-4,4-dimethyl-2-oxo-pyrrolidin-3-yloxy)-2-trifluoromethyl-benzonitrile The product of example 96 was prepared resolving the enantiomers produced in example 81 by chiral HPLC MS (APCl, M+1) 377.0
LCMS: 10-2% $H_2O$; 214 nm, 0.859 min. 100%,

Example 97

(+/−) 4-{1-Benzoyl-4,4-dimethyl-2-oxo-pyrrolin-3-yloxy)-2-trifluoromethyl benzonitrile}

To a stirring solution of 4-(4,4-dimethyl-2-oxo-pyrrolidin-3-yloxy)-2-trifluoromethyl-benzonitrile (Product of Example 3, 250 mg, 0.84 mmol) in anhydrous THF (5 mL) was added NaH (40 mg, 1 mmol) under $N_2$ at RT(room temperature). After stirring for 15 minutes, benzoyl chloride was added (0.14 mL, 1 mmol) as a solution in THF (1 mL). After stirring at RT overnight sat. $NH_4Cl$ (25 mL) and ethyl acetate (150 mL) were added. The separated organic phase was treated with brine and dried over MgSO4. The solution was then filtered, concentrated down, and purified by column chromatography (small Biotage silica gel column, 2:1 Hex/EA). Combined cleanest fractions to afford the desired product as a white solid.

MS (APCl, M+1) 401 LCMS: 50-2% $H_2O$, 214 nm, 3.31 min, 100%

Example 98

4-(1-Cyclopentyl-4,4-dimethyl-2-oxo-pyrrolidin-3-yloxy)-2-trifluoromethyl-benzonitrile The product of Example 98 was prepared analogously to Example 1, except that cyclohexylamine was used in Step B instead of (S)-(+)-sec-butylamine.

MS (APCl, M+1) 367 LCMS: 50-2% $H_2O$, 214 nm, 3.43 min, 100%

Example 101

4-(4,4-Dimethyl-2-oxo-1-phenylacetyl-pyrrolidin-3-yloxy)-2-trifluoromethyl-benzonitrile The product of example 101 was produced analogously to Example 97 except that phenethyl chloride was substituted for benzoyl chloride in Step E, the functionalization reaction.

MS (APCl, M+1)$_{415}$ LCMS: 50-2% $H_2O$, 214 nm, 3.58 min, 100%

Example 102

4-(1-Butyryl-4,4-dimethyl-2-oxo-pyrrolidin-3-yloxy)-2-trifluoromethyl-benzonitrile The product of example 102 was produced analogously to Example 97 except that butyryl chloride was substituted for benzoyl chloride in Step E, the functionalization reaction.

MS (APCl, M+1) 367 LCMS: 50-2% $H_2O$, 214 nm, 3.44 min, 100%

Example 103

(+)-4-(1-Butyryl-4,4-dimethyl-2-oxo-pyrrolidin-3-yloxy)-2-trifluoromethyl-benzonitrile (single enantiomer);

The product of Example 103 was generated by submitting the product of Example 102 to a chiral separation MS (APCl, M+1) 367 LCMS: 50-2% $H_2O$, 214 nm, 3.44 min, 100%

Example 104

4-[1-(4-Cyano-benzoyl)-4,4-dimethyl-2-oxo-pyrrolidin-3-yloxy]-2-trifluoromethyl-benzonitrile The product of example 104 was produced analogously to Example 97 except that 4-cyano-benzoyl chloride was substituted for benzoyl chloride in Step E, the functionalization reaction.

MS (APCl, M+1) 426 LCMS: 50-2% $H_2O$, 214 nm, 3.14 min, 100%

Example 105

(+)-4-(1-Benzoyl-4,4-dimethyl-2-oxo-pyrrolidin-3-yloxy)-2-trifluoromethyl-benzonitrile The product of Example 103 was generated by submitting the product of Example 97 to a chiral separation
MS (APCl, M+1) 401 LCMS: 50-2% H$_2$O, 214 nm, 3.31 min, 100%

Example 106

4-[1-(3,5-Dimethyl-isoxazole-4-carbonyl)-4,4-dimethyl-2-oxo-pyrrolidin-3-yloxy]-2-trifluoromethyl-benzonitrile The product of example 106 was produced analogously to Example 97 except that 3,5-Dimethyl-isoxazole-4-carbonyl chloride was substituted for benzoyl chloride in Step E, the functionalization reaction.
MS (APCl, M+1) 422 LCMS: 50-2% H$_2$O, 214 nm, 3.06 min, 100%

Example 107

4-[1-(3-Cyano-benzoyl)-4,4-dimethyl-2-oxo-pyrrolidin-3-yloxy]-2-trifluoromethyl-benzonitrile The product of example 107 was produced analogously to Example 97 except that 3-cyano-benzoyl chloride was substituted for benzoyl chloride in Step E, the functionalization reaction.
MS (APCl, M+1) 426 LCMS: 50-2% H$_2$O, 214 nm, 2.96 min, 100%

Example 108

4-[4,4-Dimethyl-2-oxo-1-(thiophene-2-carbonyl)-pyrrolidin-3-yloxy]-2-trifluoromethyl-benzonitrile The product of example 108 was produced analogously to Example 97 except that thiophene-2-carbonyl chloride was substituted for benzoyl chloride in Step E, the functionalization reaction
LCMS (6): 5.88 min, 100%, 408.0

Example 109

3-Chloro-4-[4,4-dimethyl-2-oxo-1-(1-phenyl-ethyl)-pyrrolidin-3-yloxy]-benzonitrile Step A: Ether Formation
To a stirring solution of (+/−)-pantolactone (2.8 g, 21.0 mmol, Aldrich) in DMF (39 mL) at 0° C. was added NaH (887 mg, 22.2 mmol, 60% dispersion in mineral oil) portion-wise under a nitrogen atmosphere. After gas evolution ceased, 3-chloro-4-fluorobenzonitrile (3.0 g, 19.3 mmol, Aldrich) was added. The resulting mixture was allowed to warm to ambient temperature over 19 hours. The reaction mixture was quenched with saturated aqueous NH$_4$Cl and diluted with EtOAc "ethylacetate". The layers were separated and the organic layer washed with additional saturated aqueous NH$_4$Cl followed by brine. The organics were dried (MgSO$_4$), filtered, and concentrated in vacuo. The resulting white solid was purified by flash chromatography (5% to 50% EtOAc/hexanes) to afford 2.9 g (56%) of the desired aryl ether as a white solid. MS (AP−)=264.0; LCMS purity=100%, t$_R$=2.307 (50% to 2% H$_2$O+0.1% HCO$_2$H/CH$_3$CN+0.1% HCO$_2$H, 4 min run time).

Step B Amidation:
The product of step A (1.0 g, 3.8 mmol) was dissolved in THF (5 mL) and (S)-(−)-α-methylbenzylamine (684 mg, 5.6 mmol, 0.72 mL) added in one portion. The resulting solution was heated at 65° C. over 48 hours. The reaction mixture was cooled to ambient temperature and diluted with EtOAc. The organics were washed with saturated aqueous NH$_4$Cl (2×) followed by brine. The organic layer was dried (MgSO$_4$), filtered, and concentrated in vacuo. Purification by flash chromatography (10% to 60% EtOAc/hexanes) afforded 2-(2-chloro-4-cyano-phenoxy)-4-hydroxy-3,3-dimethyl-N-(1-phenyl-ethyl)-butyramide as a white foam (1.3 g, 91%). MS (AP+)=387.1; MS (AP−)=385.1; LCMS purity=92%, t$_R$=2.426 (50% to 2% H$_2$O+0.1% HCO$_2$H/CH$_3$CN+0.1% HCO$_2$H, 4 min run time).

Step C: Displacement
The product of step B (1.3 g, 3.4 mmol) was dissolved in pyridine (7.1 mL) and cooled to 0° C. Mesyl chloride (586 mg, 5.1 mmol, 0.4 mL) was added slowly and the resulting solution allowed to warm to ambient temperature over 2.5 hours. The reaction mixture was diluted with 1 M HCl/EtOAc (100 mL, 1:1). The layers were separated and the organic layer washed with additional 1 M HCl and brine. The organics were dried (MgSO$_4$), filtered, and concentrated in vacuo to afford 1.5 g (96%) of methanesulfonic acid 3-(2-chloro-4-cyano-phenoxy)-2,2-dimethyl-3-(1-phenyl-ethylcarbamoyl)-propyl ester as a colorless oil. MS (AP+)=465.1; MS (AP−)=464.0; LCMS purity=100%, t$_R$=2.592 (50% to 2% H$_2$O+0.1% HCO$_2$H/CH$_3$CN+0.1% HCO$_2$H, 4 min run time).

Step D: Ring Closure
The product of step C (1.5 g, 3.3 mmol) was dissolved in THF (32 mL) at ambient temperature under a nitrogen atmosphere. NaH (327 mg, 8.2 mmol, 60% dispersion in mineral oil) was added in 3 portions and the resulting mixture stirred over 6 days. The reaction mixture was quenched with saturated aqueous NH$_4$Cl and diluted with EtOAc. The layers were separated and the organic layer washed with additional saturated aqueous NH$_4$Cl followed by brine. The organics were dried (MgSO$_4$), filtered, and concentrated in vacuo. The two diastereomers were separated by flash chromatography (10% to 50% EtOAc/hexanes). The desired diastereomer was the more non-polar isomer. After separating the desired diastereomer, the compound was further purified by RPHPLC (50:50 to 2:98 H$_2$O/TFA:CH$_3$CN, 254nM). Collect fractions at 21:79, t$_R$=35.3 min. The fractions were concentrated to afford 3-chloro-4-[4,4-dimethyl-2-oxo-1-(1-phenyl-ethyl)-pyrrolidin-3-yloxy]-benzonitrile as a white solid (440 mg, 36%). MS (AP+)=369.1; LCMS purity=100%, t$_R$=3.568 (50% to 2% H$_2$O+0.1% HCO$_2$H/CH$_3$CN+0.1% HCO$_2$H, 4 min run time); [α]25D=+43.6 (c 0.0066 EtOH).

Example 110

4-[4,4-Dimethyl-2-oxo-1-(1-phenyl-ethyl)-pyrrolidin-3-yloxy]-2-methoxy-benzonitrile Step A: Ether Formation
To a stirring solution of (+/−)-pantolactone (2.1 g, 16.0 mmol, Aldrich) in THF (65 mL) at 0° C. was added NaH (790 mg, 20.0 mmol, 60% dispersion in mineral oil) portion-wise under a nitrogen atmosphere. After gas evolution ceased, 4-fluoro-2-methoxybenzonitrile (2.0 g, 13.0 mmol, Oakwood Products) was added. The resulting mixture was allowed to warm to ambient temperature over 19 hours. The reaction mixture was quenched with saturated aqueous NH₄Cl and diluted with EtOAc. The layers were separated and the organic layer washed with additional saturated aqueous NH₄Cl followed by brine. The organics were dried (MgSO₄), filtered, and concentrated in vacuo. The resulting white solid was purified by flash chromatography (10% to 60% EtOAc/hexanes) to afford 2.7 g of 4-(4,4-dimethyl-2-oxo-tetrahydro-furan-3-yloxy)-2-methoxy-benzonitrile as a white foam. MS (AP+)=262.1; LCMS purity=100%, $t_R$=1.892 (50% to 2% H₂O+0.1% HCO₂H/CH₃CN+0.1% HCO₂H, 4 min run time).

Step B: Amidation

The product of step A (856 mg, 3.3 mmol) was dissolved in THF (5 mL) and (S)-(−)-α-methylbenzylamine (596 mg, 4.9 mmol, 0.63 mL) added in one portion. The resulting solution was heated at 80° C. over 48 hours. The reaction mixture was cooled to ambient temperature and diluted with EtOAc. The organics were washed with saturated aqueous NH₄Cl (2×) followed by brine. The organic layer was dried (MgSO₄), filtered, and concentrated in vacuo. Purification by flash chromatography (30% to 100% EtOAc/hexanes) afforded 2-(4-cyano-3-methoxy-phenoxy)-4-hydroxy-3,3-dimethyl-N-(1-phenyl-ethyl)-butyramide as a white solid (920 mg). MS (AP+)=383.2; MS (AP−)=381.2; LCMS purity=100%, $t_R$=1.975 (50% to 2% H₂O+0.1% HCO₂H/CH₃CN+0.1% HCO₂H, 4 min run time).

Step C: Displacement

The product of step B (920 mg, 2.4 mmol) was dissolved in pyridine (5.1 mL) and cooled to 0° C. Mesyl chloride (413 mg, 3.6 mmol, 0.28 mL) was added slowly and the resulting solution allowed to warm to ambient temperature over 2 hours. The reaction mixture was diluted with 1 M HCl/EtOAc (100 mL, 1:1). The layers were separated and the organic layer washed with additional 1 M HCl and brine. The organics were dried (MgSO₄), filtered, and concentrated in vacuo to afford 1.1 g of methanesulfonic acid 3-(4-cyano-3-methoxy-phenoxy)-2,2-dimethyl-3-(1-phenyl-ethylcarbamoyl)-propyl ester as a colorless oil. MS (AP+)=461.1; LCMS purity=100%, $t_R$=2.363 (50% to 2% H₂O+0.1% HCO₂H/CH₃CN+0.1% HCO₂H, 4 min run time).

Step D: Ring Closure

The product of Step C (1.0 g, 2.3 mmol) was dissolved in THF (23 mL) at ambient temperature under a nitrogen atmosphere. NaH (226 mg, 5.6 mmol, 60% dispersion in mineral oil) was added in 3 portions and the resulting mixture heated at reflux over 18 hours. The reaction mixture was quenched with saturated aqueous NH₄Cl and diluted with EtOAc. The layers were separated and the organic layer washed with additional saturated aqueous NH₄Cl followed by brine. The organics were dried (MgSO₄), filtered, and concentrated in vacuo. The diastereomers were purified, not separated, by RPHPLC (50:50 to 10:90 H₂O/TFA:CH₃CN, 254 nM). Collect fractions at 23:77, $t_R$=21.0 min. The fractions were concentrated and the diastereomers separated by flash chromatography (5% to 55% EtOAc/hexanes). The desired diastereomer was the more non-polar isomer. The fractions were concentrated to afford 4-[4,4-dimethyl-2-oxo-1-(1-phenyl-ethyl)-pyrrolidin-3-yloxy]-2-methoxy-benzonitrile as a colorless oil (130 mg). MS (AP+)=365.2; LCMS purity=100%, $t_R$=2.945 (50% to 2% H₂O+0.1% HCO₂H/CH₃CN+0.1% HCO₂H, 4 min run time).

Examples 111-127

Examples 111-127 illustrate the preparation of a series of compounds of Formula I, in which $R^1$ is represented by a series of oxadiazoles. These compounds were prepared by the reaction scheme described below. Compound #1 (below) was produced as described in Example 3. This compound was then contacted with bromoacetic acid ethyl ester(2) to generate compound (3) bearing an acetyl ester at the nitrogen atom of the lactam as described in Step 1. In step 2, this ester function was removed leaving the free acid available for reaction. Seventeen (17) individual aliquots of compound 3 were removed from the reaction mixture and they were reacted with the appropriate acyl hydrazide to produce the desired oxadiazole derivative of Formula I using the procedure described in Step 3.

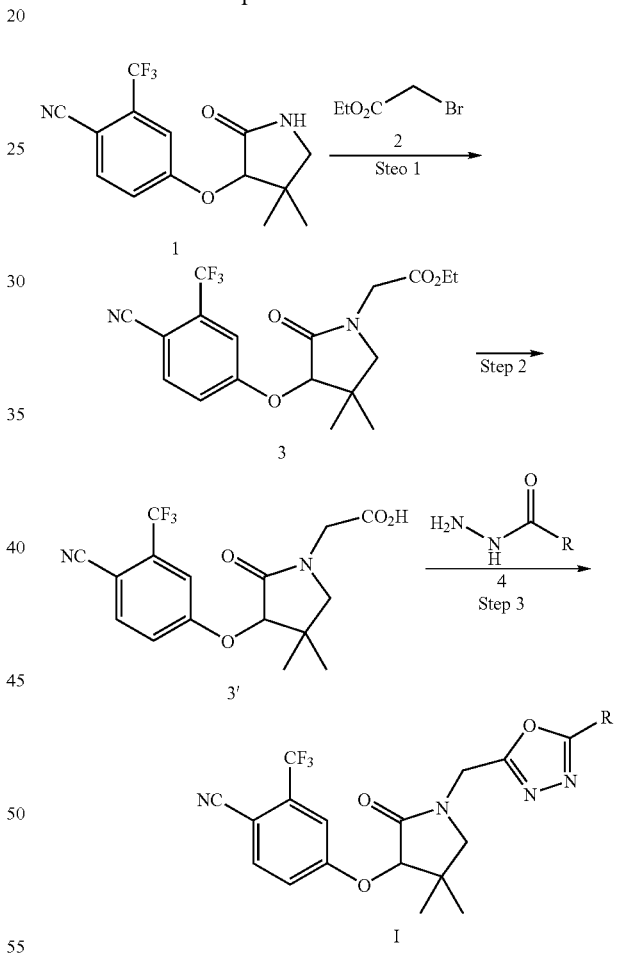

Step 1:

Preparation of [3-(4-Cyano-3-trifluoromethyl-phenoxy)-4,4-dimethyl-2-oxo-pyrrolidin-1-yl]-acetic acid ethyl ester To a −78° C. stirring solution of 4-(4,4-Dimethyl-2-oxo-pyrrolidin-3-yloxy)-2-trifluoromethyl-benzonitrile (Compound (1), product of Example 3, Step E, 5.00 g, 16.8 mmoles) in 100 mL THF under a nitrogen atmosphere was added lithium bis(trimethylsilyl)amide (1 M in THF, 18.4 mL, 18.4 mmoles) and bromoacetic acid ethyl ester (2) (2.0 mL, 18.4 mmoles). The cooling bath was allowed to warm up to ambient temperature overnight. Water (25 mL) was added and the reaction mixture was concentrated in vacuo. Methylene chloride (100 mL) and water (50 mL) was added, the mixture is agitated and the layers are separated. The organic layer was concentrated in vacuo. The product (3) is used as is for the next reaction.

Step 2: Preparation of [3-(4-Cyano-3-trifluoromethyl-phenoxy)-4,4-dimethyl-2-oxo-pyrrolidin-1-yl]-acetic acid Sodium hydroxide (50% in water, 10 mL) was added to a stirring solution of [3-(4-cyano-3-trifluoromethyl-phenoxy)-4,4-dimethyl-2-oxo-pyrrolidin-1-yl]-acetic acid ethyl ester (3) (16.8 mmoles) in ethanol (50 mL) and water (40 mL). The reaction was stirred at ambient temperature overnight. The pH of reaction mixture was adjusted to 2.0 by adding hydrochloric acid (37% in water). The reaction mixture was concentrated in vacuo to remove the ethanol. The desired product (3') that precipitated from the residue was filtered and dried in a vacuum oven overnight.

Step 3: General Procedure for Oxadiazoles—Combinatorial synthesis 1,1-Carbonyldiimidazole (1.1 equivalents) was added to a solution of [3-(4-cyano-3-trifluoromethyl-phenoxy)-4,4-dimethyl-2-oxo-pyrrolidin-1-yl]-acetic acid (compound 3', 1 equivalent) in acetonitrile (40 mL) and dimethylformamide (20 mL). The reaction was stirred at ambient temperature 45 minutes. An aliquot of the reaction mixture was added to the acyl hydrazide(Compound 4, 0.150 mmoles, 1 eq) the mixture was stirred at 80° C. overnight. The reaction mixture was cooled to ambient temperature and 2-chloro-1,3-dimethylimidazolinium chloride (3 equivalents) and triethylamine (6 equivalents) was added. The mixture was stirred at 80° C. 6 hours. The reaction mixture was cooled to ambient temperature and the solvent was removed in vacuo. Methylene chloride and water were added, the mixture was agitated and the layers were separated. The organic layer was filtered through silica SPE. The filtrate was concentrated in vacuo and purified by preparative HPLC to give the desired product (I).

Preparative LCMS: indicated as LCMS (5) Sunfire C18 19×100 mm 5 um, flow rate 30 mL/min; 25% Acetonitrile with 0.1% formic acid/Water with 0.1% formic acid, hold for 1 min; gradient to 100% Acetonitrile with 0.1% formic acid over 6.5 minutes, hold for 4 minutes.

TABLE III

| Example | Structure | Name | LCMS, MS |
|---|---|---|---|
| 111 | 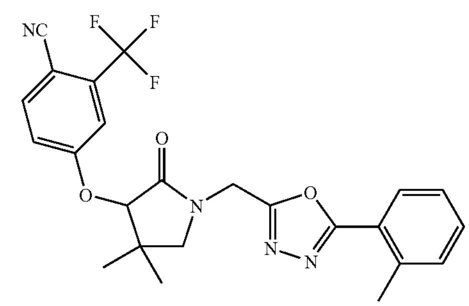 | 4-[4,4-Dimethyl-2-oxo-1-(5-o-tolyl-[1,3,4]oxadiazol-2-ylmethyl)-pyrrolidin-3-yloxy]-2-trifluoromethyl-benzonitrile | LCMS (5): 4.18 min, 100%, 470.4 |
| 112 | 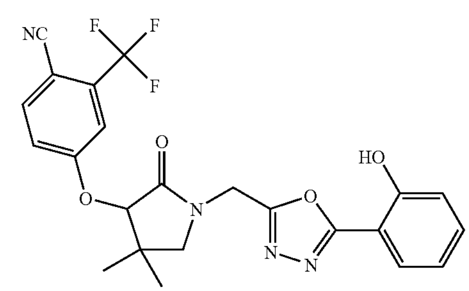 | 4-{1-[5-(2-Hydroxy-phenyl)-[1,3,4]oxadiazol-2-ylmethyl]-4,4-dimethyl-2-oxo-pyrrolidin-3-yloxy}-2-trifluoromethyl-benzonitrile | LCMS (5): 4.14 min, 100%, 472.4 |
| 113 | 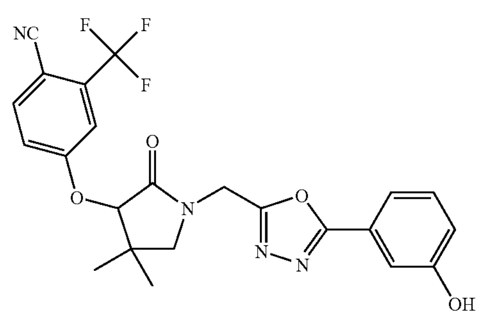 | 4-{1-[5-(3-Hydroxy-phenyl)-[1,3,4]oxadiazol-2-ylmethyl]-4,4-dimethyl-2-oxo-pyrrolidin-3-yloxy}-2-trifluoromethyl-benzonitrile | LCMS (5): 4.14 min, 100%, 472.4 |

TABLE III-continued

| Example | Structure | Name | LCMS, MS |
|---|---|---|---|
| 114 | 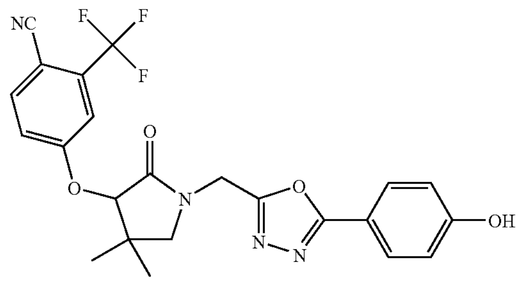 | 4-{1-[5-(4-Hydroxy-phenyl)-[1,3,4]oxadiazol-2-ylmethyl]-4,4-dimethyl-2-oxo-pyrrolidin-3-yloxy}-2-trifluoromethyl-benzonitrile | LCMS (5): 4.36 min, 100%, 472.4 |
| 115 | 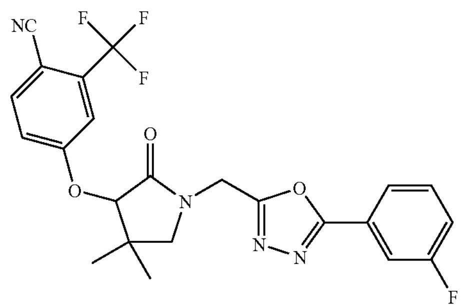 | 4-{1-[5-(3-Fluoro-phenyl)-[1,3,4]oxadiazol-2-ylmethyl]-4,4-dimethyl-2-oxo-pyrrolidin-3-yloxy}-2-trifluoromethyl-benzonitrile | LCMS (5): 4.09 min, 100%, 474.4 |
| 116 | 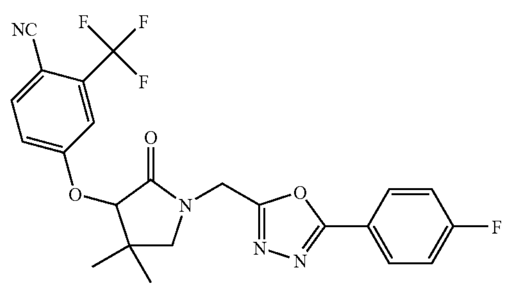 | 4-{1-[5-(4-Fluoro-phenyl)-[1,3,4]oxadiazol-2-ylmethyl]-4,4-dimethyl-2-oxo-pyrrolidin-3-yloxy}-2-trifluoromethyl-benzonitrile | LCMS (5): 4.09 min, 100%, 472.4 |
| 117 | 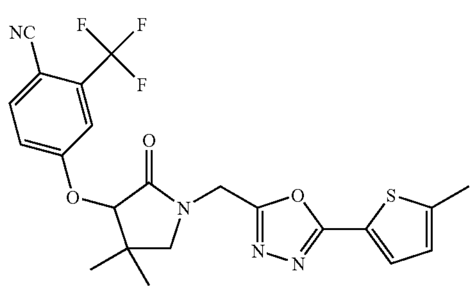 | 4-{4,4-Dimethyl-1-[5-(5-methyl-thiophen-2-yl)-[1,3,4]oxadiazol-2-ylmethyl]-2-oxo-pyrrolidin-3-yloxy}-2-trifluoromethyl-benzonitrile | LCMS (5): 4.02 min, 100%, 476.4 |
| 118 | 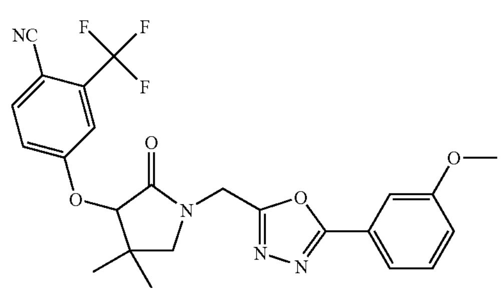 | 4-{1-[5-(3-Methoxy-phenyl)-[1,3,4]oxadiazol-2-ylmethyl]-4,4-dimethyl-2-oxo-pyrrolidin-3-yloxy}-2-trifluoromethyl-benzonitrile | LCMS (5): 4.07 min, 100%, 486.4 |

TABLE III-continued

| Example | Name | LCMS, MS |
|---|---|---|
| 119 | 4-{1-[5-(4-Methoxy-phenyl)-[1,3,4]oxadiazol-2-ylmethyl]-4,4-dimethyl-2-oxo-pyrrolidin-3-yloxy}-2-trifluoromethyl-benzonitrile | LCMS (5): 4.02 min, 100%, 486.4 |
| 120 | 4-{1-[5-(3-Chloro-phenyl)-[1,3,4]oxadiazol-2-ylmethyl]-4,4-dimethyl-2-oxo-pyrrolidin-3-yloxy}-2-trifluoromethyl-benzonitrile | LCMS (5): 4.23 min, 100%, 490.9 |
| 121 | 4-{1-[5-(2-Methoxy-phenyl)-[1,3,4]oxadiazol-2-ylmethyl]-4,4-dimethyl-2-oxo-pyrrolidin-3-yloxy}-2-trifluoromethyl-benzonitrile | LCMS (5): 3.90 min, 100%, 486.4 |
| 122 | 4-[4,4-Dimethyl-2-oxo-1-(5-m-tolyl-[1,3,4]oxadiazol-2-ylmethyl)-pyrrolidin-3-yloxy]-2-trifluoromethyl-benzonitrile | LCMS (5): 4.15 min, 100%, 470.4 |
| 123 | 4-{1-[5-(2,4-Dihydroxy-phenyl)-[1,3,4]oxadiazol-2-ylmethyl]-4,4-dimethyl-2-oxo-pyrrolidin-3-yloxy}-2-trifluoromethyl-benzonitrile | LCMS (5): 3.77 min, 96.7%, 488.4 |

TABLE III-continued

| Example | Name | LCMS, MS |
|---|---|---|
| 124 | 4-{1-[5-(3-Ethoxy-phenyl)-[1,3,4]oxadiazol-2-ylmethyl]-4,4-dimethyl-2-oxo-pyrrolidin-3-yloxy}-2-trifluoromethyl-benzonitrile | LCMS (5): 4.21 min, 100%, 500.5 |
| 125 | 4-{1-[5-(4-Chloro-phenyl)-[1,3,4]oxadiazol-2-ylmethyl]-4,4-dimethyl-2-oxo-pyrrolidin-3-yloxy}-2-trifluoromethyl-benzonitrile | LCMS (5): 4.21 min, 100%, 490.9 |
| 126 | 4-{4,4-Dimethyl-1-[5-(4-methyl-[1,2,3]thiadiazol-5-yl)-[1,3,4]oxadiazol-2-ylmethyl]-2-oxo-pyrrolidin-3-yloxy}-2-trifluoromethyl-benzonitrile | LCMS (5): 3.92 min, 100%, 478.5 |
| 127 | 4-{1-[5-(2-Chloro-phenyl)-[1,3,4]oxadiazol-2-ylmethyl]-4,4-dimethyl-2-oxo-pyrrolidin-3-yloxy}-2-trifluoromethyl-benzonitrile | LCMS (5): 4.13 min, 100%, 490.9 |

Examples 128-135

Examples 128-135 also illustrates the preparation of a series of compounds which $R_1$ is represented by a substituted oxadiazole. The reaction sequence utilized to produce these compounds is shown below:

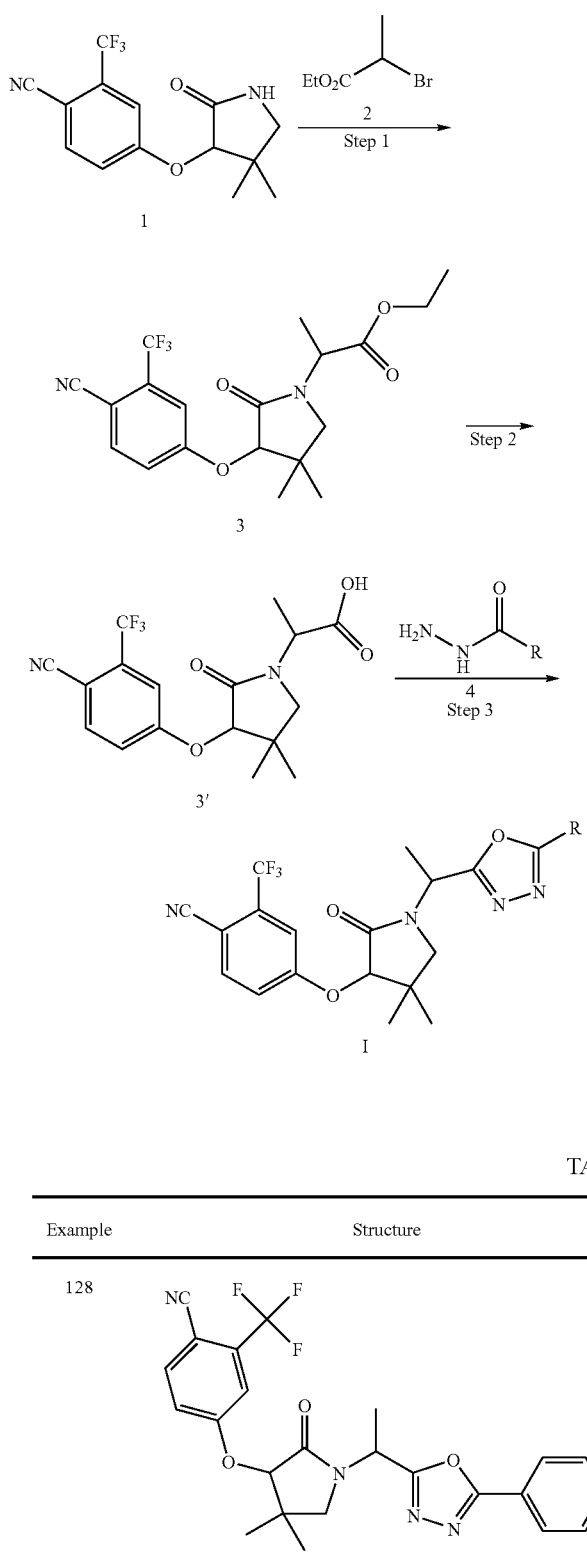

Step 1: Preparation of 2-[3-(4-Cyano-3-trifluoromethyl-phenoxy)-4,4-dimethyl-2-oxo-pyrrolidin-1-yl]-propionic acid ethyl ester The reaction was carried out as previously described in Step 1 of examples 111-127 using ethyl 2-bromopropionate in place of bromoacetic acid ethyl ester. The diastereomeric mixture of products (3) were separated by column chromatography to afford the diastereomers as either the RS or SR compound or the RR or SS compound. The RS or SR compound was used in the next reaction.

Step 2: Preparation of 2-[3-(4-Cyano-3-trifluoromethyl-phenoxy)-4,4-dimethyl-2-oxo-pyrrolidin-1-yl]-propionic acid The reaction was carried out as previously described in Step 2 of examples 111-127 to afford the acid (3').

Step 3: General Procedure for Oxadiazoles Synthesis

A solution of 2-[3-(4-cyano-3-trifluoromethyl-phenoxy)-4,4-dimethyl-2-oxo-pyrrolidin-1-yl]-propionic acid (compound 3', 1 equivalent) in methylene chloride (3 mL) was treated with 1,1-carbonyldiimidazole (1.1 equivalents) and the reaction was stirred at ambient temperature 1 hour. To this mixture was added the acyl hydrazide (Compound 4 in which R represents the substituent at the 5-position of the oxadiazole), 0.150 mmoles, 1 eq) and the mixture was stirred at 50° C. overnight. The reaction mixture was cooled to ambient temperature and 2-chloro-1,3-dimethylimidazolinium chloride (3 equivalents) and triethylamine (6 equivalents) was added and the reaction mixture stirred overnight at 50° C. The reaction mixture was cooled to ambient temperature and the solvent was removed in vacuo. Methylene chloride and water were added, the mixture was agitated and the layers were separated. The organic portion was concentrated in vacuo and purified by preparative HPLC to give the desired product (I).

HPLC purity was determined either on: (A) a 250×4 mm Wakosil C-18 column eluted with 80/20 acetonitrile/water (0.1% TFA), 1 mL/min, at 214 nM and 254 nM, or (B) a 150×60 mm Luna C-18 column eluted on a gradient of 80/20 acetonitrile/water (0.1% TFA) to 90/10 acetonitrile/water (0.1% TFA) over 15 minutes, 1 mL/min, at 214 nM and 254 nM.

TABLE IV

| Example | Structure | Name | HPLC, MS, CHN |
|---|---|---|---|
| 128 | (structure shown) | 4-[4,4-Dimethyl-2-oxo-1-[1-(5-phenyl-[1,3,4]oxadiazol-2-yl)-ethyl]-pyrrolidin-3-yloxy]-2-trifluoromethyl-benzonitrile | Method A<br>5.63 min, 98.2%<br>MS(APCI)<br>M + 1 = 471.1 |

TABLE IV-continued

| Example | Structure | Name | HPLC, MS, CHN |
|---|---|---|---|
| 129 | 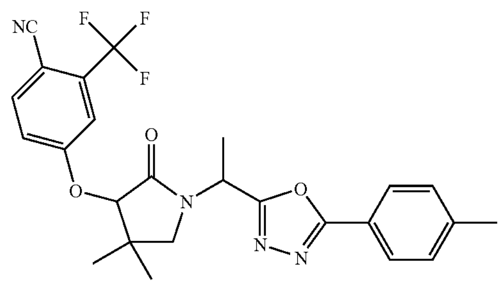 | 4-[4,4-Dimethyl-2-oxo-1-[1-(5-p-tolyl-[1,3,4]oxadiazol-2-yl)-ethyl]-pyrrolidin-3-yloxy]-2-trifluoromethyl-benzonitrile | MS(APCI) M + 1 = 485.1/486.1 |
| 130 | 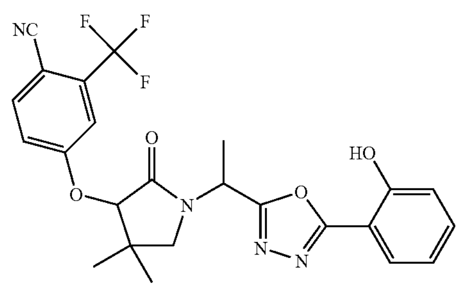 | 4-(1-{1-[5-(2-hydroxy-phenyl)-[1,3,4]oxadiazol-2-yl]-ethyl}-4,4-dimethyl-2-oxo-pyrrolidin-3-yloxy)-2-trifluoromethyl-benzonitrile | Method A 6.11 min, 95.0% MS(APCI) M + 1 = 487.1/488.2 |
| 132 | 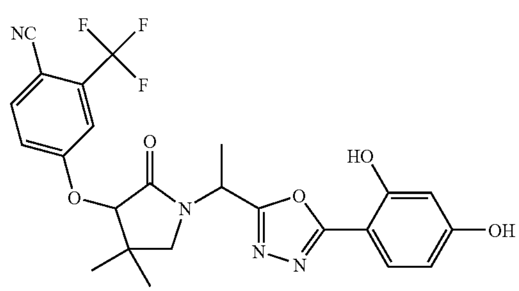 | 4-(1-{1-[5-(2,4-dihydroxy-phenyl)-[1,3,4]oxadiazol-2-yl]-ethyl}-4,4-dimethyl-2-oxo-pyrrolidin-3-yloxy)-2-trifluoromethyl-benzonitrile | Method A 4.81 min, 100% MS(APCI) M + 1 = 503.1/504.1 |
| 133 | 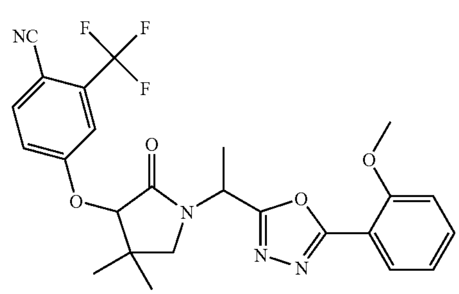 | 4-(1-{1-[5-(2-methoxy-phenyl)-[1,3,4]oxadiazol-2-yl]-ethyl}-4,4-dimethyl-2-oxo-pyrrolidin-3-yloxy)-2-trifluoromethyl-benzonitrile | Method A 5.17 min, 99% MS(APCI) M + 1 = 501.1/502.3 |
| 134 | 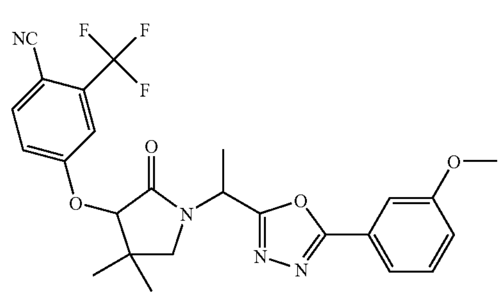 | 4-(1-{1-[5-(3-methoxy-phenyl)-[1,3,4]oxadiazol-2-yl]-ethyl}-4,4-dimethyl-2-oxo-pyrrolidin-3-yloxy)-2-trifluoromethyl-benzonitrile | Method A 6.25 min, 96% MS(APCI) M + 1 = 501.1/502.2 |

TABLE IV-continued

| Example | Structure | Name | HPLC, MS, CHN |
|---|---|---|---|
| 135 | 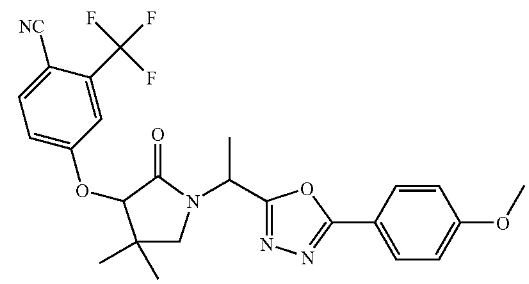 | 4-(1-{1-[5-(4-methoxy-phenyl)-[1,3,4]oxadiazol-2-yl]-ethyl}-4,4-dimethyl-2-oxo-pyrrolidin-3-yloxy)-2-trifluoromethyl-benzonitrile | Method A 5.84 min, 100% |

Example 136

The compounds of Formula I have affinity for the androgen receptor. This affinity has been demonstrated for selected compounds using the human receptor. The description below describes how the assay was carried out.

Competitive binding analysis was performed on baculovirus/Sf9 generated hAR extracts in the presence or absence of different concentrations of test agent and a fixed concentration of $^3$H-dihydrotestosterone ($^3$H-DHT) as tracer. This binding assay method is a modification of a protocol previously described (Liao S., et. al. *J. Steroid Biochem.* 20:11-17 1984). Briefly, progressively decreasing concentrations of compounds are incubated in the presence of hAR extract (Chang et al. *P.N.A.S.* Vol. 89, pp. 5546-5950, 1992), hydroxylapatite, and 1 nM 3H-DHT for one hour at 4° C. Subsequently, the binding reactions are washed three times to completely remove excess unbound 3H-DHT. hAR bound $^3$H-DHT levels are determined in the presence of compounds (i.e. competitive binding) and compared to levels bound when no competitor is present (i.e. maximum binding). Compound binding affinity to the hAR is expressed as the concentration of compound at which one half of the maximum binding is inhibited. Table I below provides the results that were obtained for selected compounds (reported data is the mean of multiple tests as shown below)

TABLE V

| Example | IC50 |
|---|---|
| 1 | 136 (c) |
| 2 | Same |
| 3 | 435 (a) |
| 4 | 188 (a) |
| 5 | 32 (a) |
| 6 | 31 (c) |
| 7 | 298 (a) |
| 8 | 17 (a) |
| 9 | 18 (a) |
| 10 | 298 (a) |
| 11 | 17 (a) |
| 12 | 111 (a) |
| 13 | 11 (a) |
| 14 | 23 (a) |
| 15 | 48 (a) |
| 16 | 26 (a) |
| 17 | 144 (a) |
| 18 | 45 (a) |
| 19 | 152 (c) |
| 20 | 97 (n = 6) |
| 21 | 403 (a) |
| 22 | 40 (a) |
| 23 | 64 (a) |

TABLE V-continued

| Example | IC50 |
|---|---|
| 24 | 10 (a) |
| 25 | 48 (c) |
| 26 | 343 (a) |
| 27 | 44 (a) |
| 28 | 310 (a) |
| 29 | 119 (c) |
| 30 | 215 (a) |
| 31 | 268 (a) |
| 32 | 420 (a) |
| 33 | 478 (a) |
| 34 | 437 (a) |
| 35 | 128 (a) |
| 36 | 484 (a) |
| 37 | 47 (c) |
| 38 | 326 (a) |
| 39 | 64 (a) |
| 40 | 43 (a) |
| 41 | 107 (a) |
| 42 | 120 (a) |
| 43 | 283 (a) |
| 44 | 346 (a) |
| 45 | 50 (a) |
| 46 | 90 (c) |
| 47 | 83 (a) |
| 48 | 109 (a) |
| 49 | 214 (a) |
| 50 | 152 (a) |
| 51 | 321 (a) |
| 52 | 160 (a) |
| 53 | 294 (a) |
| 54 | 217 (a) |
| 55 | 500 (a) |
| 56 | 171 (c) |
| 57 | 31 (a) |
| 58 | 313 (a) |
| 59 | 277 (a) |
| 60 | 115 (a) |
| 61 | 101 (c) |
| 62 | 293 (a) |
| 63 | 500 (a) |
| 64 | 254 (a) |
| 65 | 38 (a) |
| 66 | 142 (a) |
| 67 | 437 (a) |
| 68 | 133 (a) |
| 69 | 258 (a) |
| 70 | 52 (a) |
| 71 | 104 (a) |
| 72 | 203 (a) |
| 73 | 206 (a) |
| 74 | 106 (a) |
| 75 | 64 (a) |
| 76 | 430 (a) |
| 77 | 246 (a) |
| 78 | 103 (a) |

TABLE V-continued

| Example | IC50 |
|---|---|
| 79 | 305 (a) |
| 80 | 80 (a) |
| 81 | 139 (a) |
| 82 | 47 (c) |
| 83 | 50 (a) |
| 84 | 85 (a) |
| 85 | 233 (a) |
| 86 | 140 (a) |
| 87 | 115 (a) |
| 88 | 110 (a) |
| 89 | 281 (a) |
| 90 | 309 (a) |
| 91 | 508 (a) |
| 92 | 334 (a) |
| 93 | 82 (a) |
| 94 | 150 (a) |
| 95 | 8 (a) |
| 96 | 12 (a) |
| 97 | 311 (a) |
| 98 | 169 (a) |
| 99 | 113 (a) |
| 100 | 12 (a) |
| 101 | 174 (a) |
| 102 | 418 (a) |
| 103 | 130 (a) |
| 104 | 248 (a) |
| 105 | 252 (a) |
| 106 | 342 (a) |
| 107 | 68 (a) |
| 108 | 370 (a) |
| 109 | 203 (a) |
| 110 | 87 (a) |
| 111 | 239 (a) |
| 112 | 85 (2) |
| 113 | 224 (a) |
| 114 | 41 (a) |
| 115 | 142 (a) |
| 116 | 206 (a) |
| 117 | 259 (a) |
| 118 | 170 (a) |
| 119 | 80 (a) |
| 120 | 347 (a) |
| 121 | 131 (a) |
| 122 | 271 (a) |
| 123 | 61 (a) |
| 124 | 404 (a) |
| 125 | 250 (a) |
| 126 | 191 (a) |
| 127 | 198 (a) |
| 128 | 82 (a) |
| 129 | 63 (a) |
| 130 | 85 (a) |
| 132 | 52 (a) |
| 133 | 60 (a) |
| 134 | 76 (a) |
| 135 | 44 (a) |
| 4A | 230 (N = 6) |
| 4B | >10000 (c) |
| 100A | 242 (a) |
| 100B | 76 (a) |
| 100C | 59 (a) |
| 100D | 555 (a) |
| 100E | 372 (a) |
| 100F | 243 (a) |

(a) - mean of 2 tests
(b) - mean of 3 tests
(c) - mean of 4 tests
ND—not determined
UA—unavailable

Example 137

The compounds ability to antagonize the effects of androgen on the androgen receptor were determined in a whole cell assay as described immediately below.

Experimental Procedure for AR Antagonist Cell Assay

Cell line: MDA-MB453-MMTV clone 54-19. This cell line is a stable transfected cell line with MDA-MB453 cell background (a human breast tumor cell line expressing androgen receptor). A MMTV minimal promoter containing ARE was first cloned in front of a firefly luciferase reporter gene. Then the cascade was cloned into transfection vector pUV120puro. Electroporation method was used for transfecting MDA-MB-453 cell. Puromycin resistant stable cell line was selected.

Cell Culture Media and Reagents:

Culture medium: DMEM (high glucose, Gibco cat #: 11960-044), 10% FBS, and 1% L-glutamine Plating medium: DMEM (phenol red free), 10% charcoal treated HyClone serum, 1% L-glutamine Assay medium: DMEM (phenol red free), 1% charcoal treated HyClone serum, 1% L-glutamine, and 1% penicillin/streptomycin 3× luciferase buffer: 2% beta-mercaptoethanol, 0.6% ATP, 0.0135% luciferine in cell lysis buffer Assay Procedure:

Cells are maintained in culture medium, splitting cells when they reach 80-90% confluence To test compounds, 10,000 cells/well are plated to opaque 96 cell culture plate in 100 ul/well plating medium, culture for overnight at 37° C. in cell culture incubator Carefully remove plating medium, then add 80 ul/well of pre-warmed assay medium, add 10 ul/well testing compound (final concentration at) 1000 nM, 200 nM, 40 nM, 8 nM, 1.6 nM, and 0.32 nM), incubate at 37° C. for 30 minutes Add 10 ul/well freshly prepared DHT (final concentration at 100 pM) to each well, incubate at 37° C. for 17 hr (overnight) Add 50 ul/well 3× luciferase buffer, incubate at room temperature for 5 minutes, then count on Luminometer The fold induction over background by 100 pM DHT in the absence of testing compounds is standardized as 100% and experimental result is expressed as percentage of inhibition by testing compounds.

The results are described below in Table III. The results are reported as the mean of multiple tests as described below (the numbers of tests are indicated in the footnote). N.D. denotes that the compound was not tested.

TABLE VI

| Example | IC50 |
|---|---|
| 1 | 33 (c) |
| 2 | Same |
| 3 | ND |
| 4 | 26 (a) |
| 5 | 12 (a) |
| 6 | 136 (n = 6) |
| 7 | ND |
| 8 | 33 (a) |
| 9 | 46 (a) |
| 10 | ND |
| 11 | 14 (a) |
| 12 | 310 (a) |
| 13 | 313 (n = 6) |
| 14 | 99 (c) |
| 15 | 71 (c) |
| 16 | 43 (a) |
| 17 | 214 (c) |
| 18 | 8 (a) |
| 19 | 19 (a) |
| 20 | 13 (n = 6) |

TABLE VI-continued

| Example | IC50 |
|---|---|
| 21 | ND |
| 22 | 99 (a) |
| 23 | 58 (a) |
| 24 | 33 (a) |
| 25 | 107 (c) |
| 26 | ND |
| 27 | 368 (a) |
| 28 | 317 (a) |
| 29 | 124 (c) |
| 30 | 813 (a) |
| 31 | ND |
| 32 | ND |
| 33 | ND |
| 34 | ND |
| 35 | 486 (a) |
| 36 | ND |
| 37 | 84 (a) |
| 38 | ND |
| 39 | 74 (a) |
| 40 | 50 (a) |
| 41 | 72 (a) |
| 42 | 219 (a) |
| 43 | ND |
| 44 | ND |
| 45 | 50 (a) |
| 46 | 43 (c) |
| 47 | 42 (a) |
| 48 | 62 (a) |
| 49 | ND |
| 50 | 35 (a) |
| 51 | NA |
| 52 | 54 (a) |
| 53 | NA |
| 54 | >1000 (a) |
| 55 | ND |
| 56 | 735 (a) |
| 57 | >1000 (a) |
| 58 | ND |
| 59 | ND |
| 60 | >1000 (a) |
| 61 | 51 (c) |
| 62 | ND |
| 63 | ND |
| 64 | ND |
| 65 | 228 (a) |
| 66 | 84 (a) |
| 67 | NA |
| 68 | 64 (a) |
| 69 | 331 (a) |
| 70 | 85 (a) |
| 71 | 6 (a) |
| 72 | 7 (a) |
| 73 | 49 (a) |
| 74 | 96 (a) |
| 75 | 16 (a) |
| 76 | ND |
| 77 | ND |
| 78 | 246 (a) |
| 79 | ND |
| 80 | >1000 (a) |
| 81 | 199 (a) |
| 82 | 56 (a) |
| 83 | 205 (a) |
| 84 | 55 (a) |
| 85 | ND |
| 86 | 105 (a) |
| 87 | 502 (a) |
| 88 | 134 (a) |
| 89 | ND |
| 90 | ND |
| 91 | ND |
| 92 | ND |
| 93 | >1000 (a) |
| 94 | >1000 (a) |
| 95 | >1000 (a) |
| 96 | 36 (a) |
| 97 | ND |
| 98 | 315 (a) |
| 99 | 36 (a) |
| 100 | 12 (a) |
| 101 | 83 (a) |
| 102 | ND |
| 103 | 125 (a) |
| 104 | 37 (a) |
| 105 | 22 (a) |
| 106 | ND |
| 107 | 653 (a) |
| 108 | ND |
| 109 | 14 (a) |
| 110 | 126 (a) |
| 111 | ND |
| 112 | 198 (a) |
| 113 | 651 (a) |
| 114 | 656 (a) |
| 115 | 415 (a) |
| 116 | 369 (a) |
| 117 | 117 (a) |
| 118 | 381 (a) |
| 119 | 199 (a) |
| 120 | ND |
| 121 | 166 (a) |
| 122 | ND |
| 123 | 176 (a) |
| 124 | ND |
| 125 | ND |
| 126 | 542 (a) |
| 127 | >1000 (a) |
| 128 | ND |
| 129 | ND |
| 130 | 198 (a) |
| 132 | ND |
| 133 | ND |
| 134 | ND |
| 135 | ND |
| 4A | 92 (c) |
| 4B | ND |
| 100A | ND |
| 100B | 24 (a) |
| 100C | 38 (a) |
| 100D | ND |
| 100E | ND |
| 100F | ND |

(a) - mean of 2 tests
(b) - mean of 3 tests
(c) - mean of 4 tests
ND—not determined
UA—unavailable Example 138

Animal Model for Inhibition of Sebum Production

Luderschmidt et al describes an animal model for testing whether compounds are capable of modulating sebum secretion. Arch. Derm. Res. 258,185-191 (1977). This model uses male Syrian hamsters, whose ears contain sebaceous glands. Based on binding data and cellular assay data, selected compounds were chosen for screening in this model. Those compounds included the products of Examples 1, 20, 81, 82, and 109.

Testing for sebum inhibition was carried out in the following manner. Male Syrian hamsters aged 9 to 10 weeks were introduced into the laboratory environment and acclimated for 2 weeks prior to use in the study. Each group consisted of 5 animals and run in parallel with vehicle and positive controls. Prior to administration, a sufficient quantity each compound was dissolved in 1 mL of a solvent consisting of ethanol, transcutol, and propylene glycol (60/20/20% v/v/v) to achieve the final concentration specified in Table VIII below.

Animals were dosed topically twice daily, five days a week, for 4 weeks. Each dose consisted of 25 micro liters of vehicle control or drug. The dose was applied to the ventral surfaces of both the right and left ears. All animals were sacrificed approximately 18-24 hours after the final dose. The right ears were collected from each animal and used for sebum analysis.

The ears were prepped for HPLC analysis in the following manner. One 8 mm distal biopsy punch was taken, just above the anatomical "V" mark in the ear to normalize the sample area. The punch was pulled apart. The ventral biopsy surface (the area where the topical dose was directly applied to the sebaceous glands) was retained for testing and the dorsal surface of the biopsy punch was discarded.

Tissue samples were blown with $N_2$ gas and stored at $-80°$ C. under nitrogen until HPLC analysis. In addition to ear samples, an aliquot of each drug and vehicle (at least 250 ul) was also stored at $-80°$ C. for inclusion in the HPLC analysis.

HPLC analysis was carried out on an extract of the tissue sample. Tissue samples were contacted with 3 ml of solvent (a 4:1 admixture of 2,2,4-trimethylpentane and isopropyl alcohol). The mixture was shaken for 15 minutes and stored overnight at room temperature, protected from light. The next morning 1 milliliter of water was added to the sample and shaken for 15 minutes. The sample was then centrifuged at approximately 1500 rpm for 15 minutes. Two ml of the organic phase (top layer) was transferred to a glass vial, dried at $37°$ C., under nitrogen, for approximately 1 hour, and then lyophilized for approximately 48 hours. The samples were then removed from the lyophilizer and each vial was reconstituted with 600 µl of solvent A (trimethylpentane/tetrahydrofuran (99:1). The samples were then recapped and vortexed for 5 minutes.

200 µl of each sample was then transferred to a pre-labeled 200 µl HPLC vial with 200 µL glass inserts. The HPLC vials were placed in the autosampler tray for the Agilent 1100 series HPLC unit. The Agilent 1100 HPLC system consisted of a thermostated autosampler, a quarternary pump, a column heater, and an A/D interface module. All components were controlled by Agilent ChemStation software. A Waters Spherisorb S3W 4.6×100 mm analytical column was maintained at $30°$ C. by the Agilent column heater unit.

The HPLC autosampler was programmed to maintain the sample temperature at $20°$ C. throughout the run.

10 µL of each sample was injected in triplicate into the column. Two solvents were used for the solvent gradient. Solvent A was an admixture of trimethylpentane and tetrahydrofuran (99:1). Solvent B was ethylacetate. The gradient utilized is described in the table below:

TABLE VII

| Time (min) | Solv A (%) | Solv B (%) | Flow (mL/min) |
|---|---|---|---|
| 0 | 99 | 1 | 2 |
| 2 | 96 | 4 | 2 |
| 6 | 60 | 40 | 2 |
| 7 | 5 | 95 | 2 |
| 10 | 5 | 95 | 2 |
| 10.1 | 99 | 1 | 2 |

The Sedex 75 Evaporative Light Scattering Detector (ELSD) was operated at $45°$ C. with a gain of 5, and $N_2$ pressure maintained at 3.1 bar. Analog signal obtained by the instrument was sent to the Agilent A/D interface module where it was converted to a digital output. The conversion was based on a 10000 mAU/volt set point and the data rate was set at 10 Hz (0.03 min). The resulting digital output was then feed into the Agilent ChemStation software for integration of the peak area.

The results of the HPLC analysis are reported below in Table VIII. The results are reported as the reduction in cholesterol ester (CE) and wax ester (WE) production, when compared to the vehicle control. A negative value reflects an increase in sebum, whereas a positive reflects a decrease.

TABLE VIII

| Example # | % CE reduction | % WE reduction | Sum of WE & CE | Concen. Tested |
|---|---|---|---|---|
| 1 | 70 | 55 | 125 | 1% |
| 20 | 83 | 66 | 149 | 2% |
| 81 | 12 | 8 | 20 | 1% |
| 82 | 72 | 57 | 129 | 1% |
| 109 | 64 | 52 | 116 | 1% |
| 4 | 76 | 90 | 166 | 3% |
| 4A | 76 | 85 | 161 | 1% |

Example 139

The following Example illustrates the preparation of a number of topical formulations, suitable for use with human subjects.

TABLE IX

| Topical Formulation | A | B | C | D |
|---|---|---|---|---|
| (3R,S)-(+)-4-(1-sec-Butyl-4,4-dimethyl-2-oxo-pyrrolidin-3-yloxy)-2-trifluoromethyl-benzonitrile. | 1% | 1% | 1% | 1% |
| Propylene glycol | 20% | 5% | 5% | 10% |
| Transcutol | 20% | | | |
| PEG 400 | | | | 15% |
| Propylene carbonate | | 3% | | |
| Hexylene glycol | | | 5% | |
| Water | | | 30% | 20% |
| Ethanol | q.s | q.s | q.s. | q.s. |

*All percentages are w/v %

The far left column identifies the components that are present in the formulation. The subsequent four (4) columns indicate the amount of each individual component that is in the formulation. A blank indicates that the formulation did not incorporate that component.

The formulations are made by weighing the appropriate weight of the non-volatile components, water and the active. Ethanol is then added to reach the target volume of the formulation, which is 100 ml. The mixture is stirred as required to dissolve the components.

Example 140

Using the procedure of Example 139, but substituting the compound of Example 4A and the components described below, the following topical formulation is prepared:

| Topical Formulation | A |
|---|---|
| (+)-4-(1-Propyl-4,4-dimethyl-2-oxo-pyrrolidin-3-yloxy)-2-trifluoromethyl- | 1% |

-continued

| Topical Formulation | A |
|---|---|
| benzonitrile (E2) | |
| Propylene glycol | 10% |
| Water | 30% |
| Ethanol | q.s. |

*All percentages are w/v %

What is claimed is:

1. 4-(1-Benzyl-4,4-dimethyl-2-oxo-pyrrolidin-3-yloxy)-2-trifluoromethyl-benzonitrile, or a pharmaceutically acceptable salt thereof.

2. 4-(1-Benzyl-4,4-dimethyl-2-oxo-pyrrolidin-3-yloxy)-2-trifluoromethyl-benzonitrile, an individual enantiomer of 4-(1-benzyl-4,4-dimethyl-2-oxo-pyrrolidin-3-yloxy)-2-trifluoromethyl-benzonitrile, or a pharmaceutically acceptable salt of 4-(1-benzyl-4,4-dimethyl-2-oxo-pyrrolidin-3-yloxy)-2-trifluoromethyl-benzonitrile, or its individual enantiomers.

3. (+)-4-(1-Benzyl-4,4-dimethyl-2-oxo-pyrrolidin-3-yloxy)-2-trifluoromethyl-benzonitrile, or a pharmaceutically acceptable salt thereof.

4. A pharmaceutical composition comprising an effective amount of a compound according to any one of claim 1, 2, or 3, in admixture with at least one pharmaceutical excipient.

5. A method for alleviating alopecia comprising administering an effective amount of a compound according to any one of claim 1, 2, or 3 to a patient in need thereof.

6. A method for alleviating androgenic alopecia comprising administering an effective amount of a compound according to any one of claim 1, 2, or 3 to a patient in need thereof.

7. A method for treating acne comprising administering an effective amount of a compound according to any one of claim 1, 2, or 3 to a patient in need thereof.

8. A method for alleviating oily skin comprising administering an effective amount of a compound according to any one of claim 1, 2, or 3 to a patient in need thereof.

9. A method for decreasing sebum secretion comprising administering an effective amount of a compound according to any one of claim 1, 2, or 3 to a patient in need thereof.

10. A topical pharmaceutical composition comprising a compound according to any one of claim 1, 2, or 3 in admixture with at least one pharmaceutical excipient suitable for topical administration.

* * * * *